United States Patent

Pollock et al.

[11] Patent Number: 5,854,034
[45] Date of Patent: Dec. 29, 1998

[54] DNA SEGMENTS AND METHODS FOR INCREASING POLYSACCHARIDE PRODUCTION

[75] Inventors: Thomas J. Pollock; Motohide Yamazaki, both of San Diego; Linda Thorne, Palomar; Marcia Mikolajczak, Encinitas; Richard W. Armentrout, La Jolla, all of Calif.

[73] Assignees: Shin-Etsu Cio, Inc., San Diego, Calif.; Shin-Etsu Chemical Co., Ltd., Tokyo, Japan

[21] Appl. No.: 592,874

[22] Filed: Jan. 24, 1996

Related U.S. Application Data

[63] Continuation-in-part of Ser. No. 377,440, Jan. 24, 1995.
[51] Int. Cl.$^6$ .............................. C12P 19/04; C12P 19/06; C12P 1/21; C12P 21/04; C12N 1/21; C07N 21/04
[52] U.S. Cl. ............................ 435/101; 435/72; 435/104; 435/252.3; 536/23.2
[58] Field of Search .............................. 435/72, 101, 104, 435/172.1, 252.3, 253.3; 536/23.2

[56] References Cited

U.S. PATENT DOCUMENTS

| | | | |
|---|---|---|---|
| 4,326,053 | 4/1982 | Kang et al. | 536/1 |
| 5,338,841 | 8/1994 | Pollock et al. | 536/23.7 |

OTHER PUBLICATIONS

Martins, L.O. et al. "Gellan gum biosynthetic enzymes in producing and nonproducing variants of Pseudomonas elodea." Biotechnology and Applied Biochemistry, vol. 14, No. 3 (1991), pp. 1357–364 1991.

Harding, N.E. et al. "Isolation of genes essential for the biosynthesis of gellan gum." FASEB Journal, vol. 7, No. 7 (Apr., 1993), p. A1259.

Pollock, T.J. "Gellan–related polysaccharides and the genus Sphingomonas" Journal of General Microbiology, vol. 139, (1993), pp. 1939–1945.

Alberts, B. et al. Molecular Biology of the Cell, Second Edition. N.Y., Garland Publishing, 1989. pp. 258–266.

Martin, M.O. "Synthesis of commercially valuable bacterial polymers: impact of molecular genetics." Research in Microbiology, vol. 145, (1994), pp. 93–97.

Fialho, A.M. et al. "Conjugal transfer of recombinant plasmids into gellan gum–producing and non–producing variants of *Pseudomonas elodea* ATCC 31641." Letters in Applied Microbiology, vol. 12, (Mar. 1991), pp. 85–87.

*Primary Examiner*—Rebecca E. Prouty
*Assistant Examiner*—Kawai Lau
*Attorney, Agent, or Firm*—McAulay Nissen Goldberg Kiel & Hand, LLP

[57] ABSTRACT

The present invention relates to DNA segments isolated from Sphingomonas sp. and involved in the biosynthetic production of sphingan polysaccharides to increase the production of the polysaccharide in engineered microorganisms. The present invention also relates to methods of engineering strains of Sphingomonas to produce bacteria which are hyperproducers of sphingan, methods of identifying and utilizing DNA fragments useful to enhance production of sphingan in bacteria and the hyperproducer bacteria.

31 Claims, 33 Drawing Sheets

RESTRICTION MAP FOR S60 DNA
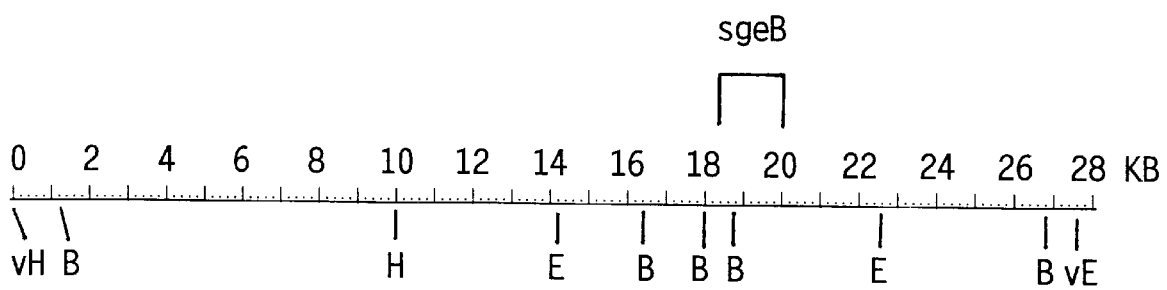
DNA fragments showing homology to S88-E4.5:
c2:
c1 fragment remaining after spontaneous deletion:
· · · ——————— · · ·
c3 fragment remaining after spontaneous deletion:
Fig. 2

FIGURE 4

DNA Sequence of spsB Gene

```
AGCCCGAATG.CTGCATCCGC.GAAGTGACTT.TCGCCAAAGC.AGCTATAGGA    50
TGGCCCGGGG.CTTGATTGCC.GCCGTGCGAT.CAGCATAAGC.GATCCATGGT   100
CGCCAAAATC.TGTCATCCTT.GGTAACAATC.ATGCAGCCGC.TAAGGAAGAT   150
GTGCACGTCT.GACGATGCTT.TCTTCCGCAC.CCCATGCGCC.GCTGACTCTG   200
GTAGATTGAC.CGTGGCCTCC.ATTGCTCATC.GTCTCGAAAA.AGGACCCTCT   250
GGTCGCCGCG.CGGACTTCCG.GGAATCGATT.TGTCCCGTTA.TAGTGCAATG   300
CAACAGGCCG.AATCGGCCGC.TGTCAGCGTG.CACAATCCGT.TGAGGGAGCC   350
CGACGAGGCA.ATGAACGCTT.TTGAAGCACA.GCGCGCCTTT.GAGGAGCAGC   400
TCCGGGCCCA.TGCCCGTTCT.GCCCCCAGCG.CCGCACCCAT.GCTGCGACGT   450
TCCACGATCC.GCATGATCCT.CTACACCGAA.TTGCTGTTGC.TCGACAGCAT   500
CGCAATTCTA.CTGGGGTTCT.ACATCGCGGC.CTGCTCGCGC.GACGGCAACT   550
GGCTGTCCCT.TGCGGGCGTC.AATGTCGGCA.TCTTCCTCCT.GCCGATCACG   600
CTCGGCACCG.CGCTCGCCAG.CGGCACCTAT.TCGCTGAGCT.GCCTGCGCTA   650
CCCGGTCAGC.GGGGTGAAGA.GCATCTTCTC.GGCGTTCTTC.TTCTCGGTGT   700
TCATCGTGCT.GCTGGGCAGC.TACCTGCTCA.CCGCGGAGCT.GCCGCTGTCG   750
CGCCTGCAGC.TCGGCGAGGG.CGTGCTCCTG.GCGCTCAGCC.TGGTGACGAT   800
CTGCCGCCTT.GGCTTCCGCT.GGCACGTTCG.TGCGCTGACA.CGCGGCACGC   850
TGCTCGACGA.GCTGGTGATC.GTCGACGGCG.TTGCCCTGGA.GGTCGCGAGC   900
GGCGCGGTCG.CGCTCGATGC.GCGCATCATC.AACCTCACGC.CCAACCCGCG   950
CGATCCGCAG.ATGCTGCATC.GCCTCGGCAC.CACCGTGGTG.GGCTTCGACC  1000
GGGTCGTCGT.CGCCTGCACC.GAGGAGCACC.GGGCAGTATG.GGCGCTGCTG  1050
CTCAAGGGCA.TGAACATCAA.GGGCGAGATC.CTCGTCCCCC.AGTTCAACGC  1100
GCTGGGCGCG.ATCGGCGTCG.ACTCCTATGA.GGGCAAGGAC.ACGCTGGTCG  1150
TGTCCCAGGG.CCCGCTCAAC.ATGCCGAACC.GCGCAAAGAA.GCGGGCGCTC  1200
GATCTGCTCA.TCACCGTCCC.CGCGCTGGTC.GCGCTGGCGC.CGCTGATGAT  1250
CGTGGTCGCG.ATCCTGATCA.AGCTGGAGAG.CCCCGGCCCC.GTCTTCTTCG  1300
CACAGGACCG.CGTCGGCCGC.GGCAACCGAC.TGTTCAAGAT.CCTCAAGTTC  1350
CGCTCGATGC.GCGTTGCGCT.CTGCGATGCG.AACGGCAACG.TCTCGGCCAG  1400
CCGCGATGAC.GATCGCATCA.CCAAGGTAGG.CCGGATCATC.CGCAAGACCA  1450
GCATCGACGA.GCTGCCGCAG.CTGCTCAACG.TGCTGCGCGG.CGACATGAGC  1500
GTCGTCGGCC.CGCGCCCGCA.CGCACTCGGG.TCGCGCGCCG.CCAACCATCT  1550
CTTCTGGGAA.ATCGACGAGC.GCTACTGGCA.CCGCCACACG.CTCAAGCCGG  1600
GCATGACGGG.CCTCGCGCAG.ATCCGCGGCT.TCCGCGGCGC.GACCGATCGC  1650
CGCGTCGATC.TCACCAATCG.CCTGCAGGCG.GACATGGAGT.ATATCGACGG  1700
CTGGGACATC.TGGCGGGACG.TCACCATCCT.GTTCAAGACG.CTGCGCGTGA  1750
TCGTGCACTC.CAACGCCTTC.TGATCGCGGA.GGGGAGCAAC.GCGAGCACCG  1800
CTTGGTGCAA.GAGCATTGAC.ATCCGCCCTG.CTTCTGCATT.TGTCATTTTA  1850
TCATTGTCGT.TGCGGGCCCG.CCCGCGCCAT.GGGGGATTTT.GAATGAAGGG  1900
TATCATCCTT.GCGGGGGGCA.GCGGCACGCG.CCTCTACCCC.GCAACGCTGT  1950
```

FIGURE 5

Deduced Amino Acid Sequence of the SpsB Protein

MNAFEAQRAFEEQLRAHARSAPSAAPMLRRSTIRMILYTELLLLDSIAIL
LGFYIAACSRDGNWLSLAGVNVGIFLLPITLGTALASGTYSLSCLRYPVS
GVKSIFSAFFFSVFIVLLGSYLLTAELPLSRLQLGEGVLLALSLVTICRL
GFRWHVRALTRGTLLDELVIVDGVALEVASGAVALDARIINLTPNPRDPQ
MLHRLGTTVVGFDRVVVACTEEHRAVWALLLKGMNIKGEILVPQFNALGA
IGVDSYEGKDTLVVSQGPLNMPNRAKKRALDLLITVPALVALAPLMIVVA
ILIKLESPGPVFFAQDRVGRGNRLFKILKFRSMRVALCDANGNVSASRDD
DRITKVGRIIRKTSIDELPQLLNVLRGDMSVVGPRPHALGSRAANHLFWE
IDERYWHRHTLKPGMTGLAQIRGFRGATDRRVDLTNRLQADMEYIDGWDI
WRDVTILFKTLRVIVHSNAF

FIGURE 6

POLYSACCHARIDE STRUCTURE

Gellan

```
                                                            L-Glyceric
                                                                1
                                                                ↓
                                                                2
              →4)-β-D-GlcA-(1→4)-β-D-Glc-(1→4)α-L-Rha-(1→3)-β-D-Glc-(1→
```

Sphingan S-88
```
              →4-β-D-GlcA-(1→4)-β-D-Glc-(1→4)-α-L-Rha-(1→3)-β-D-Glc-(1→
                                   3         or
                                   ↑         Man
                                   1
                                α-L-Rha
```

Welan
```
              →4)-β-D-GlcA-(1→4)-β-D-Glc-(1→4)-α-L-Rha-(1→3)-β-D-Glc-(1→
                                   3
                                   ↑
                                   1
                           α-L-Rha(2/3) or Man (1/3)
```

Sphingan NW11   →4)-β-D-GlcA-(1→4)-β-D-Glc-(1→4)-α-L-Man-(1→3)-β-D-Glc-(1→

Sphingan S-198
```
              →4)-β-D-GlcA-(1→4)-β-D-Glc-(1→4)-α-L-Rha-(1→3)-β-D-Glc-(1→
                                        or                    3
                                        Man                   ↑
                                                              1
                                                      (1/2) α-L-Rha
```

S-657
```
              →4)-β-D-GlcA-(1→4)-β-D-Glc-(1→4)-α-L-Rha-(1→3)-β-D-Glc-(1→
                                   3
                                   ↑
                                   1
                          α-L-Rha-(1→4)-α-L-Rha
``` rhamsan
S-194
```
              →4)-β-D-GlcA-(1→4)-β-D-Glc-(1→4)-α-L-Rha-(1→3)-β-D-Glc-(1→
                                                               6
                                                               ↑
                                                               1
                                                   α-D-Glc-(1→6)-α-D-Glc
```

Restriction map for S198 DNA

Restriction map for S7 DNA

PHENOTYPES OF CHROMOSOMAL (c) AND
PLASMID (p) MINI-TN10KAN INSERTIONS:

```
                                                       pY987
                                       cY575                        cB345
                             cB583       pY929  cY570  pY994
                        pY974 cB580  cY578  cB343   pY997  pZ009
           cB589   pY958 pY945 cB579 pY890   pY911   pY999 cB299
             -  -    -    -     -    -+  ++    +    +++ +     +
```

COMPLEMENTATION OF SPS- MUTATIONS BY PLASMIDS
CARRYING S88 GENES WITH MINI-TN10KAN INSERTIONS:

```
              B289
         B248        B282  B258
         B290  B249        B254
         B264
    (E)  +++    -    -    - +
    (C)  +++    -    -    - +
    (D)  +--    -    +    + +
```

SPS- MUTATIONS:
```
    62  76  69   3
    68  78  72   9
    94      b104 41
```

?  Sec  Sec  Sec  Urf  Urf  ABC-transporter

| F→ | D→ | C→ | E▸ | 32▸ | 26▸ | ←atrD | ←atrB |

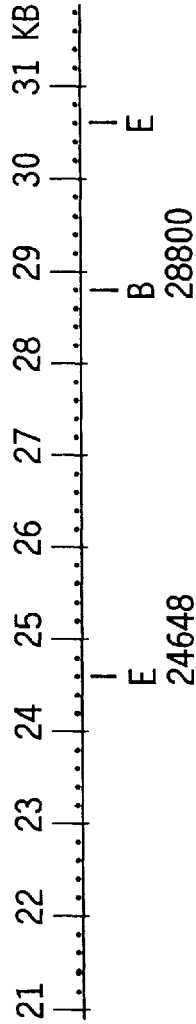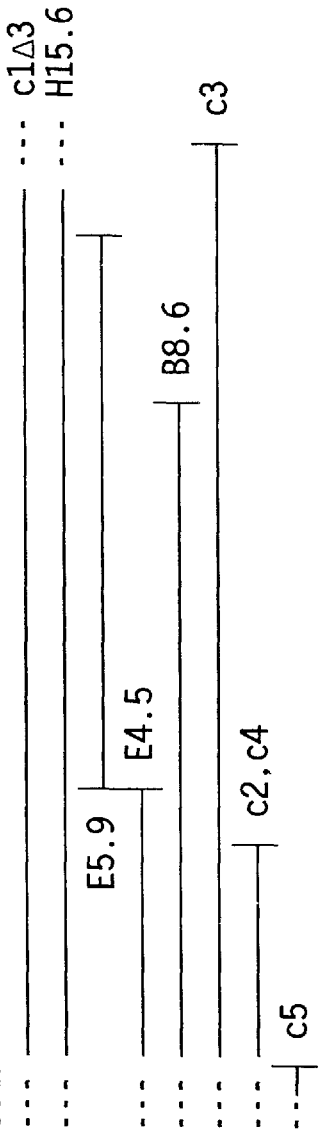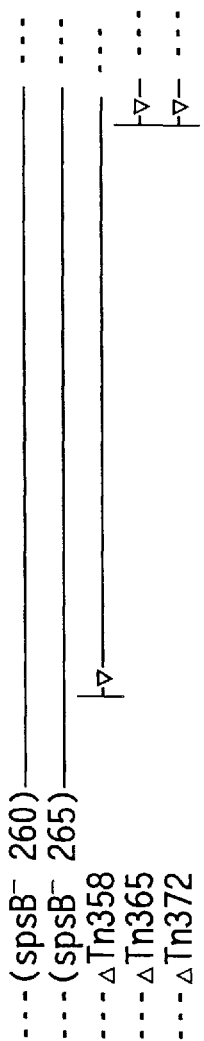
Fig. 11f

FIGURE 12a

```
              MDNIDNKYNPQLCKIFLAISDLIFFNLALWFSLGCVY    37  RfbP
                    MNAFEAQRAFEEQLRAHARSAPSAAPMLRRSTIR    34  SpsB
MLLADLSSATYTTSSPRLLSKYSAAADLVLRVFDLTMVVASGLIAYRIVF    50  GumD

FIFDQVQRFIPQDQLDTRVITHFILSVVCVGWFWIRLRHYTIRKPFWYEL    87  RfbP
MILYTELLLLDSIAILLGFYIAACSRDGNWLSLAGVNVGIFLLPITLGTA    84  SpsB
GTWVPAAPYRVAIATTLLYSVICFALFPLYRSWRGRGLLSELVVLGGAFG   100  GumD

MNSFLKYYRKY    11  CpsD
KEIFRTIVIFAIFDLALIAFTKWQFSRYVWVFCWTFALILVPFFRALTKH   137  RfbP
LASGTYSLSCLRYPVSGVKSIFSAFFFSVFIVLLGSYLLTAELPLSRLQL   134  SpsB
GVFALFAVHALIVQVGEQVSRGWVGLWFVGGLVSLVAARTLLRGFLNHLR   150  GumD

SYAKFSRDTKVVLITNKDSLSKMTFRNKYDHNYIAVCILDSSEKDCYDLK    61  CpsD
LLNKLGIWKKKTIILGSGQNARGAYSALQSEEMMGFDVIAFFDTDASDAE   187  RfbP
GEGVLLALSLVTICRLGFRWHVRALTRGTLLDELVIVDGVALEVASGAVA   184  SpsB
TQGVDVQRVVVVGLRHPVMKISHYLSRNPWVGMNMVGYFRTPYDLAVAEQ   200  GumD

HNSLRIINKDALTSELTCLTVDQAFINIPIELFGKYQIQDIINDIEAMGV   111  CpsD
INMLPVIKDTEIIWDLNRTGDVHYILAYEYTELEKTHFWLRELSKHHCRS   237  RfbP
LDARIINLTPNPRDPQMLHRLGTTVVGFDRVVVACTEEHRAVWALLLKGM   234  SpsB
RQGLPCLGDPDELIEYLKNNQVEQVWISLPLGERDHIKQLLQRLDRYPIN   250  GumD
                          VTGLTIDRLLPPRPLEDNRVRSLSIT    26  Pss4

MKSATRSATTAFFIPQETGAIRPIGGISKRSFDVLI    36  ExoYn
IVNVNVEALSFDNIGEKRIQTFEGYSVITYSMKFYKYSHLIAKRFLDITG   161  CpsD
VTVVPSFRGLPLYNTDMSFIFSHEVMLLRIQNNLAKRSSRFLKRTFDIVC   287  RfbP
                                    ||  :|:
NIKGEILVPQFNALGAIGVDSYEGKDTLVVSQGPLNMPNRAKKRALDLLI   284  SpsB
                            :      |  |  :
VKLVPDLFVFGLLNQSAEQIGSVPVINLRQGGVDRDNYFVVAKALQDKIL   300  GumD
ELNNSISTESFRPSRRQQPSLKIQTPVIHSDAPQAPLVDLVLKRAFDIVS    76  Pss4
                                MDLVLKRAFDIFS    13  Pss2

AILALIALSPLFLLVMGLVKFSDGGSIFYGHRRIGHNGQTFKCLKFRTMM    86  ExoYn
AIIGLLICGIVAIFLVPQIR-KDGGPAIFSQNRVGRNGRIFRFYKFRSM-   210  CpsD
SIMILIIASPLMIYLWYKV-TRDGGPAIYGHQRVGRHGKLFPCYKFRSMV   337  RfbP
  :  ::    :   :    ::     |  :   |:|:    |   |||:|
TVPALVALAPLMIVVAILIKLESPGPVFFAQDRVGRGNRLFKILKFRSM-   333  SpsB
  :  ||: |  |:::|  :|:   :|:  |||||:|  |  |    :    :   |||||
AVIALMGLWPLMLAIAVGVKMSSPGPVFFRQRRHGLGGREFYMFKFRSM-   349  GumD
SLSALLVLAPFLLFVALLIKIDSPGPVLFKQTRWGKNCKAIKVYKFRSM-   125  Pss4
SLSALLVLAPFLLFVALLIKLDSPGPVLFKQTRWGKNCKAIKVYKFRSM-    62  Pss2
```

FIGURE 12b

```
ENGDRVLQEFFKSN-PAAYEEWRTTRKLQDDPRVTVVGSVLRKLSLDELP   135  ExoYn
----RVDAEQIKKDLLVHNQMTGLMFKLEDDDPRITLIGKFIRKTSIDELP  256  CpsD
MNSQEVLKELLAND-PIARAEWEKDFKLKNDPRITAVGRFIRKTSLDELP   386  RfbP
    |              :| |:|  :|  ::|| |:||||
----RV----------ALCDANGNVSASRDDDRITKVGRIIRKTSIDELP   369  SpsB
    |              :| |:|::|  ::|:: :||||
----RT----------DLCDVSGVAQTVKNDPRITRIGAILRRTNVDELP   385  GumD
----RT----------DLCDVSGVAQTVMNDPRVTRVGAILRRTNVDELP   161  Pss4
----RV----------HDDHGTTIQQATKNDTRITRFGSFLRRSSLDELP    98  Pss2

QLLNIIRGEMSIVGPRP---VVEDELELYDSAAEFYLRS---RPGLTGLW  179  ExoYn
QFYNVLKGDMSLAGTASHS                                 275  CpsD
QLFNVLKGDMSLVGPRP---IVSDELERYCDDVDYYLMA---KPGMTGLW  430  RfbP
|: |:::|:||: |              : |:    :||:|||
QLLNVLRGDMSVVGPRPHALGSRAANHLFWEIDERYWHRHTLKPGMTGLA  419  SpsB
|::||| | ||:|||| ||    :      |  || ::||:||:|
QIFNVLGGSMSIVGPRPHAA-QHN--THYEKLINHYMQRHYVKPGITGWA  432  GumD
QLLNVLLGHMSVVGPRCHAIGMRAGGVLYEELVPEYHQRHAMRPGMTGLA  211  Pss4
QLLNVLLGHMSVVGPRCHAIGMRAGGMLYEELVPEYHQRHAMRPGMTGLA  148  PSs2

QISG-RND----VSYATRVAFDTHYVQNWSLLADLVIVFKTIPAVCLSRGSY  226  ExoYn
QVSG-RND----VDYDTRVYFDSWYVKNWTLWNDIAILFKTAKVVLRRDGAY  476  RfbP
|: | |      |    |:  |  |:   |  :: |:  |:|||    :
QIRGFRGATDRRVDLTNRLQADMEYIDGWDIWRDVTILFKTLRVIVHSN-AF  470  SpsB
|: |:|| |       |:   |:  |  : ::  |:  |:::   |    :
QVNGFRGETPELRTMKKRIQYDLDYIRRWSLWLDIRIIVLTAVEVLGQKTAY  484  GumD
QMRGLRGPTDRPAKARARIASDLYYVGNFSILMDMRIIFGTVVSELTRGKGF  263  Pss4
QMRGLRGPTDRPAKARARIASDLYYVGNFSIVMDMRIIFGTVVSELTRGKGF  200  Pss2
```

FIGURE 13a rfbA / rhsA

```
MKTRKGIILAGGSGTRLYPVTMAVSKQLLPIYDKPMIYYPLSTLMLAGIR   50   S.e.
|   ||||||||||||||| |: :|||||:||||| |||| ||| |||
M---KGIILAGGSGTRLYPATLSISKQLLPVYDKPMIFYPLSVLMLTGIR   47   S88
|   ||||||||||||||| | :|||||||||||| |||||||| |||
MTQRKGIILAGGSGTRLYPITKGVSKQLLPVYDKPMIYYPLSVLMLAGIR   50   X.c.

DILIISTPQDTPRFQQLLGDGSQWGLNLQYKVQPSPDGLAQAFIIGEEFI   100
|||||||| | || |||||| :|:|| | ||||:|||:||||| :|:
DILIISTPRDLPMFQALLGDGSAFGINLSYAEQPSPNGLAEAFIIGADFV    97
||||| ||:: :|| ||||| :|:|: ||:|||:|||:|:||| |||
DILIINTPHEQALFQSLLGDGAQWGVNIQYAVQPSPDGLAQAYLIGRDFV   100

GHDDCALVLGDNIFYGHDLPKLMEAAVNKES--GATVFAYHVNDPERYGV   148
|   || :||||| |   :    :||   |   ||  ||||||:|||||||
GNDPSALILGDNIYHGEKMGERCQAAAAQASQGGANVFAYHVDDPERYGV   147
|   || |:|||||| ||   ::       ||   || ||||| |:|||||||
GGKPSCLVLGDNIFHGHGLTDTLRRADARE-Q-GATVFGYWVNDPERYGV   148

VEFD-QKGTAVSLEEKPLQPKSNYAVTGLYFYDNSVVEMAKNLKPSARGE   197
| ||  : |  | |:|||| :|||| |:||||||| ||::|| : ||||||
VAFDPETGVATSVEEKPANPKSNWAITGLYFYDKDVVDIAKSIQPSARGE   197
|| : :  ||| |:|| |:||||:|||||| ||||: |||||
AEFD-QHGKVIDIAEKPEKPRSNYAVTGLYFYDGKASDYAAALKPSPRGE   197

LEITDINRIYMEQGRLSVAMMGRGYAWLDTGTHQSLIEASNFIATIEERQ   247
||||| :||||||  | |   :||||||||||:|| ||   |: |:|  |
LEITDVNRIYMERGDLHITRLGRGYAWLDTGTHDSLHEAGSFVRTLEHRT   247
||||||:|| |:: ||||: |||||||||||||:|||||   |: |:: |
LEITDLNRCYLDAGDLHLEPLGRGYAWLDTGTHQSLHEAANFIETIQMRQ   247

GLKVSCPEEIAFRKNFINAQQVIELAGPLSKNDYGKYLLKMVKGL        292
|:|: |||||||  :: |::::|   |   |   |   ||  |:|
GVKIACPEEIAFESGWLGADDLLKRAAGLGKTGYAAYLRKLVAAA        292
|: : |||||||  ||: |::|| |||   | ||  |:|
GLQVCCPEEIAFGQGWIDAEQLERLAAPLLKNDYGKYLTALAKRGAVH    295
```

FIGURE 13b

*rhsB / rfbB*

```
VKILITGGAGFIGSAVVRHIIKNTQDTVVNIDKLTYAGNLESLSDISE   48   S.e.
MQQTFLVTGGAGFIGSAVVRHLVRQGAR-VINLDKLTYAGNPASLTAIEN 49   S88
VATWLVTRGAGFIGANFVLEAVSRGIR-VVNLDALTYAGNLNTLASLEG  49   X.c.

SNRYNFEHADICDSAEITRIFEQYQPDAVMHLAAESHVDRSITGPAAFIE 98
APNYRFVHADIADTATILPLLREEQVDVVMHLAAESHVDRSIDGPGEFIE 99
NADHIFVKGDIGDGALVTRLLQEHQPDAVLNFAAESHVDRSIEGPGAFIQ 99

TNIVGTYALLEVARKYWSALGEDKKNNFRFHHISTDEVYGDLPHPDEVEN 148
TNVVGTFKLLQAALQYWRELEGEKREAFRFHHISTDEVFGDLP------ 142
TNVVGTLALLEAVRDYWKALPDTRRDAFRFLHVSTDEVYGTL------- 141

SVTLPLFTETTAYAPSSPYSASKASSDHLVRAWRRTYGLPTIVTNCSNNY 198
-FDSGIFTEETPYDPSSPYSASKAASDHLVRAWGHTYGLPVVLSNCSNNY 191
-GETGKFTETTPYAPNSPYSASKAASDHLVRAFHHTYGLPVLTTNCSNNY 190

GPYHFPEKLIPLVILNALEGKPLPIYGKGDQIRDWLYVEDHARALHMVVT 248
GPFHFPEKLIPLTILNALEGKPLPVYGKGENIRDWLYVDDHAKALATIAT 241
GPYHFPEKLIPLVIAKALAGEPLPVYGDGKQVRDWLFVSDHCEAIRTVLA 240

EGKAGETYNIGGHNEKKNLDVVFTICDLLDE-IVPKATSY-REQITYVAD 296
TGKVGQSYNVGGRNERTNLQVVETICDLLDQRIPLKDGKKRRELITFVTD 291
KGRVGETYNVGGNSERQNIEVVQAICALLDQHRPREDGKPRESQIAYVTD 290

RPGHDRRYAIDAGKISRELGWKPLETFESGIRKTVEWYLANTQWVNNVKS 346
RPGHDRRYAIDATKLETELGWKAEENFDTGIAATIDWYLENEWWWGPIRS 341
RPGHDRRYAIDASKLKDELGWEPAYTFEQGIALTVDWYLTNQTWVQGVLD 340

GAYQSWIEQNYEGRQ 361
GKYAGERLGQTA    353
GSYRLERIGATV    352
```

FIGURE 13c

*rhsC / rfbC*

```
M-IVIKTAIPDVLILEPKVFGDERGFFFESYNQQTFEELIGRKVTFVQDN    49   S.e.
MTQVHHHALSGVIEFTPPKYGDHRGFFSEVFKQSTL-DAEGVEARWVQDN    49   S88
      VIETTLPGCVVIEPAVFGDERGQFFETWNAERFGQ-HGLPTSFVQSN    46   X.c.

HSKS-KKNVLRGLHFQRGENAQGKLVRCAVGEVFDVAVDIRKESPTFGQW    98
QSFSAAPGTIRGLHLQAPPFAQAKLVRVLRGAIYDVAVDIRRGSPTYGQW    99
 VSTSA-RGVLRGLHYQ-WPRPQGKLVSVLEGEVYDVAVDIRAGSPHFGRW   94

VGVNLSAENKRQLWIPEGFAHGFVTLSEYAEFLYKATNYYSPSSEGSILW    148
VGVELSADKWNQLLVPAGYAHGFMTLVPDCEILYKVSAKYSKESEMAIRW    149
 TAVLLSAENRRQVWIPEGFAHGFAVLSEKALFSYLCTDVYVKEADAGVRW   144

NDEAIGIEWPFSQL-PELSAKDAAA-PLLD-QA-LLTE               182
DDPDLAITWPDIGVEPVLSEKDAVATPFAEFNTPFFYQG              188
DDAAIGIDWP--VSDPSLSAKDAKA-PFLDEV-PVDRLPVYRP          183
```

FIGURE 13d

*rhsD / rfbD*

```
MNILLFGKTGQVGWELQRSLAPVGNLIALDVH-SK---EFCG--DFSNPK    44   S.e.
 | ||: |: |||    |     |     ||         ||    |:||
MRILVTGHDGQVAQAL-GEQAEGHELIFTSYP------EF----DLSKPE    39   S88
 :  || |:|||    |       |  |:             |:  ||
VTTLVFGANGQVGAELLRALAADGAVQATTRSGRLPDGSACETADFDAPE    50   X.c.

GVAETVRKLRPDVIVNAAAHTAVDKAESEPELAQLLNATSVEAIAKAANE    94
 :    |   |: |:: ||  ||| ||||||| |||||||  :|     :|:|
TIEAAVAKIQPELIVSAAAYTAVDKSESEPELAMAINGDGPGVLARAGAK    89
|:  |   :|  |  |:| ||||||||   ||     |    :  :  |:|
TLPALLDRIGPSLVVNAAAYTAVDCAEQDRVSAMRANAQAPLTIAAWCAA   100

TGAWVVHYSTDYVFPGTGDIPWQETDATSPLNVYGKTKLAGEKALQDNCP   144
 ||  ::| ||||||| |     |  |  |  |  ||| |||||| |:|
IGAPIIHLSTDYVFDGSLDRPWREDDPTGPLGVYGATKLAGEQAVQASGA   139
 |::| ||||||||    |   |||   ||||||||:|:  ||||
RDVPLVHSTDYVFDGQDTAPYLEDAQTSPLGVYGETKLAGENAIRASGA   150

KHLIFRTSWVYAGKGNNFAKTMLRLAKERQTLSVINDQYGAPTGAELLAD   194
 ::| ||| |||| |||||||| |:|| |::|| | |   :|
TNAVIRLAWVYSPFGNNFVKTMLRLAETRDTLNVVEDQQGCPSSALDIAT   189
   :       :|   :       || |  || || |   | ||
QHLDPAYGMGVRIARREFPAHHVACRAERDELRVVADQIGTPSRRALIAD   200

CTAHAIRVALNKPEVAGLYHLVAGGTTTWHDYAALVFDEARKAGITLALT   244
 : :        ||||:    | | |  |||    ||  ||  ||
AILKVVGHWQQNGATSGLYHFTGSGETNWADFARAIFAESAKHG-GPTA-   237
 |    :    |||  |:|  |:| || ||||    |  |||
-ITAQLLR-QRTAETSGTWHLTAAGQTSWHGFAEAIFEEAVSAGLLPRAP   248

ELNAVPTSAYPTPASRPGNSRLNTEKFQRNFDLILPQWELGVKRMLTEMF
|:   :|||  ||||||| || |||||  :||    |     ||:
EVTGIPTSGYPTPAKRPANSRLNCDKFAETFGYRAPAWQDSVAEVVGRLL
 |  |   ||||||||||  |||  :|:     |    ||  :  |:  :
RVVPITTADYPTPAKRPAYSRLSIEKLQRDFDIVLPEWRPGLQRVIAEVA

TTTTI   299

A       288
|
AARQ    302
```

FIGURE 14a

```
GGATCCACTGGCCGGGAATTGCCGAGAATCCTCCGATGAAGCGCTCGTCG
GGTACCAGCGTGCCCCGGGGCGCATCGCTTTGCGCCGGCGCATCGCCGCC
GCTGCCGGGCCGGCCATTCCAGCGGGGTCCGGGCTGCAAAATCCCCGGGC
CTGCCTTTACGCCATGCCCGGCAGCCGAGCTGCCGGGCGCCGAGCATGCG
AGCGGCGTAACCGATAGGGCGAGGCCCCGCCCAGAAGGGTGCGACGTGT
GGTATCGATCATGCGGCGCGCTCCAAACCGTGCGCGCCGTGACTACAACC
AAAAATGCTGCGCTGCGAGCGGGATCAGGCGCCCCGTGCCTGCTTCGAGC
GGTACAGCAGCGCGAACGTCAGCCCCACCAGCATGAAGAAGACTTGGTCG
TTGTCGGTCTGCGACAGCACGAGCCTGGTATTGAGCAGCACGACCATCGT
CGTCGCGACCGCCAGATGCAGCGGATAGCCTTGGGAGGGGTCCGTCAACC
CGGCGCGGATCAACAGCCCGGCACCCAGCACCATCGTACCGTAGAATGCG
ATGAAGCCGAGCACCCCGTAATCGACGGCCGTCGAAAGGAAGCCGGAGTC
GATCGACAGGAACCCGCTCTGGGAACGCCATCCGACGACCTCCGCGGACT
GGAACGGCCCGTAGCCGAATACCGGGCGCATCGCGAGCTTGGGCAAGCCC
ATGCGGATCTGCTCGTGGCGCCCGTCGTTGCTCGCCTGGGTCGCGCCGCC
GCCAAGAACGCGATTGTGTACCGCAGGCACTACCATGATCATCACCGCGA
GAACCACGGCGAAGGCCGGATACATCATCGTCGTGGAAATCCCGACGAGC
CCGCCACGCTCCTTGATCCAGCGCCGCAGGCCCCAGAGCAACAGATAGGT
GGCATGCGCCACGACCATGCCGACCATGCTCAGGCGCGCGCCGCTCCAAT
AGGCGGACAATACCATGGCGAGATCGAACAGGATCGTGAGTGCCAGCGCC
GACACCGACCGGCTGTTCACCATCAGGTGGATCGCGAAGGGAATCGTCAT
CGCCACGAGTTCGCCCCACACCAGCGGGTTCCCGAACACGTTCATCACGC
GATACGTGCCGCGCACCTGCGAGGTGAGATGCAGGATGACGCTCGGATCG
TTGATCTGCAGCCAGCTGGGAATGTGGCCGACCCACAGAACGTGCTCGGC
CCGGAACTCGAAGAAGCCGATCACCATCAGCACGGACACGCAGCCCAGCA
TGTTCCGCACCCACCATTCGGGTGTGCGCGTGTTCGATCCCAGGCACCAC
AGCGTCGCGAAGAAGAACGGCGTGACCGTCAGCGAGATATTCACCAGGCG
CCCGATCGAAACGGATGGCTGGCTGGAAATGAGCGACGCGATGATCTGGA
TGATCAGGAAGCCCAGCATGAAGCGGGCAAGCCAGGGCGACGCCGACAGC
GTCACCGCCATGTCGCGCCGAAACTTCGGCGAAATCGAATAGCACACCAG
CAGAAGAAGCGTCGTCAGCACGCCGAACAGGCGGCGGAAGGAGATCCAGG
GCAGGCCCGCCACCGACAGCGACAGATAGTTCGGCCACACGATCGCGAGG
ATCATGAACAGGACGTAGCAGCGCAGCAGCAACTTGGTGGGCGCCTTGTC
GGCCTCCGGGAGCGCCCAGATGACGAACAGCGCGAGGATCGCCAGCGGCG
CGGCGGCCCCGAGGAGCATGCTGGGCGGCAGGATCGCCGAAAGCAGCCCG
TAGACCATCGACACGAACACGATCACGGCGAGCCCGATGAAGCGCCGCCC
GAGCGTGACGAGACCAGAGCGTTGCGGGTGATAGAGCGGGAGCACCGCTC
TGGCGGGGAAGAACACGATGTCGCGCGCCCGGCGCAGGGGCTGCACCACC
CGCGCCAAGCCGCCGCTCCCCCGAACTCGCGCCGATGTCGCCATGACCAA
CCCCTTAGATAATCGGTATGCCGATCAGCCGCACCGCGACCATCGACACG
AAGCGCAGGAAGACCGACGGCACCGCGATCGCAATCGCCGCGCCTAGTGC
ACCATAGGGCGGAATCAGGACCAGCGCGAGTATTGCGGCAAGGATAACCG
ACGACATGGTCAGCACCACGGCCAGACGCTCGCGATTGGCCATGACGAGG
ACGCCGCCGCTCGACGCGAAGACCATCCCGAACACCTGCCCAAGCACCAG
CACCTGCATCGCGGCGGCGCCCGCGGTGAACTGTTTGCCGAACAGGCCCA
TGATCCAATGCGGAGCGACCAGCACCGCCAGGGCGATGGGCGAGGCGGCG
ACCAGCAGCGCGAGAATGGTGATCCGGATGATGCGGGCGATCCGCTTGAC
GTCGCCCTGTTCGTAGGAGGCGGCAAAGACCGGATGCAGGATCGTCTCGG
AGGTGGCCGACAGCAACTTGAGCGAGGATGCGATCTGATAGCCCACCCGG
AACAGACCGGCTTCGGCGGGCCGTGCGTCGCGGCAAGGATCACGGTGGC
AAACCAGTCGACGAAGAAGTTGTTGACGTTGGTGATCAGCACCATGAAGC
CGGGGCGAAGCATCGGCCGGTCCAACGGCTCGGCCGGCGCCCAATCACGC
GTCATGCGGCGGACGATGATCGTCGCGGCAAACATCGTCACCAGCCAGCC
GACCAGGTACAGCACCGACGGCAGCAGCGGATTATGGGCAACGCCGATCA
```

FIGURE 14b

```
GCAGCGCGCCGGCCAGCATCGCCCCACCCAGGAAGGTGCCGAGCGGCCCA
TCGACCATCTGCGACTTGCCGATATCCCCCATGCCGCGCAGCGTCGTCGA
AGCGAGACGGCAATAGGCGCTGACCGGAATGAGAAACCCCATGATCAGAA
GGTCCGGCGCCATGGCGGGGCTGCCCAGCAGGTTGGTGGCAATCTGTTGG
TGAAACAGCAGGATCATCACCATCAGGACCAGGCCACCACCCACCGCGAC
CCGCGTGGCATGCCGCACTGCGGTACGCGCCACACCCGTCCGATTTTGCG
ACACGCAGACGGCCACGGTGCGCACCAGGATGGTATCGAGGCCGATCAGC
GACAGAATGACCAGCATCTGCGCAGTCGTGAGCGCCGTACCGAAGGCACC
GACGCCGGCGGGCCAAAGGCGCGGGCGACCAGCCAGGTGAAAGCGAAAC
TGGTGACGGCGCCGAAGCCCTTGACGCCGAAGCCGACCACCATCTGCCCC
CGCAGCCCCGCAGGTGCAACTTGCTACGTGTCACGTTAATGCTTGCCC
CACAGGAGATCCCGTCTGTGCCTTATGGCAGGGCCCTCCCGGGGCAAGC
CTGAGGACGTCATCAGACGTGATAGAAGTCCTGCACCAACTTCTTGGTGG
CGAACAGGCTATTCGCCACGGACAGGCTGCCCGTCGCCGAGACGGCCGCA
GTGCCGGCCGCATTCATGGCGATCGCCTGGGCGAGCGACACTTGCGCGAC
GGACGCCGTCGATGCCGATCCCCCAGCGTCAGCGTGCCGGTGGTCGCCG
CCGGCAGCGCCGTCGACGTGACCGGGGTGCCGAGAATGGTTACGGCGCTG
GCGGCCAAGCTGCTGGTGAGGCTGGGCTTCACGGTGGTGGTCGGCTGGCT
GGCGGCGGTCGCCGCGGCATTCAGCGCAAGGATCTGGGACGCACTGAGGG
CAGCGTCGCGCATCTCGATCTCGCCCACGCTGCCGCTGAAGACAGCGTTG
AACGGGCTGCCGATGTACAGTCCGGCATATTCGACCGCCCGCGTGCTGCC
GACGATCGTTCCCGATCCCTTCACCACGCCATCGACATAGATGATCGCCT
TGCCCTTCGCGCTGTCATAGGTCAGCGCGATCTTGTGGGTGGCCGTGTCG
GTCATCTTGGCGCCGCTCGTCGCGACGGTATAGCTCTGCCCGGCGGCATT
CTTGACGGTGAAGACCAGTTCGCCGTCCGCCCGGAGCGAGATTCCCCAGC
TCTGGTTGACGCCCATGATCTGGCCGACCGCGCCCGTCGCGGTGGCACGC
TTCATGTCGAAGTTGAGCGTGAAGGCGGGCAGCGCGAAGAGTTGACGTGA
ATTGTCCCGCGTAAGCTCGAAGCCGGTGCCGGTCTTCACCTGGAACATGC
CGTTGCTGATGGCGGTGAGATCCAGCGCCTTCGTGGTCTCGTCCGTGCTC
CAGCGCGTCTGGTCCACGATTCCGGTCGCAGTGAACTGCAGATCCAGCAG
CAGGTTGGCGCCGGTCGAGGTCTGTGCTGCCGCCTGCTCCTTGGCGACCT
GCGCGGCAAACGCGCTGCCTGCAGGCGGCTGATACCCGACACCACTGACG
ATCAGGTTCGCCAGTTGCGCCTTCGATCCGGCCATGAGATCGCCGATCTT
GCGAAGAGTGACCGCGTCCGTTGCAAGCACGGCGTTGTTCGATTGAGTAA
TGCCGCTCGACGTTGCGGTGATGACAACCTGGTCCACGACATTGTTGGTG
ACCTTGCCGCCGGTCACGCCGTCCAGGCGGATCCAATCGGCGATCGCATC
CATCTTCGAGATGATGGTATTGGAGTCCACGGTGACGTTCTTGCCCAGAA
CGACATTGATGCCGTGCGTGAAACCATTCTGGTACACGAGATTGTTTTTG
ATCGTGATGTTTTCGTAGGGAATGCTGGATTCATTGCCCATGAATACGCC
CTGGAAGGCCAGGCCGTCCCCCTGCATCATCACGTTATTGGTGATCGTGA
TGTTCGTGTTGCCCTTGGTCTTGCCGTTCGTCATGAACTGGATGGCGTCG
GGATGCTCACCATTCACCGGATAGAGGTTGGTGAACATGTTGTTGTCGAT
GACGACGTTCGACGCTTCGGCGAAATTGGTGTGATCGCGGCGATTGTCGT
GGAAGTTGTTGCCCTGCAGGGTGACACCGTCGACGGTGAGGACGTTCATC
CCCAGGGCGAAATGATCGACCGAGGAATTCTTGATCGTCACCCCCTTGCT
TTCTCGCAGCAGAAGCCCCAGCCCATCGACTTCGTCACATCGCCCGTAC
CCCCGCTCAGGGTCACGCCGTCGATCACGACATTGCTGGAGCCGATGATC
CGGTTCGCGTAATTATAGTCCTGTGCCGGCTGGAAGTTTTGTGCGGCCGT
GACGTTCTTCACCACCAGGTTGCTGCTGTTGATGATCTGCAGGGTCGTCA
CATTCACCGGCTTGCTCGCATCGAGCGAGGTGATCGTGACGGGCGTGGTG
AAGGTCGTGGTGTGCACGGTGATGGACGTATAGGTCCCCGCCGCAAGCTT
GATCGTCTCGCCCCCTTTCGCAGCCTTGATGGCGGCGTCCAGTTCGCTCT
GATTCCTCACGATGATGTCCGGCATGTACTCTACCCTCGTTACGCGTCGA
CCCCAATCGACCTGCGATCCCTCGGACCGTCTTGTACCTGCCAAGCCCTG
```

FIGURE 14c

```
AAACGGTGGCTAAGAGGCAGGGTTAATGCCCTGTTTTTCAAGCCGATAAC
TGGCAGCCCTCAAGGCACTGCCAGCGTGCGGGCAACACTCTCGACGCCGC
AGTGCAGCACGGGTAAGAACGAGGCATGGAAGCCTCGCCCACACCCGACG
TCAGCATCCTGGTGGTTGCCTACCACTCGGCTCCGTTCATCGGACAATGC
ATCCGGGGCATCGCCGCGGCGGCACAAGGCACAGCCCACGAAATCCTGCT
GATCGACAATGGCGGCGGCGACACCGAGGCGGTGGTTCGTGCCGAGTTCC
CGCACGTGCGGATCGTGCCGAGCGAGGGCAATATCGGCTTCGGGGCGGGG
AATAACCGGTGTGCGGCCCATGCCCGCGCCGCGGCTGCTGCTCGTCAA
CCCCGACGCCATTCCCCGCCCCGGCGCGATCGACCTGCTGGTCGCCTTCG
CCAAGGCGCACCCGGACGCGGCAGCCTGGGGCGGGCGTTCCTATTTTCCG
AACGGCCAGCTGGACCATGCCAACTTCCTCCCGCTGCCCACGGTGCGCGA
TTTCGTCGTGTCGATCTTCAGCAGCAGCCCGATGCGGCGCGGCGGCCTTC
CTGCCGACGCCACCGCGCCCGGGCCGGTCGAGGTGCTCAACGGCGGCTTC
ATGATGGTCGATGCCCGCGTGTGGCGGGAGATCGACGGCTTCGACGAAGG
CTTCTTCCTCTATTCGGAGGAAATCGATCTGTTCCAGCGGATCCGCGCGC
GGGGCTATTCCGTGCTGGTCGATCCGGCTGTGGGCGTGGTGCACGACACC
GGTGGCGGGCATTCGCTCTCGCCCACTCGCGTGCTGTTTCTCACCACCGG
CCGCATGCATTATGCCCGCAAGCATTTCGGCCACGTCGGTGCCGTCGTGA
CGGGCTGGGCACTGTGGGCCAATGCCGCCAAATATGTCGTTATCGGCGGC
CTGCTCGGGCGCCTCTCACCCCGCCGCGGCGCGCTGGAACGCGCTGCG
CGATGCCTGGAGCATCGTGTTCGGCCAGCCGCGGCGCTGGTGGCACGGCT
GGCGCGACCACGTTCGTACTTGAGGATAGCGCCGCGCCAGACGGCCCGAA
ATGGCAACCCGACGCAAGGCGGAAGGCTTGCCGACGGCAAGCCCCCCGAC
TTGTCGCTCACTGCGCGGCGTTGGGCGCCGGAGCAGGGGCCGCAGCAGGC
GCGGCGGCAGCGCCGCCCTGCAGTTGCGGCGGCGGGCTGTAGCCCGGCTG
ATATTTCACCGACTCGCGCGCCTTCTTCAGACGATCGTTCAGCTGCGCGT
CCGCCGCCTTGCTGAACCGCTCGGTGCGCAGCGTATTGAGCGCGAGTTCG
CGCGCCTGATCGCCCGCCAGCGGCTGGATCGTCGTGCCGGTGATGACATT
GGCGGTGACGCCCTGCTGCGTCGGCAGGATGAACAGCTCCTGCGCCGGCA
GCGCCGCAATCTTGGCGGCGATCTCCGGCGGCAACGCGGCGGTGTCCAGC
TGGGTCGGCGCGCGGCGGAACTGCACGCCGTCGGCGGTCAGCTTGGCGGC
AAGCTGGTCCAACGTCTTGAGCGGCGCGAATTCCTTGAACTTCGCCGCCG
AGCCGGGCGGCGGGAAGACGATCTGTTCGATGCTGTAGATCTTGCGCTGC
GCGAAGCGATCGGGATGCGCCGCTTCATATTGCGCGATCTCGGCATCGGT
CGGCTGGGCGATGCCGCCGGCAATCTTGTCGCGCAGCAGCGTGGTGAGGA
TCAACTCGTCGGCGCGGCGCTGCTGGATCAGGAAGACGGGGGTCTTGTCC
AGCTTCTGCTCGCGGGCGTACTTCGCGAGAATCTTGCGCTCGATGATGCG
CTGCAGCGCCATCTGCTCGGCAAGCTTGCGGTCGGTCCCCTGCGGCACCT
GCGTGGCCTGCACTTCGGCATTCAGTTCGAAGATGGTGATCTCGTCGCCG
TCCACGCTGGCGACGACCTGCCCCTTATCGAGCTTGCCTTCCTTGCTGCC
ACATCCGGAGACGGCCAGCGCGGCCGCAGCCACCGCCGTTACCAGGTACA
ATTTCTTCATGAAGACCTCCCAGCCGGCACGGAATTGCGCACGGCACAAA
CTTCTACTTGAACCTATTCGGGCGGGCGGGCATCCGCAATAGCGTTGGCA
GTGCAGCATGCCTCCCGGCGGGAGGCAGGCGGGATCAATGGGGACGGCA
TGGCAGAAGCGACGGTGACCGAAGCGAAGGCGGGCAAACCGCTGAAAATG
TGTCTCGCAGCTTCCGGCGGCGGCCATCTGCGGCAGATCCTCGATCTGGA
ATCGGTCTGGAAGGAACATGACTATTTCTTCGTGACCGAAGACACCGCGC
TGGGCCGCAGCCTTGCCGAAAAACACTCGGTCGCGCTTGTCGATCACTAT
GCCCTCGGCCAGGCCAAGCTCGGCCACCCGCTGCGCATGCTGGGAGGCGC
CTGGCGGAACCTGCGGCAGAGCCTGTCGATCATCCGCAAGCACAAGCCCG
ATGTGGTGATCTCCACCGGTGCGGGCGCGGTCTATTTCACGGCGCTGCTC
GCCAAGCTCTCGGGCGCAAAGTTCGTCCACATCGAAAGCTTCGCCCGGTT
CGATCATCCTTCCGCCTTCGGCAAGATGGTCAAGGGCATCGCGACCGTGA
CCATCGTCCAGTCCGCCGCGCTCAAGCAGACCTGGCCGGATGCGGAGCTG
```

FIGURE 14d

```
TTCGATCCCTTCCGCCTGCTCGACACCCCCGCCCTCCCAAGCAGGCACT
CACCTTCGCCACCGTCGGTGCCACCCTGCCCTTTCGCGGCTCGTGCAGG
CCGTGCTCGATCTCAAGCGGGCCGGCGGGCTGCCGGGCAAGCTGGTGCTG
CAATATGGCGACCAGGACCTGGCCGACCCCGGCATCCCCGACGTGGAGAT
CCGCCGGACCATTCCCTTCGACGACCTCCAGCTGCTGCTGCGCGACGCGG
ACATGGTGATCTGCCACGGCGGCACCGGATCGCTGGTCACCGCGCTGCGC
GCCGGCTGCCGCGTCGTCGCCTTCCCGCGCCGCCACGATCTGGGCGAGCA
TTATGACGATCACCAGGAAGAGATCGCGCAGACCTTCGCCGATCGCGGCC
TGCTCCACGCCGTGCGCGACGAGCGCGAACTGGGCGCGGCAGTGGAGGCC
GCCAAGGCGACCGAGCCGCAGCTCGCCACCACCGATCACACGGCGCTCGC
CGGCCGCCTGCGCGAGTTGCTGGCACAGTGGAGTGCCAAGCGATGAGCGC
GCCGCGGATCAGCGTCGTCATCCCGCACTACAATGATCCGGACTCGCTGC
GACAATGTCTCGATGCACTGCAGCATCAGACGATCGGGCGAGAGGCCTTC
GAGATCATCGTCGGAGACAACAACTCCCCCTGCGGCCTGGCGGCAGTGGA
AGCCGCCGTAGCCGGGCGCGCGCGGATCGTCACGATCCTGGAGAAGGGCG
CCGGACCGGCGCGGAACGGCGCCGCGGCGGAAGCGCAGGGCGAGATTCTC
GCCTTCACCGACAGCGACTGCGTCGTCGAGCCCGGCTGGCTGGCCGGGGG
CGTCGCCCATGTCGCCCCGGGCCGCTTCGTCGGCGGCCACATGTATGTGC
TCAAGCCGGAAGGGCGACTGACCGGCGCGGAAGCACTCGAGATGGCGCTG
GCCTTCGACAATGAAGGCTATGTTCGCCGTGCGAAGTTCACCGTCACTGC
CAATCTGTTCGTCATGCGGGCCGATTTCGAGCGCGTCGGCGGATTTCGTA
CCGGAGTCTCGGAAGATCTGGAATGGTGCCACCGCGCCATCGCCACGGGT
CTCGCGATCGACTACGCCCCGAGGCCTCGGTAGGCCACCCGCCCCGGCC
GGACTGGGCAACGCTACTGGTCAAGACGCGGCGCATCCAGCGCGAGCTGT
TCCTGTTCAATATCGAGCGCCCGCGCGGCCGGCTGCGCTGGCTTGCGCGC
TCGACGCTGCAGCCTGCGCTGATTCCGGCGGATACCGCCAAGATCCTGCG
CACGCCCGGCACCCGCGGGTCCCGTATAGCTGCCGTCGGCACGCTTGTCC
GCCTGCGCTTCTGGCGCGCTGGCGCCGGCCTCCTGCAACTGCTCGGCAGA
CCAATCTGATGAAGGCGGGCGGCCATGGTGCGGCGCCCGTCTCCTGTC
CTCACACCGCCGCGAGCGCCTCTTCCAGCGTCCCGCTGTCGATCCGCAGG
CGTCCCACCATCAGCCAGAGATAGACGGGCAGCGAATCGTCGTTGAAGCG
GAAGCGGCGCTCCCCGTCCTGCGCATCGCTCTCCAGGCCGAGCTGGCGGC
TCAGCGCGTCGAGTTCCTGCTCGACCTGCGCCGCAGTGATCGTGCTCCCC
GGCAGCAGCTCGACGACTGCCTGGCCGGTGAACCAACCATCGGTCGAACG
CGACGCCTCGCCCAGCGCGGCGACCAGCGGATCGTAGCGACCGCCGACGA
ACTTGCGCATCTCCAGCACGGCGCGCGGCGACATCCGGCCTTCTATTTCC
AGGATGGCCTGGTCGAGCGCGCGGCGCAGATGGCCCAGATCGACGGTCAG
CCGCCCCTGGTCGAGCGCCTCGAGCGCCGCATGGTGGCACAGCAGCCGCG
CGAAATAGGGCGACCCCAGCGCCAGCAGGTGGATGATCCGGGTGAGGTTC
GGATCGAAGCGCAGGCCCGAGGCGGTCTCGCCGAGCGCGATCATCTCCTG
TACCTCGGTTTCCTCGAGCCGCGGCATCGGCAGGCCGATGATGTTGCGGC
GGATCGAGGGTACGTAGCCGACGAGTTCCTGCAGGTTCGACGAGACGCCG
GCGATCACCAGCTGTACGCGCGCGGAGCGGTCCGAGAGGTTCTTGATCAG
TTCGGCGACCTGCTGGCGGAACCGGGTATCCGTCACGCGGTCATATTCGT
CGAGGATGATCAGAACGCGGGTGCCGGTGATGTCGGCGCACAGATCGGCG
AGTTCGCCCGAATCGAACGATCCGGTCGGCAGGCGATCGGCGAGGCTTCC
GCCCGATTCCGCCTCGCCCGCATTGGGCGAGACGCCGCGATGGAACAGCA
GCGGCACATCCTCTAGCACCGCGCGGAACAGGTCGGCGAAGTTGGCATTG
GCGCCGCAGGTCGCGTAGCTGACGATGTAGCTGGATTCACGCGCCACGTC
GGTCAGCACATGGAGCAGCGAGGTCTTGCCGATGCCGCGCTCGCCATAGA
GCACGACATGGCTGCGCTGGCTCTCGATCGCCGAGATCAGCCGCGCCAGC
ACCTCGAGGCGACCGGCAAAGCTCGAGCGGTCCGCCACCGGCTGGGTGGG
CGTGAAGAAGGTGGCGAGCGCAAACCGCGCGCGGGTGATCTCGCGACGCT
CTTCCCGGCGCCGGTCGAGCGGGCGATCGAGCGCGGAAGCGCGAAAGGTC
```

FIGURE 14e

```
GGAAAGTCGGGTCGCCCGCGGCCCGCATGCGCGTCGCGATGGGGAACGAC
GGTGGCGGCCAGCGGGAAATATCCGTCCTCCTCCGGTACGTCCCGACGCC
CAAAGGGCCACAAGAACTTCAGCGCGGATCCTACAGCCACTCGAACACCT
CTTAATTTCGGACGCCGCCACGCTCGGCAGCGAACCCCTGGTTCGCGCCT
TCTGGCGCCTCCCCCAAACGATCCGGCCCCGCCTGTATCAGCGGCGCTTG
AAAAACTCGTACGGTTTGATCACGAACGCAATGTACGCCAGCACCAATAC
AATCGTGAGGATTGCGAAAACATGATAGTTTTCGTTCCCGAGATAATTGG
CGACGGCACATCCGACCGCGGGAGGCAAATAGCTGATCATCGTGTCGCGC
ACTACCGAATCCGCCTGGGATCGTTGCAAGAAGATCACGATCAGGCCGGC
GAATATCGCGATGGTCACCCAATCATAGGGCGTCTGCATGCATGTCCTTT
CTTTTCGGCGCCGGAATCGAAGGACTTCCGACGTCGCCCGAACCGCACTA
GCAGCGGACGGTGCAACTCGCTAGATACCGCGGTGCAGGATAAAAGCTCG
TTAAAACGCGACCCTAGGAATAGCGCGGTAGCGCCGGCATGCGAGAGGTC
GGGCATGCGGAAGGCCGAAGCGGCCGGACAGCACCGGATGGGAGGATAT
TCCCGTAGTGGGAGTGGCGAGGCCATGGCATCCTCAGATCCGGTTGCTTG
TACTGGAGGCCATTGATAATGAAGCCAGGACCCGGGGAACATTCGTGCC
AGTAAAAGACGTTCAGCAAGCGGTAGAAGTGCGCCTCGGCGATCGTGTCT
CGCGATCGTGCCGCGTGCTCGCGCTGCTTGCGACGGCAACGGCGATCCAG
CCCGCGCTCGCGCAGCGACAGGCGTTCACGCCACGCCCGAGCGGCAGCGA
GCGCCAGATCAGCGTGCATGCAACGGGACAGCTCGAGTACAACGACAATG
TCGTGCTCAACGACCCGCGCATCACCAGCGGCGCGCGCGGCGACGTGATC
GCCTCCCCCTCCCTCGATCTGAGCATTGTCCTGCCGCGCGCGACCGGACA
GCTCTATCTCGCGGGCACGGTGGGCTATCGCTTCTATCGTCGCTACACGA
ACTTCAATCGCGAGAATATCTCGCTCACCGGCGGCGGCGACCAGCGGATC
GCGTCCTGCGTGGTGCATGGCGAAGTCGGCTATCAGCGCCACCTGACGGA
CCTGTCCAGCGTCCTCGTCCAGGATACTGCGCCCGCGCTCAACAACACGG
AAGAAGCGCGCGCCTATTCCGCGGACATCGGCTGCGGGTCCGCCTACGGC
CTGCGCCCTGCACTTGCCTATTCGCGCAACGAGGTTCGCAACAGCCTCGC
CCAGCGCAAGTTCGCCGATTCCGACACCAACACGGTCACTGCCCAGTTGG
GCCTGACGTCGCCGGCGCTGGGCACCGTGTCGGTGTTTGGACGCATGTCC
GACAGCAGCTACATCCATCGCACGGTACCGGGGGTCAGTGGCCGCGACGG
CATGAAGAGCTATGCGGCCGGCGTCCAGCTCGAGCGGCGGTCTCCAGCC
GGCTGAATTTCCGCGGCTCCGTCAATTATTCGGAGGTCGACCCCAAGCTC
GCCTCGACGCCGGGCTTCAGCGGGATCGGATTCGATCTGTCGGCGGTATA
TTCGGGCGATCAATATGGCGTGCAGCTCCTTGCGTCGCGCAACCCGCAGC
CCTCCACGCTGCTGTTCGTAGGCTATGAAATTGTGACGACCGTGTCGGCA
ACGGCAACCCGTAAGCTGAGCGATCGGACCCAACTCTCGCTACAGGCCAC
CAAGACCTGGCGCGAGCTTGCCTCTTCGCGGTTGTTCACTCTTGCGCCGA
CGACGGGCAACGACAACACGCTGACGCTGTTCGGCACCGTGAACTTCCGA
CCCAATCCTCGGCTGAACTTCTCGCTGGGTGCGGGCTATAACAAGCGCAC
CAGCAATATTGGGCTGTATCAATACCGCTCCAAACGTATCAATCTCACGA
CGTCGCTGTCGCTCTGACAAGGGCCGTATTCATGCATGACAAACACCGTT
TCGTGATCCTTTCGGCGCTCACCGGAATTGCCGTACTCGCCGCGCCCGCG
GCAGCGCAGATTCCCACCCGGTCCGTTCGACGCCGGCGCGGGCGCGCCC
GGCGACCCCGCCAGCGGCCCCGCAGCAGCAGACGACGGCAGTGCCGACAA
CGGCAGCCACCGCCACCCCGCCGGCTGCGGGTGCGGCGCCGGCCGGCTAC
AAGATCGGCGTCGACGACGTGATCGAGGCGGACGTTCTGGGCCAGTCGGA
CTTCAAGACCCGCGCGCGTGCAAGCGGACGGTACCGTCACCCTTCCCT
ATCTCGGCGCCGTGCAGGTACGGGGCGAGACCGCCGTCACGCTGGCCGAG
AAGCTCGCCGGCCTGCTGCGCGGGTGGCTATTACGCGAAGCCGATCGT
CAGCGTCGAAGTCGTCAGCTTCGTCAGCAACTATGTGACGGTGCTGGGCC
AGGTGACCACGGCCGGCCTGCAGCCGGTGGATCGCGGCTATCACGTCTCG
GAGATCATCGCGCGCGCCGGCGGCCTTCGCGCCGATGCGGCCGATTTCGT
GGTGCTCACCCGCGCCGACGGCACCAGTGCCAAGCTGAACTACAAGCAGC
```

FIGURE 14f

```
TGGCCCAGGGCGGCCCGGAGCAGGATCCGGTGGTCACGCCTGGCGACAAG
CTGTTCGTGCCGGAAGTCGAGCACTTCTACATTTATGGCCAAGTTAACGC
GCCTGGGGTATACGCGATTCGAACGGACATGACGCTCCGTCGCGCGCTGG
CACAAGGCGGCGGCCTTACCCCGCCGGCTCGTCGAAGCGAGTGAAGGTC
TCGCGCGACGGCCAGGAAATCAAGTTGAAGATGGACGATCCGATCAAGCC
TGGCGACACGATCGTCATCGGCGAGCGGTTGTTCTGATCTAGGCAATGTT
GACAGCGGACGAGGCCCACCAGTGAATATCATTCAGTTCTTCCGCATTCT
CTGGGTGCGCCGGTGGATCATCCTCCCGGCGTTTCTCGTCTGCGTCACCA
CCGCGGCGCTGGTGGTCCAGTTCCTGCCCGAACGCTACCGCGCGACCACG
CGGCTGGTGCTCGACACCTTCAAGCCCGATCCCGTCACCGGCCAGGTGAT
GAACTCGCAGTTCATGCGCGCCTATGTCCAGACGCAGACCGAGCTGATCG
AGGACTATGCGACCTCCGGCCGCGTGGTCGACGAACTGGGCTGGGCCAAC
GATCCTGCCAACATCGCTGCCTTCAACGCCTCGTCCTCGGCGGCGACCGG
CGACATTCGCCGCTGGCTCGCAAAGCAGATCTCGGACAACACCAAGGCGG
ATGTGATCGAGGGCAGCAACATCCTCGAAATCTCCTACTCGGACAGCTCG
CCCGAGCGTGCCGAGCGTATCGCCAACCTGATCCGCACCGCATTCCTCGC
CCAGTCGCTCGCCGCCAAGCGCCAGGCGGCGGCGAAGTCGGCCGACTGGT
ACACCCAGCAAGCGGAAGCGGCACGCCAGTCGCTGCTCGCGGCGGTGCAG
GCGCGCACCGACTTCGTGAAGAAGTCCGGCATCGTGCTGACCGAGACCGG
TTCGGATCTCGATACGCAGAAGCTCGCACAGCTCCAGGGCGCGAGCGCGA
TACCGTCGGCACCGGTCGTCGCGGCCGCCAGCGGCATGGGCCCGGCGCAG
CTCCAGCTTGCCCAGATCGACCAGCAGATCCAGCAGGCGGCCACCAATCT
CGGCCCGAACCACCCGGCCTTCCAGGCCCTGCAGCGCCAGCGCGAGGTGC
TCGCCCGCGCAGCGGCGGCGGAACGCAGCCAGGCAAGCGCCAGCGGCCCC
GGCCGCGGCGCGCTGGAAAGCGAAGCCAATGCCCAGCGCGCCCGCGTGCT
CGGCAACCGCCAGGATGTCGACAAGGTCATGCAGCTCCAGCGGGACGTCA
CGCTGAAGCAGGACCAGTATATGAAGGCGGCCCAGCGCGTCGCCGATCTG
CGCCTGGAAGCAAGCAGCAACGACACGGGCATGAGCACGCTGAGCGAAGC
CAGCGCGCCGGAAACGCCCTATTACCCCAAGGTGCCGATGATCATCGGCG
GCGCGGCCGGCTTCGGCCTCGGCCTCGGCGTGCTGGTCGCGCTGCTCGTC
GAACTGCTCGGTCGCCGCGTGCGCAGCGCCGAGGATCTCGAAGTGGCGGT
CGATGCGCCGGTGCTGGGCGTGATCCAGAGCCGTGCCTCGCTCGCCGCAC
GCCTGCGCCGCGCCCAAGAAACCCTCGGCGACCGCGCCGAAACGCACGGA
GCTTCAGTAAACTGATGGACGCGATGACCAGCGAACCGCTGCCCGAAGGC
GAGCGCCCGAGCGCCGTTCGACGACGCCCGACACCACCGGCGTCCTGGA
ATATCAGCTCGTCCTGTCCGACCCGAACGGCATCGAAGCGGAAGCCATTC
GCGCGCTGCGCACCCGCATCATGGCGCAGCACCTGCGCGAGGGCCGCCGC
GCCCTGGCGATCTGCGGCGCCTCGGCCGGCGTCGGCTGCAGCTTCACCGC
CGCCAACCTCGCGACGGCGCTGGCGCAGATCGGCATCAAGACCGCGCTGG
TCGATGCCAATCTGCGCGACCCGAGCATCGGCAGCGCCTTCAACATCGCC
GCCGACAAGCCGGGCCTCGCCGACTATCTCGCCTCGGGCGATATCGACCT
CGCCTCGATCATCCACCCGACCAAGCTGGACCAGCTGTCGGTGATCCATG
CCGGGCATGTCGAGCACAGCCCGCAGGAACTGCTGTCCTCCGAGCAGTTC
CACGACCTCGTGACGCAGCTGCTGCGCGAGTTCGACATCACGATCTTCGA
CACCACGGCCGCGAACACCTGCGCCGATGCGCAGCGCGTCGCACATGTCG
CCGGCTATGCGATCATCGTGGGCGGAAGGATTCGAGCTACATCCGCGAC
GTCAACACGCTCACCCGCACGCTGCGGTCGGACCGCACCAACGTCATCGG
CTGCGTCCTGAACGGCTATTGAATTGGATTCCATGACCGCGACTGCGCTG
GAGCGGCAGCAAGGACGGCGACAGGGGGCTATTGGCTCGCGGTCGCCGG
CCTTGCGGCACTCGCCATTCCCACTTTCGTCACGCTCGGCCGCGAAACCT
GGAGCGCCGAAGGTGGCGTGCAGGGCCGATCGTGCTGGCGACCGGCGCC
TGGATGCTGGCGCGGCAACGCGACAGCCTCGTGGCGCTCCGGCGCCCCGG
CAATCTGGCGCTGGGCGCATTGTGCCTGTTGCTGGCGCTGGGCATCTACA
CCGTCGGTCGCGTGTTCGACTTCATCAGCATCGAGACGTTCGGGCTGGTC
```

FIGURE 14g

```
GCGACCTTCGTGGCGGCTGCGTTCCTCTATTTCGGCGGCCGGGCGCTGCG
CGCTGCGTGGTTCCCGACCTTGTGGCTGTTCTTCCTCGTGCCGCCGCCGG
GCTGGATCGTCGATCGCGTCACCGCGCCGCTCAAGGAGTTCGTCTCCTAT
GCCGCCACCGGCTTCCTGTCCTGGCTGGACTATCCGATCCTGCGCCAGGG
CGTGACGCTGTTCGTCGGCCCCTATCAGCTGCTGGTCGAGGATGCCTGTT
CGGGGCTGCGCTCGCTCTCCAGCCTCGTCGTCGTCACGCTGCTGTACATC
TACATCAAGAACAAGCCGTCCTGGCGCTACGCGCTGTTCATCGCCGCGCT
GGTGATCCCGGTCGCGGTGATCACCAACATCCTGCGCATCGTCATCCTCG
TGCTGATCACCTATCATATGGGCGACGAGGCCGCGCAGAGCTTCCTCCAC
GTCTCCACCGGCATGGTGATGTTCGTGGTCGCGCTGCTCTGCATCTTCGC
CATCGACTGGGTGGTCGAACAGCTCTTCACACGGCGCCGGAGGCCCCATG
TTCAACCGGCGTGACCTGCTGATCGGCGCGGGCTGCTTCGCCGCCGCCGG
CGCCTCGCTCGGCCTCAAGCCGCACCGTCGCATGGACCTGCTCGGTGCGA
CCAAGCTCGATGCGCTGATGCCCAAGGCATTTGGCGGCTGGAAGGCCGAG
GATACCGGTGCGCTGATCGCCCCGCGCGCGAAGGCAGCCTGGAAGACAA
GCTGTACAACCAGGTGGTCGCCCGTGCCTTTTCGCGCGCCGACGGCACCC
AGGTGATGCTGCTGATCGCCTATGGCAACGCCCAGACGGATCTGCTGCAG
CTCCACCGACCGGAAGTCTGCTACCCGTTCTTCGGCTTCACCGTGGTCGA
GAGCCACGAGCAGATCATCCCGGTGACGCCGCAGGTGACGATTCCCGGAC
GGGCGCTGACCGCGACCAACTTCAACCGCACCGAGCAGATCCTCTACTGG
ACCCGCGTGGGCGAATATCTGCCGCAGAACGGCAACGAGCAGCTGTTCGC
CCGCCTCAAGAGCCAGCTCCAGGGCTGGATCGTCGACGGGGTGCTGGTCC
GCATCTCGACTGTGACGGCGGAAGCCAAGGACGGCCTCAACGCCAATCTC
GATTTCGCGCGCGAGCTGGTGAAGACGCTCGATCCGCGCGTGCTGCGCCC
GTTGCTCGGCACGCAGGTAACGCGCGACCTGGCGCCGCGCGCCTGAACGA
AAAAGGGGCGGCGCAGACCGCCGCCCCTCCCTCTCCTTCTCGTCGCGTAC
CCGCGCTCAGCGCTCGTGCAGCGCGTCGCTGCCGGTTTCGAGCATCGGGC
CGACGAGATAGCTCAGCAATGTCCGCTTGCCGGTGACGATGTCGGCACTG
GCGATCATGCCCGGCCGCAGCGGCACGTGCCCGCCATTGGCGATGACATA
GCCGCGGTCCAGTGCGATCCGCGCCTTGTAGACCGGCGGCTGGCCCTCCT
TCACCTGCACCGCCTCGGGCGCGATGCCCACCACCGTGCCGGGGATCATG
CCATAGCGGGTGTGCGGGAACGCCTGCAGCTTCACCTTTACCGGCATGCC
GGTGCGCACGAAGCCGATATCGCTGTTGTCCACCATCACCTCGGCCTCGA
GCCGGGCATTGTCCGGCACCAGCGACAGCAGCGGCTTGGCGCCCTCCACC
ACGCCGCCTTCGGTGTGGACCTGCAGCTGCGAGACCGTGCCGCTGACCGG
CGCGCGCAGTTCGCGGAACGAACTGCGCAGATTCGCCTTGGCGACTTCCT
CGCTGCGCGCCCGCACGTCGTCCTGCGCCTTCACCAGATCCTGCAACACC
TGCGCGCGCGCCTCCTCGCGCGTCCTGATCGACATGCTGCTGGCACTGCG
CGACTGCTGACCAAGCTTGGCCACCGTCGCCCGCGCCGCGGTGAGGTCCT
GCCGTTCGGAAATGAGCTGGCGGCGCATCTCGACCACGCGCAGCTTCGAG
ACATAGCCCTTGGCGGCCATCGCCTCGTTCGCGGCGATCTGCTGCTCGAG
CAGCGGCAGCGATTGTTCCAGCTTGCGAACCTGCGCCTGTGCCTCGGCCG
AGGCGGAAGCGGCGGCACCGCTGTCCGATCGGCCGCCGGCAAGCATCGCC
TCGATCTGGCCGAGCCGCGCGCGTGCGAGGCCGCGATGCGTCTCGACCTC
CGCGGCGCCTGCGGCGGCGGGCGCGGCGAAGCGGAAGCCCTTTCCGTCCA
GCGCGTCGATGATCGCCTGGTTGCGCGCGGCATCGAGCTGGGCGCTGAGC
AGCGCCACGCGCGCCTGCGCGGCTTCGGCTGCCGACATGGTGGGATCGAG
CGTGATCAGCACCTGGCCCTTCTGAACCTTCTGCCCCTCGCCCACCAGAA
TGCGCCGGACGATACCGCTTTCGGGGACTGCACGATCTTGGTCTCGCCG
ATCGGGGCGATGCGGCCCTGCGTCGGCGCCACCACTTCCACGCGGCCGAT
TGCCAGCCAGGCGGTGGTGATCGCCAGCCCCGCCACCATCACCCGGCCGG
TGAGGCGCGCGGTGGGCGACACCGGACGTTCGATGATCTCGAGCGCGGCC
GGCAGGAATTCGGTATCATAGGCATCGGCGCGAGCGGGCAGCACGGTGCC
GCGCATGCGGGCGATCGGGCCGCCGCGGCCGATCGGAACAACGGCGTTCA
```

FIGURE 14h

```
TGCGGCAATCTCCCCATATCCGCTTTGGCGGCGGTGCAGGTCGGCATAGC
GGCCGCCCAAGCGTAGCAGTTCGTCATGCCGGCCGCTCTCGACGATGCGG
CCCTGCTCCAGCGTGATGATCCGATCGCAGGCGCGTACCGCGGACAGGCG
GTGGGCGATGATCACCAGCGTGCGGCCCGCCGAGATGGCGCGCAGATTGT
TCTGGATCAGCTCCTCGCTCTCGGCATCCAGCGCGGAGGTCGCCTCGTCG
AACACCAGGATGCGCGGATTGCCGACCAGCGCGCGGGCGATAGCGAGCCG
CTGGCGCTGGCCGCCCGACAGGTTGACGCCGCGCTCGACGATCTCGGTGT
CATAGCCGCGCGGCTGACGCAGGATGAAGTCATGCGCACCCGCCAGCGTC
GCCGCCGCCACGACATGCTCGAACGGCATCGCCGGGTTGGACAGCGCAAT
GTTCTCGCGGATCGAGCGGCTGAACAGCAGATTTTCCTGCAGCACGACGC
CGATCTGCCGGCGCAGCCAGGCGGGATCGAGCTGGGCCACATCCACCTCG
TCGACCAGCACGCGGCCCAGATCGGGGGTGTTGAGGCGCTGCAGCAGCTT
GGCCAGCGTCGACTTGCCCGACCCCGAGGAGCCGACGATGCCGAGCGACG
TGCCGGCGGGGATGTCGAGCGTGATGTCGCTCAGCACCGGCGGCTGGTCC
TCGGCATAGCGGAAGGTCACGTTTTCGAAGCGGATCGCGCCGCGCAGCAC
CGGCAGCGTCGCGGCGGAGGCCGGCCGCGGCTCCACCGGATGGTTGAGCA
CGTCGCCGAGGCGCTCGATCGCGATGCGGACCTGCTGGAAGTCCTGCCAC
AGCTGGGCCATGCGGATCACGGGGCCGGAAACGCGCTGGGCGAACATGTT
GAACGCCACGAGCGCGCCGACGCTCATCGCGCCACCGATCACGGCCTTGG
CGCCGAAGAACAGGATCGCCGCGAAGCTCAGCTTGGAGATCAGCTCGATC
GCCTGGCTGCCGGTGTTGGCGACGTTGATCAGCCGCTGCGACGAGGCGGT
ATAGGCGGCGAGCTGACGTTCCAGCGATTCTGCCAGTGCGGTTCGACTG
CGGTCGCCTTGATGGTGTGGATGCCGGAGACGCTCTCGACGAGCAGCGCG
TTGCTGGCGGAGCTCTTCTCGAACTTGTCCTCGACACGCGTGCGCAGCGG
GCCCGCGACGCCGAACGAGACCATCGCATAGGCGACCAGCGACACGATCA
CGACGCCGAACAGCATCGGCGAGTAGAACAGCATCGCGCCGAGGAACACG
ACCGTGAACAGCGGATCGACCATCACCGTCAGCGACGCATTGGTGAGGAA
TTCCCGGATGGTCTCGAGCTGGCGGACCCGGGTGACGGTGTCGCCCACCC
GCCGCTTTTCGAAATAGCCGAGCGGCAGCGCCAGCAGATGGTGGAACAGC
CGCGCGCCCAGCTCGACGTCGATCTTCTGCGTCGTCTCGGTGAACAGGCG
CGTGCGGATCCAGCCCAGCGCCACCTCCCAGACCGACACGGCCAGGAAGG
CGAAGGCGAGCACGCTCAGCGTGCTCATGCTGTTGTGGACCAGCACCTTG
TCGATCACGCTCTGGAAGAGCAGCGGCGCCGCGAGGCCGAGCAGGTTGAG
CGCCAGGGTGATGCCCAGCACCTCGAGAAACAGCCTGCGATACCGCTGGA
ACTGTGCGGCGAACCAGGAGAAACCGAATCGCAGCGCCTGGCCGGCCACG
GCGCGCGTCGTCAGCAGCACGAGCGTGCCGGACCACAGCGCATCCAGCCC
CTCGCGGTCGACCTGTTCGGGGGCGTGGCCGGGACGCTGGATGATCACGC
CATGCTCGGTCAGGCCACCGATCACGAACCAGCCCTCCGGGCCGTCGGCG
ATGGCCGGCAGCGGCTGGCGGGCCAGACCGCCGCGCGGCACGTCCACCGC
CTTGGCGCGCACGCCCTGCTGGCGCTTGGCGAGCAGGATCAGGTCGTCGA
CGCTGGCACCCTCGGCATGGCCCAGCATGTGCCGCAGCTGTTCGGGGGTG
ACGGCGATGTTGTGGACGCCGAGCAGCAGCGACAGCGCCACAAGCCCGGA
TTCGCGCAATTCGCCCTCGCGCTCGGCGGCAGCCTGGGCGGCGAACGCGC
CCTGGAGCTGTGCCTGCATCTCGTCGCGTGTCATTCCGGTACTCTGCCTC
CATGGCGCTACTGATCGCAGCCATGATGAACGAGCTCGGTAAAGACTCGC
TTAAGCCAGATTTTTCTGTGGTTTATACCTATTGCCGGGGATGCCGGACC
GGACCGGATCGGCAGACGGCAGCCTGCGTTAGTCGGGCCTTAAAGCGTTG
CCGCTAGCACAAGGACAAGAATTTTATCGGAGAGGGTCGGGAACCATGCC
CACGCATGAAGGTTGCAGCGCAGCAATATCGACGGATCGCCTCGGAGCCC
GAATGCTGCATCCGCGAAGTGACTTTCGCCAAAGCAGCTATAGGATGGCC
CGGGGCTTGATTGCCGCCGTGCGATCAGCATAAGCGATCCATGGTCGCCA
AAATCTGTCATCCTTGGTAACAATCATGCAGCCGCTAAGGAAGATGTGCA
CGTCTGACGATGCTTTCTTCCGCACCCCATGCGCCGCTGACTCTGGTAGA
TTGACCGTGGCCTCCATTGCTCATCGTCTCGAAAAAGGACCCTCTGGTCG
```

FIGURE 14i

```
CCGCGCGGACTTCCGGGAATCGATTTGTCCCGTTATAGTGCAATGCAACA
GGCCGAATCGGCCGCTGTCAGCGTGCACAATCCGTTGAGGGAGCCCGACG
AGGCAATGAACGCTTTTGAAGCACAGCGCGCCTTTGAGGAGCAGCTCCGG
GCCCATGCCCGTTCTGCCCCAGCGCCGCACCCATGCTGCGACGTTCCAC
GATCCGCATGATCCTCTACACCGAATTGCTGTTGCTCGACAGCATCGCAA
TTCTACTGGGGTTCTACATCGCGGCCTGCTCGCGCGACGGCAACTGGCTG
TCCCTTGCGGGCGTCAATGTCGGCATCTTCCTCCTGCCGATCACGCTCGG
CACCGCGCTCGCCAGCGGCACCTATTCGCTGAGCTGCCTGCGCTACCCGG
TCAGCGGGGTGAAGAGCATCTTCTCGGCGTTCTTCTTCTCGGTGTTCATC
GTGCTGCTGGGCAGCTACCTGCTCACCGCGGAGCTGCCGCTGTCGCGCCT
GCAGCTCGGCGAGGGCGTGCTCCTGGCGCTCAGCCTGGTGACGATCTGCC
GCCTTGGCTTCCGCTGGCACGTTCGTGCGCTGACACGCGGCACGCTGCTC
GACGAGCTGGTGATCGTCGACGGCGTTGCCCTGGAGGTCGCGAGCGGCGC
GGTCGCGCTCGATGCGCGCATCATCAACCTCACGCCCAACCCGCGCGATC
CGCAGATGCTGCATCGCCTCGGCACCACCGTGGTGGGCTTCGACCGGGTC
GTCGTCGCCTGCACCGAGGAGCACCGGGCAGTATGGGCGCTGCTGCTCAA
GGGCATGAACATCAAGGGCGAGATCCTCGTCCCCCAGTTCAACGCGCTGG
GCGCGATCGGCGTCGACTCCTATGAGGGCAAGGACACGCTGGTCGTGTCC
CAGGGCCCGCTCAACATGCCGAACCGCGCAAAGAAGCGGGCGCTCGATCT
GCTCATCACCGTCCCCGCGCTGGTCGCGCTGGCGCCGCTGATGATCGTGG
TCGCGATCCTGATCAAGCTGGAGAGCCCCGGCCCCGTCTTCTTCGCACAG
GACCGCGTCGGCCGCGGCAACCGACTGTTCAAGATCCTCAAGTTCCGCTC
GATGCGCGTTGCGCTCTGCGATGCGAACGGCAACGTCTCGGCCAGCCGCG
ATGACGATCGCATCACCAAGGTAGGCCGGATCATCCGCAAGACCAGCATC
GACGAGCTGCCGCAGCTGCTCAACGTGCTGCGCGGCGACATGAGCGTCGT
CGGCCCGCGCCCGCACGCACTCGGGTCGCGCGCCGCCAACCATCTCTTCT
GGGAAATCGACGAGCGCTACTGGCACCGCCACACGCTCAAGCCGGGCATG
ACGGGCCTCGCGCAGATCCGCGGCTTCGCGGCGCGACCGATCGCCGCGT
CGATCTCACCAATCGCCTGCAGGCGGACATGGAGTATATCGACGGCTGGG
ACATCTGGCGGGACGTCACCATCCTGTTCAAGACGCTGCGCGTGATCGTG
CACTCCAACGCCTTCTGATCGCGGAGGGGAGCAACGCGAGCACCGCTTGG
TGCAAGAGCATTGACATCCGCCCTGCTTCTGCATTTGTCATTTTATCATT
GTCGTTGCGGGCCCGCCCGCGCCATGGGGGATTTTGAATGAAGGGTATCA
TCCTTGCGGGGGGCAGCGGCACGCGCCTCTACCCCGCAACGCTGTCGATC
TCGAAGCAGCTGCTTCCGTCTATGACAAGCCGATGATCTTCTACCCCCT
GTCGGTGCTGATGCTCACGGGTATCCGGGACATCCTGATCATCTCCACCC
CGCGCGACCTGCCGATGTTCCAGGCGCTGCTCGGCGACGGTTCGGCATTC
GGCATCAACCTGAGCTATGCCGAACAGCCTTCGCCCAACGGCCTTGCGGA
AGCCTTCATCATCGGCGCCGATTTCGTCGGCAACGATCCCAGCGCGCTGA
TCCTCGGCGACAACATCTATCACGGTGAAAAGATGGGCGAGCGCTGCCAG
GCAGCTGCGGCCCAGGCATCGCAGGCGGCGCGAACGTGTTCGCCTATCA
TGTCGACGATCCCGAGCGCTACGGCGTGGTCGCGTTCGATCCGGAGACGG
GCGTCGCTACCAGCGTCGAGGAAAAGCCGGCCAACCCCAAGTCCAATTGG
GCGATCACCGGGCTTTATTTCTACGACAAGGACGTGGTCGACATCGCCAA
GTCGATCCAGCCCTCGGCGCGCGGCGAACTCGAGATCACCGACGTCAACC
GCATCTACATGGAGCGCGGCGACCTCCACATCACCGGCTCGGTCGCGGC
TATGCCTGGCTCGACACCGGCACGCATGACAGCCTGCACGAGGCCGGCTC
GTTCGTCCGCACGCTGGAGCACCGCACCGGCGTGAAGATCGCCTGCCCGG
AGGAAATCGCCTTCGAGAGCGGCTGGCTGGGCGCCGACGATCTGCTCAAG
CGCGCCGCCGGCCTCGGCAAGACGGGGTATGCCGCCTATCTGCGCAAGCT
GGTAGCCGCGGCATGACCCAGGTGCATCACCACGCGCTATCGGGCGTCAT
CGAGTTCACCCCGCCCAAGTACGGCGATCACCGCGGCTTCTTCTCCGAGG
TGTTCAAGCAGTCCACGCTCGACGCCGAAGGCGTCGAGGCGCGGTGGGTG
CAGGACAATCAGAGCTTCTCGGCCGCACCGGGCACGATCCGCGGACTGCA
```

FIGURE 14j

```
CCTGCAGGCGCCGCCCTTCGCCCAGGCCAAGCTGGTGCGCGTGCTGCGCG
GCGCGATCTACGACGTCGCGGTCGACATTCGCCGCGGCTCGCCCACATAC
GGCCAGTGGGTCGGCGTCGAGCTTTCGGCGGACAAGTGGAACCAGCTGCT
GGTGCCGGCCGGCTATGCGCATGGCTTCATGACGCTCGTCCCGGATTGCG
AGATCCTCTACAAGGTCAGCGCCAAATATTCGAAGGAATCGGAGATGGCG
ATCCGCTGGGATGATCCCGATCTCGCCATCACCTGGCCGGACATCGGCGT
CGAGCCGGTGCTCTCCGAAAAGGACGCGGTCGCTACCCCGTTCGCCGAAT
TCAACACCCCCTTCTTCTATCAGGGCTGATCCATGCAGCAGACCTTCCTC
GTTACCGGCGGCGCCGGCTTCATCGGCTCGGCAGTGGTACGCCACCTCGT
TCGCCAGGGCGCGCGCGTCATCAATCTCGACAAGCTCACCTATGCGGGCA
ACCCGGCCTCGCTGACCGCGATCGAGAACGCCCCCAACTACCGCTTCGTC
CACGCCGATATCGCCGACACCGCGACGATCCTGCCGCTGCTGCGCGAAGA
GCAGGTCGACGTGGTGATGCACCTCGCCGCCGAGAGCCATGTCGATCGCT
CGATCGACGGCCCGGGCGAGTTCATCGAGACCAACGTCGTCGGCACCTTC
AAGCTGCTCCAGGCGGCGCTGCAATATTGGCGCGAGCTGGAAGGGGAGAA
GCGCGAGGCTTTCCGCTTCCACCACATTTCCACCGACGAGGTGTTCGGCG
ACCTGCCGTTCGACAGCGGCATCTTCACCGAAGAGACGCCCTATGATCCC
TCCTCGCCCTATTCGGCGTCGAAGGCGGCCAGCGACCATCTGGTCCGCGC
CTGGGGTCACACCTATGGCCTGCCCGTGGTGCTGTCGAACTGCTCGAACA
ATTACGGGCCGTTCCACTTCCCCGAGAAGCTGATCCCGCTGACCATCCTC
AACGCGCTGGAAGGCAAGCCCCTGCCCGTCTACGGCAAGGGCGAGAATAT
CCGCGACTGGCTGTACGTCGACGATCACGCCAAGGCGCTGGCGACGATCG
CCACGACCGGCAAGGTCGGCCAGAGCTACAATGTCGGCGGCCGCAACGAG
CGCACCAACCTGCAGGTCGTCGAGACGATCTGCGACCTGCTCGATCAGCG
CATTCCGCTGAAGGATGGCAAGAAGCGCCGCGAGCTGATCACCTTCGTCA
CCGATCGCCCCGGCCATGACCGCCGCTACGCGATCGACGCGACCAAGCTC
GAGACCGAACTGGGCTGGAAGGCCGAGGAGAATTTCGACACCGGCATCGC
CGCGACGATCGACTGGTATCTCGAGAATGAATGGTGGTGGGGTCCGATCC
GCTCCGGCAAATATGCCGGCGAGCGGTTGGGGCAGACCGCCTGATGCGCA
TCCTCGTCACCGGGCATGACGGCCAGGTCGCCCAGGCGCTGGGCGAACAG
GCGGAGGGCCATGAGCTGATCTTCACCAGCTATCCCGAGTTCGATCTCTC
CAAGCCGGAGACGATCGAGGCGGCGGTGGCGAAGATCCAGCCCGAGCTGA
TCGTGTCGGCGGCTGCGTATACGGCGGTCGACAAGTCCGAGAGCGAGCCC
GAGCTCGCCATGGCGATCAACGGCGACGGCCCCGGCGTACTGGCGCGCGC
GGGCGCGAAGATCGGCGCGCCGATCATCCATCTGTCGACCGACTATGTGT
TCGACGGCAGCCTGGACCGCCCGTGGCGCGAAGACGACCCCACCGGTCCG
CTCGGCGTCTATGGCGCCACCAAGCTGGCCGGCGAGCAAGCGGTGCAGGC
CTCGGGCGCGACCAACGCGGTGATCCGGCTCGCCTGGGTCTACAGCCCGT
TCGGCAACAACTTCGTCAAGACGATGCTGCGCCTCGCCGAGACGCGGGAC
ACGCTGAACGTGGTCGAGGACCAGCAGGGCTGCCCGAGCTCGGCGCTGGA
CATCGCCACGGCGATCCTCAAGGTCGTCGGCCACTGGCAGCAGAACGGCG
CCACCAGCGGCCTGTATCACTTCACCGGATCGGGCGAGACCAACTGGGCC
GACTTCGCGCGCGCGATCTTCGCGGAAAGCGCCAAGCACGGCGGTCCGAC
CGCCGAGGTGACCGGCATTCCGACCTCCGGCTACCCCACCCCGGCGAAGC
GCCCGGCCAATTCGCGGCTCAATTGCGACAAGTTCGCCGAAACCTTCGGC
TATCGTGCACCCGCCTGGCAGGACTCGGTGGCGGAAGTGGTAGGCCGCCT
CCTGGCATAAAATGCCCGGCCCGACCCTGTGCGCGGCGGGGTGGCTGCGC
ACTCCGGTCGGGTTTCATCGACATCGCCGGCTGCGGGGAGCATCACCGAT
GCTCCCCGATCAGCGCCAGGCCGTCACTTCCTGAACGGCGCGACCAGGGG
CTTGATCGTCTTGAACACGGCCTCACGCAGCGTCCGCACGGGCGCGGCGA
CGAGGTGATCGAACGCGAGCGTCATCCCGCTCACCCGCTGGGGTGCGACG
TCGCTGCGGATCTTGAACGATTCGACCACCTCGATATCGGAAACCAGCCG
CCCCTTGATGCGGTTGATGACATTCTCGCCATGCACCACCTGCAGCCATA
CCGGCCGCCCGGCGACCTGGGTGATCTTCCACTTCTGGCCCAGCTCATGA
```

FIGURE 14k

```
TGGGGCTTGGCCCAGATCGTCTCGACGCTGGCGAGATCGCGCTCGACCAG
CGAGGTGAACGGATTGCTGTGGTCCGCAGCGGTGTAGAGCCGGCCCTGGC
GCATCGCGATGCCCTGGGTGAAGTTCAGCACCGTCTGTGCCGGCGCATCC
TTCGCCGCGGCCTGCACCCGTGCCACGAAGTCGTTCGAAAGCGCGTCGTC
ATTGTCCAGCCGCGTGGTGACGATCAGCTGCTCGCCGGGCGTCGCCAGCG
CCTTCACGTCGTCCGCGATCATCGCCTTGTCGAACATCGCGACGTAGCGC
GGCGTGAAGTTGTAGATCTGCCGATCGCGCTCGATCCGCTCGCGGAACTC
GGCGGGGGTGTCCTTGTCGAAGTAGATGAGCCAGTGGAAGTTGCGCTCGG
TCTGGCCCGCGATGCTCGGCAGGCAGAACTGCTCGAACAGCCCGAAACGG
CGGTCGAGCCAACCCGGCGAATTGCGGATCGCCACCTCGCGGCCCGGGCT
GGCGATGTTGAAGCGCGTCAGGATCACGTGAAGCATCGGTTCGATCAGCC
CCGGTCTAGCAAAACGAAGAAAGCCCGGCCGCTACAACGGCCTTGTTCGA
ACAACGCGCAAGAAACAGGGTACACGCGAACGGCACGTTCGTCTTCGCCC
ACCCCGCTGGTTGCCGCCATTCCACGAACGGTTACGGGATATTCCGGAA
CTGGGCAACCGGGGATTGCTGCACTGCGCAATGACACGCGGCCGGAATGA
CAAACGGCTTGCCGCCCGCGCCCCCGCGCCTAACCCTCCGCCCGTGCCC
GACGCCCGTCCCGATCGCATTGCCACCGGCCTGGCGCTTCGCCTGTTCGC
CATTGCCTGCCTGTCGACCATGTCGGCGCTCATCAAGATGTCGGAACTGC
GCGGCGCCTCGCTGATCGAGACGATGTTCCACCGCCAGCTCTGGGCGGTG
CCGCTGGTCACCTTGTGGGTGGTGATGGGCCCGGGGCTCAAGTCGCTCAA
GACGCAGCGCTTCGGCGCGCATGTCTGGCGCACCGCGGTGGGCCTCACCG
GCATGATCTTCACCTTCGGCGCGGTGATCCTGCTGCCCCTGGCCGAGGCG
CAGACCTTCCAGTTCACCGTGCCCATCTTCGCCACGCTGCTCGGCGCGCT
GATCCTCGGCGAGCCGACCGGCCGGCATCGCTGGGGCGCAGTGATCGTCG
GCTTCCTCGGCGTGCTGATCGTCGTCCAGCCGGGCCGGGAAGCCATTCCG
ATCTTCGGCGCCTTCGTCGGGCTGATGGCGGCGTTGTTCGTCGCCATCGT
CGCGATCACGCTGCGGCAGATCACCCGCACCGAAAGCGCCGGCACCACCG
TCTTCTGGTTCTCGCTGCTCTCGGTGCCCGTGCTCGGCGCCATCTACGCG
TTCAACTTCCGTCCGCACGATGCCGAGACCTGGGCGATCCTCATCGCCAC
AGGACTGGTGGGCGGCGTCGGCCAGCTGGCGCTGACCGGTGCGATGCGCT
TCGCCCCCGTCTCGGCGGTGGTACCGATGGACTATTCGGGGCTGATCTGG
GCGACGCTCTACGGCTGGCTGCTGTTCGACGTGTTCCCGACCTTCTCGAC
CTGGCTCGGTGCGCCGGTGATCATCGCCAGCGGGCTCTACATCGTCTATC
GCGAGCAGAAGCTGGCCCGCGGCCAGGCTAGCTACGCCGAAACGCCACTA
TGAGGTTGTTGGCGGGCATCGCCACCCGCCGATCGAACACCAGGCCTTGC
GCCCCGCCGCCGCGATCACCTCGTCCAGCAAGCGCAGCCCCCAGGCAGG
ATCC
```

DNA SEGMENTS AND METHODS FOR INCREASING POLYSACCHARIDE PRODUCTION

CROSS-REFERENCE TO RELATED APPLICATIONS

The present application is a continuation-in-part of copending application Ser. No. 08/377,440, filed Jan. 24, 1995, the contents of which are incorporated herein by reference.

FIELD OF THE INVENTION

The present invention relates to DNA sequences and fragments, thereof, which are involved in the biosynthetic production of sphingan polysaccharides of and isolated from Sphingomonas sp. The isolated DNA fragments may be inserted into the same or different strains of Sphingomonas sp. or related bacteria in multiple copies to increase polysaccharide, preferably sphingan production. The engineered bacteria containing exogenous DNA produce significantly greater amounts of polysaccharide compared to non-engineered bacteria under identical fermentation conditions. The present invention also relates to methods of engineering strains of Sphingomonas sp. and other related bacteria to be hyperproducers of polysaccharide as well as the engineered bacteria. Methods of identifying and isolating DNA sequences useful for increasing the production of sphingan polysaccharides in Sphingomonas sp. are also described.

BACKGROUND OF THE INVENTION

A number of microorganisms produce extracellular polysaccharides, also known as exopolysaccharides or EPS. Of the exopolysaccharides, xanthan gum and a group of polysaccharides known as "sphingans" are included. "Sphingans" are produced by gram-negative bacteria of the genus Sphingomonas.

The "sphingans" are capsular polysaccharides which have similar but not identical structures and are secreted by members of the genus Sphingomonas (Pollock, T. J. 1993, *J. Gen. Microbiol.* 139:1939–1945). The various sphingans have different side groups and either L-rhamnose or L-mannose is found at one position in the backbone. L-mannose itself is exceedingly rare in nature. Aqueous solutions of the polymers have unique and useful rheological properties (See, Moorhouse, R. 1987, "Structure/property relationships of a family of microbial polysaccharides," p. 187–206. In M. Yalpani (ed.), *Industrial polysaccharides: genetic engineering, structure/property relations and applications.* Elsevier Science Publishers B. V., Amsterdam). It is not clear how the structural variations in the polymers give rise to distinct rheological properties.

*Xanthomonas campestris* is a gram-negative bacterium which constitutively produces an exopolysaccharide, xanthan gum, in large amounts. Jeanes, et al., *J. Appl. Polymer Sci.,* 5, 519–526 (1961). The biosynthesis of xanthan gum has been studied in considerable detail because of its commercial importance. Recently, another bacterial exopolysaccharide, gellan, was developed as a gelling agent. It is a member of the sphingan family of polysaccharides which includes S-88 (See, Kang and Veeder, U.S. Pat. No. 4,535,153); welan (See, Kang and Veeder, U.S. Pat. No. 4,342,866); NW11 (See, Robison and Stipanovic, U.S. Pat. No. 4,874,044); rhamsan (See, Peik, et al., U.S. Pat. No. 4,401,760); S-198 (See, Peik, et al. U.S. Pat. No. 4,529,797); S-657 (See, Peik, et al., Eur. Patent Application 209277A1); and heteropolysaccharide-7 (See, Kang and McNeely, U.S. Pat. No. 4,342,866).

The above documents include several patents which relate to sphingan polysaccharide compositions. None of the patents remotely relates to the subject matter of the instant invention.

| Strain | Sphingan | Patent Number |
|---|---|---|
| ATCC 31461 S60 | gellan S-60 | 4,326,053 |
| ATCC31554 S88 | S-88 | 4,535,153 |
| ATCC31853 S198 | S-198 | 4,529,797 |
| ATCC21423 S7 | S-7 | 3,960,832 |
| ATCC31555 S130 | welan S-130 | 4,342,866 |
| ATCC31961 S194 | rhamsan S-194 | 4,401,760 |
| ATCC53159 S-657 | S-657 | EurApp 0209277 |
| ATCC53272 NW11 | NW-11 | 4,874,044 |

The chemical structures of the sphingan polysaccharides are all somewhat related. The main chain of each sphingan consists of a related sequence of four sugars-D-glucose, D-glucuronic acid, L-mannose and L-rhamnose. Polysaccharide members of the sphingan group are distinguishable from each other by virtue of the carbohydrates which comprise the polymer backbone (main chain) and the sidechains. The sphingan carbohydrates may contain carbohydrate side chains and acetyl or glycerate groups attached to carbohydrates on the polymer backbone.

Various sphingans are useful as specialty polymers and as additives in textile applications, foods, cosmetics, paper, paint, cements, e.g. as viscosity modifiers, in various other coating applications, and as adhesives and additives to petroleum products and specialty chemicals.

The focus of initial studies which culminated in the present invention was the first step in the biosynthesis of a representative sphingan polysaccharide, S-88. This sphingan is biosynthesized by Sphingomonas strain S88. Prior to the present invention, it was known that some, but not all, bacterial polysaccharide biosynthesis of other than sphingans utilize an isoprenylphosphate carrier. For example, in the case of xanthan gum biosynthesis by *X. campestris,* since the main chain of xanthan gum contains only glucose, the first synthetic step is likely the transfer of glucose-phosphate from UDP-glucose to a C55-isoprenylphosphate (IP) carrier. With cell-free incorporation assays, Ielpi, et al., *FEBS Lett.,* 130, 253 (1982) and *J. Bacteriol.,* 175, 2490 ((1993), confirmed that glucose, followed by a second glucose, and then mannose, glucuronic acid and mannose are added sequentially to carrier IP to assemble the repeating unit of xanthan gum. Quite similarly, the repeating subunit of colanic acid in *Escherichia coli* is assembled by first transferring glucose-P to IP. Johnson and Wilson, *J. Bacteriol.,* 129, 225 (1977). By contrast, in the case of the synthesis of succinoglycan polysaccharides by *Rhizobium meliloti,* a galactose-P is transferred first to IP. See, Tolnasky, et al., *J. Biol. Chem.,* 257, 6751 (1982). Isoprenyl carriers, however, are not involved in the synthesis of dextran or levan polysaccharides, and the role of isoprenyl carriers in alginate synthesis is unknown.

Prior to the investigation which led to the present invention, the importance of the role of the carrier in the complex kinetics of the biosynthesis of poly-saccharides was not known. In addition, it was not known what role the isoprenyl-phosphate carrier might play in the overall synthesis of sphingan polysaccharides in Sphingomonas bacteria.

Previously, genetic complementation tests have shown that a special class of mutations in *X. campestris* which are simultaneously Bac$^r$ and Gum$^-$ (bacitracin-resistant and xanthan gum-negative) map within the gumD gene which is required for transferring glucose-P from UDP-Glc to IP to give Glc-PPI. Pollock, et al., 1994, *J. Bacteriol*, vol. 176, pp. 6229–6237, Vanderslice, et al., "Genetic Engineering of polysaccharide structure in *Xanthomonas campestris*", p. 145–156, in V. Crescenzi, et al., *Biomedical and Biotechnological Advances in Industrial Polysaccharides*, Gordon and Breach Science Publishers, New York and N. E. Harding and Y. N. Patel, 1993, *Faseb Journal*, Vol. 7, Number 7. The latter reference discloses fragments of DNA that can restore synthesis of sphingan S-60 to non-producing mutants, but gives no indication of increased synthesis relative to the wild-type strain. Earlier experimentation also showed that the wild type gumD gene of *X. campestris* could restore synthesis of sphingans in analogous Bac$^r$ Sps$^-$ (sphingan polysaccharide-negative) mutants of Sphingomonas strains S88 and NW11. It was suggested that Bac$^r$ Sps$^-$ Sphingomonas mutants also appeared to be blocked in the transfer of glucose-P to IP.

OBJECTS OF THE INVENTION

It is an object of the present invention to provide DNA segments which are isolated from Sphingomonas sp. and may be used to enhance the production of sphingan polysaccharide in a number of microorganisms, and in particular, a number of strains of Sphingomonas.

It is also an object of the present invention to provide hyproducer strains of microorganisms, and in particular, a number of strains of Sphingomonas which will produce significantly more sphingan polysaccharide than non-engineered strains.

It is a further object of the present invention to provide a method for producing strains of microorganisms, and in particular, strains of Sphingomonas sp. which are hyperproducers of sphingan polysaccharide.

It is an additional object of the present invention to provide a method for isolating DNA segments which may be inserted into Sphingomonas strains so that the resulting engineered microorganism becomes a hyperproducer of sphingan polysaccharide.

These and/or other objectives of the present invention may be readily gleaned from the description of the invention which follows.

SUMMARY OF THE INVENTION

In the present invention, sequences of DNA as segments or fragments are isolated from sphingan-producing bacteria, generally from Sphingomonas strains. The resulting genetic material is cloned, incorporated as multiple copies into sphingan—producing or non-producing mutants of Sphingomonas or related bacteria. These DNA sequences have proved useful in restoring sphingan production in mutant bacteria which do not produce sphingan. Moreover, unexpectedly it has been found that the restoration of sphingan production in these mutants is coupled with production of amounts of sphingan which is significantly greater than the production expected from wild type strains which produce Sphingan.

We have unexpectedly discovered that DNA segments or fragments which are isolated from one Sphingomonas strain may be inserted as multiple copies into sphingan-producing or mutant non-producing bacteria of the same strain or different strains of Sphingomonas with the resultant engineered bacterium becoming a hyper-producer of sphingan. This is particularly unexpected inasmuch as the DNA segments or fragments isolated from, for example, Sphingomonas S60 and inserted into Sphingomonas S88 wild type or nonmucoid mutants will produce an engineered hyperproducer of S-88 sphingan which is generally not contaminated with S-60 sphingan. This complementation may be rather broadly applied across various strains of Sphingomonas (interstrain complementation) and even to the production of xanthan gum in Xanthomonas campestris (intergeneric complementation).

We have further discovered a method for producing engineered hyperproducing Sphingomonas bacteria which incorporate the DNA segments or fragments which have been isolated from sphingan-producing Sphingomonas strains. The DNA which is isolated from sphingan-producing bacteria is first cloned and then reinserted into sphingan-producing Sphingomonas strains or nonmucoid mutants derived from sphingan-producing strains.

The present invention also comprises engineered Sphingomonas bacteria into which the above-described isolated DNA segments or fragments have been inserted. These engineered bacteria contain multiple copies of isolated DNA segments or fragments according to the present invention. The engineered bacteria according to the present invention are hyperproducers of sphingan.

The DNA fragments according to the present invention may be isolated, recovered and cloned by techniques which are readily available in the art. Thereafter, the DNA is inserted into bacteria of the genus Sphingomonas in multiple copies, generally as extrachromosomal or plasmidic DNA. After insertion into the target bacteria, the production of sphingan is determined by fermenting the engineered bacteria under the same conditions as an identical concentration of non-engineered sphingan-producing bacteria of the same strain. Hyperproducers are determined by their increased sphingan production relative to the non-engineered sphingan-producing strain. DNA sequences for enhancing the production of sphingan polysaccharide from virtually any member of sphingan-producing Sphingomonas sp. bacteria may be readily determined using this procedure.

BRIEF DESCRIPTION OF THE DRAWINGS

FIG. 2 is a diagrammatic representation of restriction enzyme cleavage sites of a DNA segment (approximately 28 kbase units) isolated from chromosomal DNA of Sphingomonas strain S60 (ATCC accession number 31461). Restriction sites for this DNA sequence are shown in FIG. 2 as B, E and H sites. The sgeB region corresponds to the DNA sequence which codes for the protein SgeB.

FIG. 4 is a diagrammatic representation of the DNA sequence corresponding to the spsB gene, containing approximately 1950 base pairs, of Sphingomonas strain S88.

FIG. 5 is a diagrammatic representation of a deduced amino acid sequence of the SpsB protein of Sphingomonas strain S88.

FIG. 6 is a diagrammatic representation of the chemical structures of a number of sphingan polysaccharides representative of those produced by the present invention.

FIG. 12 shows the alignment of deduced amino acid sequences of SpsB and glycosyl-IP transferases. The numbers to the right are residue numbers for the rightmost amino acid on each line. In each set of lines the galactosyl-IP transferases are immediately above the sequence for SpsB, and the glucosyl-IP transferases are below. The gene products are identified on the right:: ExoYn, Rhizobium sp. NGR234 (Gray, et al., 1990, *J. Bacteriol.* 172:193); CpsD, S. agalactiae (Rubens, et al., 1993, *Mol. Microbiol.,* 8:843); RfbP, *S. enterica* LT2 (Jiang, et al., 1991, *Mol. Microbiol.,* 5:695); GumD, *X. campestris* B1459S-4L (Capage, et al., 1987, International Patent WO/05938); Pss4, *R. leguminosarum* bv. viciae strain VF39 (GenBank accession number M93042); and Pss2, *R. leguminosarum* bv. phaseoli (Borthakur, et al., 1988, *Mol. Gen. Genet.,* 213:155). Symbols: |, indicates identical amino acids for SpsB and galactosyl- or glucosyl-IP transferases, above or below respectively;:, indicates a conservative amino acid substitution based on the following groups of related amino acids: IFVWML, ST, QNED and HKR. Underlined sequences are contiguous segments of about 20 hydrophobic amino acids.

FIGS. 13a–13d show the alignments of the rhsA, B, C, and D gene products and dTDP-L-rhamnose biosynthetic enzymes from *S. enterica* (Jiiang, et al., 1991, *Molecular Microbiology,* 5: 695–713) and X. campestris (Koplin, et al., 1993, *J. Bacteriol.,* 175:7786–7792). FIGS. 13a, 13b, 13c and 13d show rhsA, rhsB, rhsC, and rhsD, respectively. The symbols are the same as in FIG. 12.

FIGS. 14a–14k a diagrammatic representation of the entire DNA sequence of the DNA segment isolated from chromosomal DNA of Sphingomonas strain S88 (ATCC accession number 31554) corresponding to the nucleotide sequence referred to in the restriction map of FIG. 8 (from base pair 0 to base pair 28,800). The entire sequence is presented, in order, in FIGS. 14a through 14k.

DETAILED DESCRIPTION OF THE INVENTION

Figure 1:
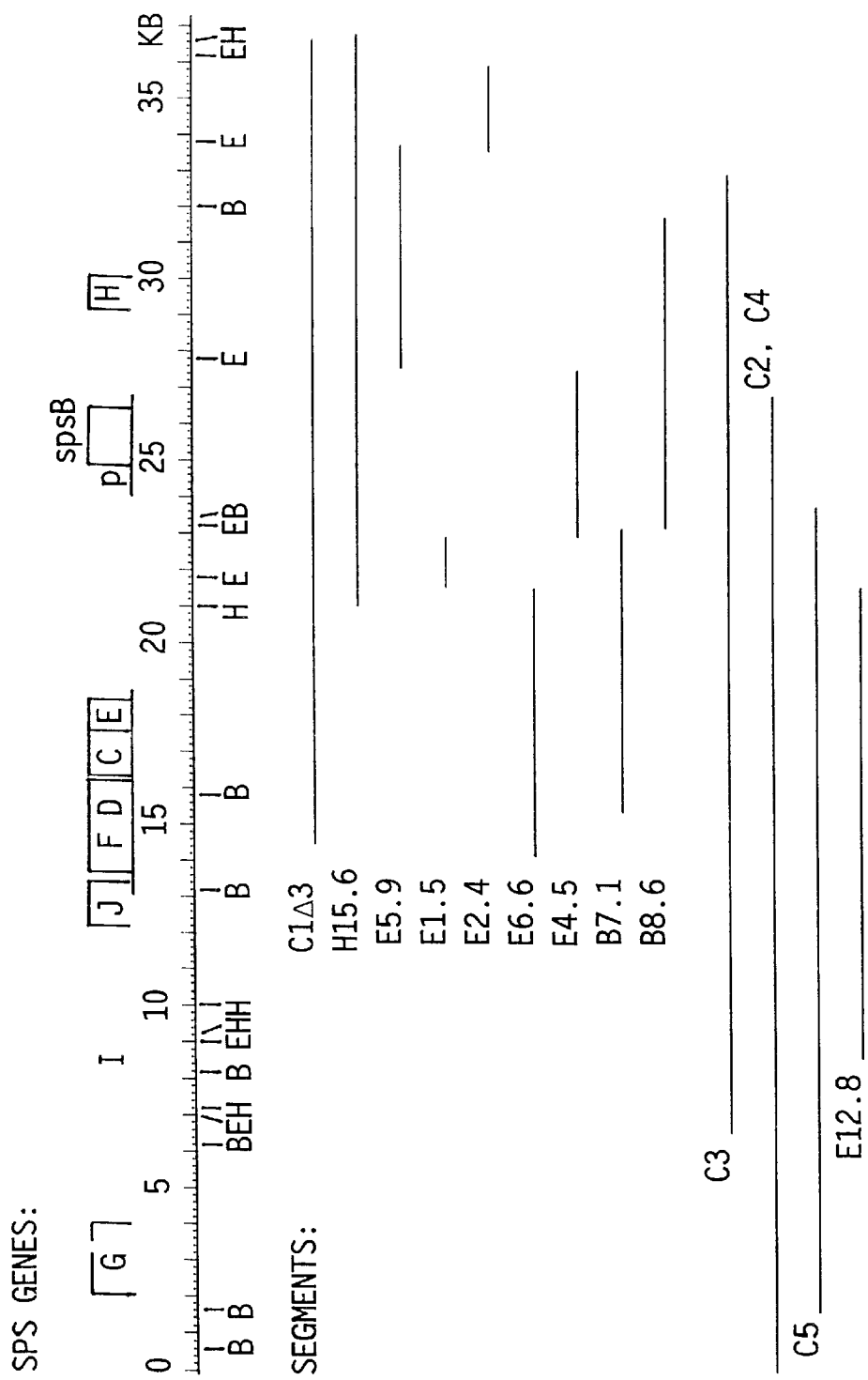
FIG. 1 is a diagrammatic representation of the restriction enzyme cleavage sites of a 34 kilobase nucleotide unit DNA segment isolated from chromosomal DNA of Sphingomonas strain S88 (ATCC accession number 31554). A number of the DNA sequences presented in FIG. 1 were inserted into Sphingomonas bacteria and examined for their ability to enhance sphingan production. Restriction sites for several enzymes are also shown in FIG. 1 (as well as FIGS. 2, 3, 8, 9 and 10): B (BamII), Bg (BglII), E (EcoRI), H (HindIII) and S (SalI). The spsB region, set forth in FIG. 1, corresponds to the DNA sequence which codes for the protein SpsB.

The following terms shall be used throughout the specification in connection with the present invention and have the meaning indicated:

1. The term "sphingan" is used throughout the specification to refer to a group of related but distinct exopolysaccharides secreted by members of the genus Sphingomonas (Pollock, *J. Gen. Microbiology* 139:1939–1945, 1993). The structures of the sphingans are all somewhat related. The main chain of each sphingan consists of a related sequence of four sugars- D-glucose, D-glucuronic acid, L-mannose and L-rhamnose. Polysaccharide members of the sphingan group are distinguishable from each other by virtue of the carbohydrates which comprise the polymer backbone and the sidechains. The sphingan polysaccharides may contain carbohydrate side chains and acetyl or pyruvyl groups attached to carbohydrates on the polymer backbone. See Mikolajczak, et al., *Appl. and Env. Microbiol.*, 60:402, (1994). The diagrammatic representation of the chemical structures of various sphingans produced using the DNA segments and fragments and general methods according to the present invention are generally set forth in FIG. 6. The structures of sphingans gellan (S-60), welan (S-130), rhamsan (S-194), S-88, NW-11, S-198 and S-657 are generally set forth in FIG. 6.

Typically, members of the sphingan polysaccharide family may be represented by the following general repeating chemical structure:

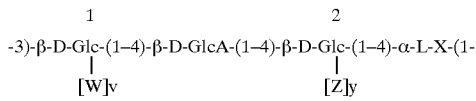

wherein Glc is glucose; GlcA is glucuronic acid; Rha is rhamnose; Man is mannose; X may be Rha or Man; Z is attached to Glc residue 2 and may be α-L-Rha-(1–6)-α-L-Rha, α-L-Man or α-L-Rha; W is attached to Glc residue number 1 and may be β-D-Glc-(1–6)-α-D-Glc or α-L-Rha, subscripts v and y may be 0, 0.33, 0.5, 0.67 or 1, and wherein the reducing end of the polymer is toward the X residue of the backbone. As used herein, the term "backbone" or "main chain" refers to that portion of the structure which excludes chains W and Z, i.e., when v and y are equal to 0. The "reducing end" of the polymer is that end of the polmer to which sugar units are added during biopolymerization.

Some members of the sphingan polysaccharide family are acetylated at various positions. However, the polysaccharides may be subjected to chemical deacylation in a conventional manner to remove the acyl groups. For example, gellan has the same carbohydrate backbone as welan (i.e., X=Rha), but lacks the side chain sugar (i.e., v=0 and y=0) and the glucose residue 1 is fully substituted with glycerate. The gellan subunit structure is also partially acetylated at glucose residue 1.

2. The term "Sphingomonas" is used throughout the specification to refer to strains of gram-negative bacteria from the genus Sphingomonas which produce exopolysaccharides or sphingans, as described above. A number of gram-negative bacteria from the genus Sphingomonas may be used in the present invention, either as a source of isolated DNA sequences which may be reinserted into other strains of sphingan- producing bacteria (preferably, gram-negative bacteria from the genus Sphingomonas) to produce sphingan hyperproducers according to the present invention, or as target bacteria for inserting exogenous DNA sequences to produce sphingan hyperproducers.

The sphingan-producing family of gram-negative bacteria was first identified as belonging to the genus Sphingomonas in 1993. See Pollock, *J. Gen. Microb.*, 139, 1939 (1993). It has yet to be established precisely to which species each strain belongs. The closest species to the sphingan-producing strains of Sphingomonas appears to be *Sphingomonas paucimobilis*. However, it is premature to refer to these strains as belonging to that species until a detailed and finalized taxonomic analysis is available. It is noted that the sphingan-producers of the genus Sphingomonas were initially classified into several different genera.

The currently recognized species of Sphingomonas include *S. paucimobilis, S. parapaucimobilis, S. adhaesiva, S. capsulata,* and *S. yanoikuyae.* See Yabuuchi, et al., *Microbiol. Immunol.*, 34, 99 (1990). Previously, these species of Sphingomonas had been incorrectly assigned to the genus Pseudomonas.

3. The terms "donor" and "recipient" are used to describe, respectively, bacteria from which DNA sequences are taken and into which DNA sequences are inserted or incorporated.

4. The term "strain" or "Sphingomonas strain" is used to describe gram-negative bacteria of the genus Sphingomonas which produce a particular sphingan exopolysaccharide (based upon chemical structure). For simplicity, the sphingan-producing strains of Sphingomonas are referred to by the sphingan polysaccharide produced by that strain. For example, Sphingomonas strain S88 produces sphingan polysaccharide S-88, Sphingomonas strain S60 produces sphingan polysaccharide S-60 (gellan), etc. Sphingomonas strains S88 (ATCC number 31554), S60 (ATCC number 31461), NW11 (ATCC number 53272), S130 (ATCC number 31555), S194 (ATCC number 31691), S198 (ATCC number 31853), 8657 (ATCC number 53159) and S7 (ATCC number 21423), among numerous others, are representative of strains which are useful in the present invention.

5. The term "hyperproducer" is used throughout the specification to describe engineered bacteria containing multiple copies of DNA segments or fragments isolated from the same strain or a different strain of sphingan-producing bacteria which produce significantly greater (at least about 5% more on a weight by weight basis) sphingan polysaccharide compared to non-engineered or wild type bacteria of the same strain as the engineered bacteria which are fermented under identical or substantially identical fermentation conditions.

6. The term "isolated" is used to describe DNA which has been removed from a microorganism and subjected to at least some degree of purification, i.e., one or more purification steps. Preferably, isolated DNA is prepared in substantially pure form, i.e., in a form which contains only minor quantities of contaminating material which will not affect the ability of the isolated DNA to be fragmented or segmented by restriction enzymes, cloned into multiple copies or inserted into plasmid vectors or otherwise inserted or incorporated into bacteria.

7. The term "DNA" or "chromosomal DNA" as used throughout the specification with respect to the DNA isolated from Sphingomonas describes DNA which is found in the chromosomes or endogenous plasmids of Sphingomonas sp., generally prior to isolation from the microorganism.

8. The term "sequence" is used to describe a specific segment of DNA which is either identified by its nucleotide units or by its pattern of sites for restriction enzyme cleavage, generally isolated from DNA of a sphingan-producing bacteria of the genus Sphingomonas using restriction enzymes, the resulting DNA sequence being inserted into a bacteria to produce a hyperproducer or alternatively subjected to further restriction to produce small portions or fragments of DNA smaller than said sequence. The term "portions" or "fragments" is used to describe DNA sequences which are generally smaller than DNA segments. Preferred DNA segments for use in the present invention are those which encode for glycosyl transferases (glucosyl, galactosyl, rhamnosyl and glucuronosyl transferases), glycosyl-IP transferases (including glucosyl-IP transferase, galactosyl-IP transferase enzymes, among others), rhamnose operon (synthesis of rhamnose precursor for incorporation into certain rhamnose-containing sphingans) and various proteins involved in the secretion of polysaccharides from bacteria.

9. The terms "inserted", "inserting", "incorporated" or "incorporating" are used throughout the specification to describe the process and outcome of transferring DNA segments isolated from the chromosomal DNA of a sphingan-producing Sphingomonas strain into the same or a different recipient sphingan-producing Sphingomonas strain. The outcome is a hyperproducer strain containing at least two copies of at least a substantial part of the transferred DNA segment.

By way of example, isolated DNA may be introduced first into plasmid vectors, for example, pRK311 or pSEB24, among numerous others, by well-known techniques in the art, cloned and then transferred by conjugation into a recipient Sphingomonas bacterium. After insertion into a recipient Sphingomonas bacterium, the plasmid vector containing the relevant DNA fragment will then replicate in the recipient cell to give several (at least two and usually 4–20) copies of the DNA segment necessary for hyperproduction of sphingan polysaccharide. In addition to plasmid vectors, bacteriophage vectors and transposon vectors may also be used.

A number of plasmid vectors are suitable for use to insert isolated DNA segments or fragments into recipient bacteria. In addition to plasmids pRK311 and pSEB24 described above, the following plasmids, among numerous others, are also useful: broad-host-range plasmids of incompatibility group P-1, such as RK2 and derivatives therefrom such as pRK290, pRK293, pRK404 (Ditta, et al., Plasmid, Vol. 13, pp. 149–153) and other derivatives containing the oriT gene from plasmid RP4 which allows plasmid mobilization such as pSUP101 (See Simon, et al., *Bio/technology*, November, 1983) as well as plasmids pLAFR1 and pLAFR3 (Friedman, et al., *Gene*, 18, 289, 1982); and broad-host-range plasmids of incompatibility group Inc-Q, such as RSF1010 and derivatives therefrom such as pMMB22 and pMMB66 (Fürste, et al., *Gene*, 48, 119, 1986).

The use of conjugation to transfer the plasmid vectors into recipient bacteria is generally effective. In other genera of bacteria, it is more common to use transformation of competent cells with purified DNA.

Electroporation has also been used with Sphingomonas to introduce DNA fragments or plasmids into the bacteria. (See, 1992, Monteiro, et al., *J. of App. Bacteriol.*, 72, 423). Using this method, it is possible to incorporate two or more cellular copies of isolated DNA segments or fragments into recipient Sphingomonas bacteria by simply adding isolated DNA to the bacterium and then achieving transfer across the cellular membrane using the electroporation method.

Monteiro, et al., supra, describes electroporation as a means for introducing DNA into Sphingomonas. Electroporation is functionally the same as transformation of chemically treated competent cells, for example, after treatment of cells with calcium chloride or rubidium salts. The DNA to be transformed is purified by standard methods and may or may not be in plasmid form. Transformation, however, usually is most efficient when the DNA is double-stranded and closed circular. Therefore, it is not necessary to use the conjugation method of introducing DNA into Sphingomonas. Nor is it necessary to have the cloned segments inserted into a plasmid, bacteriophage or transposon vector. It is preferred, however, to first introduce isolated DNA into plasmid vectors and then transfer the plasmids containing the isolated DNA fragments into the bacteria.

Maintaining the DNA segments on plasmids or other vectors such as bacteriophage or transposon vectors in the recipient Sphingomonas is not necessary. It is routine to introduce additional copies of a DNA segment into the bacterial DNA so that the segments are replicated each generation by the same mechanism that replicates the bacterial DNA. The following examples section contains two examples which detail procedures for introducing additional copies of DNA into the bacterial DNA so that the segments are replicated each generation by the same mechanism which replicates the bacterial DNA.

10. The term "multiple copies" is used throughout the specification to describe exogenous DNA sequences, fragments or segments (at least substantial parts of said DNA) which are incorporated into Sphingomonas bacteria in at least two and preferably at least four copies. More preferably, the number of copies of a DNA sequence, fragment or segment which is inserted into a bacterium of the genus Sphingomonas, eventually ranges from about four to about 20. It is noted that in certain instances, a DNA sequence may be incorporated into a single plasmid vector, transferred into the Sphingomonas bacteria by conjugation and the plasmid may replicate in the recipient cell to provide two or more copies of the DNA sequence, segment or fragment.

11. The term "biosynthesis" is used throughout the specification to describe the biological production or synthesis of sphingan by Sphingomonas bacteria. Sphingan polysaccharides are synthesized from individual carbohydrate units in a series of steps controlled by a number of enzymes of the bacteria.

12. The term "engineered" is used throughout the specification to describe those recipient Sphingomonas bacteria into which exogenous DNA has been incorporated, preferably as multiple copies. Engineered bacteria according to the present invention are hyperproducers of sphingan polysaccharide.

13. The term "encoding genetic information" is used throughout the specification to describe DNA sequences which contain genetic information in the form of a particular order of nucleotide units. The genetic information in the DNA sequence (of any length) is considered "beneficial or essential" for the biosynthesis of sphingan in Sphingomonas bacteria, if, in multiple copies in an engineered bacteria, it will enhance sphingan production by the engineered bacteria. The term "beneficial or essential" is used to describe DNA which is isolated from Sphingomonas bacteria and codes for genetic information which, when incorporated in multiple copies in a Sphingomonas bacterium, transforms that bacterium into a hyperproducer of sphingan polysaccharide. Beneficial or essential DNA for use in the present invention may contain one or more genes or operons for the biosynthesis of glycosyl transferases, for example glucosyl IP-transferase, galactosyl IP-transferase, among others; the biosynthesis of sugar synthons, such as rhamnose, mannose, glucose, galactose, as well as substituted synthons of these sugars, such as dTDP-L-rhamnose, among others; the biosynthesis of enzymes involved in the polymerization of sugar synthons to produce sphingans, for example, polymerases, and for the secretion of polysaccharide from the intact cell structure, among others.

14. The term "interstrain complementation" is used to describe the incorporation into a second strain of Sphingomonas of DNA sequences, segments or fragments which are isolated from a first and different strain of Sphingomonas. An unexpected aspect of the present invention is the discovery that DNA fragments from different strains of Sphingomonas may be incorporated as multiple copies into other strains of Sphingomonas to produce hyperproducers of sphingan polysaccharide. The DNA fragments useful in the present invention also exhibit intergeneric complementation (e.g. to enhance xanthan production in *Xanthomonas campestris*).

15. The term "synthon" is used to describe a sugar or sugar unit which is polymerized during the biosynthesis of sphingans by bacteria according to the present invention. Synthons include sugar components which comprise constituent parts or units of the sphingan polysaccharides and are used to biosynthesize sphingans, e.g., glucose, galactose, rhamnose, mannose, other sugar synthons, including acetylated and acylated sugars and related precursors.

16. The term "rhamnose operon" is used to describe a DNA sequence encoding for a gene or operon which is involved in the biosynthesis of rhamnose or rhamnose synthons (such as dTDP-L-rhamnose), which are utilized in the biosynthesis of certain sphingan polysaccharides according to the present invention.

The present invention relates to the discovery that DNA sequences obtained from donor sphingan-producing Sphingomonas bacteria and incorporated as multiple copies into the same strain or a different strain of recipient Sphingomonas bacteria will transform the recipient Sphingomonas bacteria into a hyperproducer of sphingan polysaccharide. It further has been discovered that even where the DNA sequence is isolated from bacteria which produce one type of sphingan polysaccharide, that sequence may be incorporated as multiple copies into a different strain of Sphingomonas bacteria and produce a hyperproducer of that different strain without contamination of sphingan polysaccharide characteristic of the donor bacteria.

The relevant DNA sequence which is incorporated into the recipient bacteria encodes genetic information which is beneficial or essential for the biosynthesis of sphingan polysaccharide. For example, the beneficial or essential genetic information may be responsible for or involved in the biosynthesis of sphingan by the bacteria in any number of ways. The exogenous DNA may have a beneficial effect on the biosynthesis of sphingan for example, by expressing the synthesis of enzymes or other proteins involved in a rate-limiting enzymatic step, by inducing the synthesis of an enzyme, cofactor or other biochemical component which results in the increased production of polysaccharide, by increasing the production of an enzyme, such as a polymerase, which aids in the linking of subunits of the polysaccharide, by binding to one or more repressor genes, by aiding the secretion of the polysaccharide from the bacteria and preventing the expression of a repressor which normally inhibits the production of rate limiting steps in the biosynthesis of the polysaccharide.

The relevant DNA sequences are isolated from strains of Sphingomonas using techniques and methods which are standard in the art. The bacteria are generally cultured (standard fermentation procedures with glucose concentration below about 0.5%, preferably about 0.1% to about 0.2%, as described in further detail hereinbelow) to produce a broth containing high concentrations of bacteria. The bacterial cells are then centrifuged and resuspended for DNA extraction. The DNA may be extracted from the bacteria by first removing the proteins from the mixture, and then precipitating the high molecular weight DNA with ethanol or isopropanol. See Birnboim and Doly, *Nucl. Acids Res.*, 7, 1513 (1979).

After precipitation as described above, the isolated DNA segments or fragments generally are cloned to produce DNA for insertion into recipient Sphingomonas. By way of example, the high molecular weight DNA sequences from above are partially digested with a restriction enzyme (for example, SalI enzyme) and electrophoresed using standard methods. See Loftus, et al., BioTechniques, 12, 172 (1992). After electrophoresis, the larger DNA fragments (20 kbp and larger) are further purified (extraction and precipitation).

The DNA fragments isolated from the bacteria are thereafter inserted directly into cloning vectors (generally, plasmids) for cloning the DNA or alternatively, are further subjected to restriction enzymes to produce smaller DNA fragments which are inserted into cloning vectors. The cloning of DNA in the present invention relies on general techniques and methods which have become standard in the art. It is noted that any number of methods may be used to clone the DNA segments according to the present invention and the present invention is not limited, for example, to the use of plasmidic cloning vectors. For example, the DNA fragments may be cloned by insertion into a bacteriophage vector, such as, charon 4A, EMBL3 (See Rodriguez and Denhardt, Vectors, Chapter 2, pg. 43, 1988, Butterworth Publishers, Boston) or P1 (1990, Sternberg, *Proc. Natl. Acad. Sci. U.S.A.*, 87, 103–107)

As described in detail in examples 1 and 12, below, the DNA fragments first are prepared for insertion into a cloning vector. Any number of cloning vectors for producing DNA segments or fragments according to the present invention may be used. In the present invention, however, it has been found advantageous to clone the DNA segments or fragments in the same plasmid vector which will be used for inserting exogenous DNA into a recipient bacteria by conjugation. It is possible, however, to utilize a cloning vector (plasmidic or other) which is not going to be used as a vector for conjugation into a recipient bacteria, especially where a transformation process is going to be used to insert the DNA into the recipient bacterium.

After insertion into a cloning vector, the vector containing the isolated DNA is packaged into a bacteriophage, transferred to a bacterium (generally, *E. coli*) by a transfection process, and replicated within the transfected bacteria. The resulting colonies of bacterial cells containing cloned DNA are pooled and stored or utilized directly.

The cloned DNA is thereafter screened to determine the relative efficacy of a DNA fragment to enhance the production of sphingan in Sphingomonas. In the screening method, the DNA in an appropriate vector is then inserted into a recipient strain of Sphingomonas by conjugation (for example, tri-parental mating, as described by Ditta, et al., *Proc. Natl. Acad. Sci. USA*, 77, 7347 (1980)), the resultant engineered bacterium containing the DNA in multiple copies and its sphingan production is then tested to determine activity.

The DNA segments or fragments determined to enhance sphingan production are then transferred into a recipient Sphingomonas strain to produce a hyperproducer strain containing at least two copies of at least a substantial part of the transferred DNA segment as previously described.

A preferred screening method has been developed for use in the instant invention. In this method, DNA is screened for the presence of genes beneficial or essential for sphingan synthesis by inserting the DNA in a recipient non-producing strain of Sphingomonas. In this screening method, a non-producing mutant (for example, Sps$^-$ Bac$^r$ of strain S88) derived from a sphingan-producing strain of Sphingomonas is engineered to contain multiple copies of the DNA to be screened. After growth on nutrient agar plates containing 1–3 % glucose of the engineered non-producing mutant and comparison of colonial appearance by the engineered bacteria with non-producing mutant Sphingomonas bacteria which have been grown under identical conditions, a visual determination may be made regarding the ability of that DNA to cause the synthesis of sphingan in Sphingomonas bacteria, in general.

The determination of the ability of a DNA segment or fragment to enhance sphingan producing activity is generally based upon readily recognized phenotypic differences which exist between sphingan-producing bacteria and non-sphingan-producing mutants on culture plates. For example, sphingan-producing Sphingomonas strains are mucoid producers, which often can result in colony formation which is easily differentiated by simple visual inspection (e.g., upright round colonies surrounded by a bright ring for sphingan producers versus flat rough translucent colonies for non-producers).

In certain instances, as described in more detail in example 2, below, when the phenotypic differences between sphingan-producing bacteria and non-sphingan-producing bacteria in one Sphingomonas strain are not easily or readily recognized, the screening process may be modified to screen for the activity of the relevant DNA in bacteria where the phenotypic differences between producers and non-producers are more readily recognized by visual inspection. This aspect of the present invention makes use of the fact that DNA fragments useful in the present invention exhibit interstrain and intergeneric complementation and in multi-copies will enhance sphingan production in virtually all Sphingomonas strains.

DNA segments or fragments useful in the present invention will also exhibit activity in Xanthomonas campestris. Consequently, DNA fragments which are not easily screened by using one or more strains of Sphingomonas bacteria may be incorporated into a non-xanthan producing mutant of X. campestris, for example X59m31, among others, in multiple copies and then screened by visual inspection for the production of xanthan. The non-producing mutants of X. campestris, such as X59m31, are readily obtained by selecting survivors of exposure to bacitracin and observing whether the colonies formed by the bacitracin-resistant mutants on YM agar plates are mucoid (producers) or non-mucoid (non-producers) in appearance. (See, Pollock, et al., 1994, J. Bacteriol., 176, pp. 6229–6237 and U.S. Pat. No. 5,338,841). Those DNA which exhibit increased production of polysaccharide (sphingan or xanthan) in the screened bacteria, will evidence interstrain or intergeneric complementation and enhance sphingan polysaccharide production in other strains of Sphingomonas bacteria or even different genera of bacteria (Xanthomonas).

Utilizing the simple screening method in this aspect of the present invention which generally utilizes easy to identify phenotypic differences between producers and non-producers of sphingan, one of ordinary skill employing readily available cloning and transfer techniques will be able to readily obtain DNA segments or fragments which may be used in the instant invention for enhancing the production of sphingan polysaccharides in Sphingomonas bacteria without engaging in excessive or undue experimentation.

Another aspect according to the present invention relates to the enhanced production of sphingan polysaccharide. To produce sphingan polysaccharide, engineered bacteria according to the present invention are cultured under suitable fermentation conditions, which are well known in the art. A suitable medium or fermentation broth for culturing the engineered Sphingomonas bacteria is an aqueous medium which generally contains a source of carbon such as, for example, carbohydrates including glucose, lactose, sucrose, maltose or maltodextrins, a nitrogen source such as, for example, inorganic ammonium, inorganic nitrate, organic amino acids or proteinaceous materials such as hydrolyzed yeast, soy flour or casein, distiller's solubles or corn steep liquor, inorganic salts and vitamins. A wide variety of fermentation media will support the production of sphingans according to the present invention.

The carbohydrates are included in the fermentation broth in varying amounts but usually between about 1% and 5% by weight of the fermentation medium. The carbohydrates may be added all at once prior to fermentation or alternatively, during fermentation. The amount of nitrogen may range from about 0.01% to about 0.4% by weight of the aqueous medium. A single carbon source or nitrogen source may be used, as well as mixtures of these sources.

Among the inorganic salts which find use in fermenting Sphingomonas bacteria are salts which contain sodium, potassium, ammonium, nitrate, calcium, phosphate, sulfate, chloride, carbonate and similar ions. Trace metals such as magnesium, manganese, cobalt, iron, zinc, copper, molybdenum, iodide and borate may also be advantageously included. Vitamins such as biotin, folate, lipoate, niacinamide, pantothenate, pyridoxine, riboflavin, thiamin and vitamin $B_{12}$ and mixtures thereof may also be advantageously employed.

The fermentation is carried out at temperatures between about 25° and 35° C., with optimum productivity obtained within a temperature range of about 28° and 32° C. The inoculum is prepared by standard methods of volume scale-up, including shake flask cultures and small-scale submerged stirred fermentation. The medium for preparing the inoculum can be the same as the production medium or can be any one of several standard media well-known in the art, such as Luria broth or YM medium. The concentration of carbohydrate can be reduced in the seed cultures to less than about 1% by weight. More than one seed stage may be used to obtain the desired volume for inoculation. Typical inoculation volumes range from about 0.5% to about 10% of the total final fermentation volume.

The fermentation vessel typically contains an agitator to stir the contents. The vessel also may have automatic pH and foaming controls. The production medium is added to the vessel and sterilized in place by heating. Alternatively, the carbohydrate or carbon source may be sterilized separately before addition. A previously grown seed culture is added to the cooled medium (generally, at the fermentation temperature of about 28° to about 32° C.) and the stirred culture is fermented for about 48 to about 96 hours, producing a high viscosity broth. The sphingan polysaccharide is recoved from the broth by the standard method of precipitation with an alcohol, generally isopropanol.

By way of specific example, this application discloses DNA segments or fragments which were isolated from several bacterial strains, in particular, Sphingomonas strains S88, S60, NW11, S198, S7 and S194 (available from the American Type Culture Collection as deposits ATCC31554, ATCC31461, ATCC53272, ATCC31853, ATCC21423 and ATCC31961, respectively). These DNA segments or fragments were found to be useful for increasing sphingan S-88, S-60 and NW-11 production in the respective strains of Sphingomonas bacteria when they were incorporated in multiple copies as extrachromosomal (plasmidic) DNA in the strains of bacteria.

Figure 8:
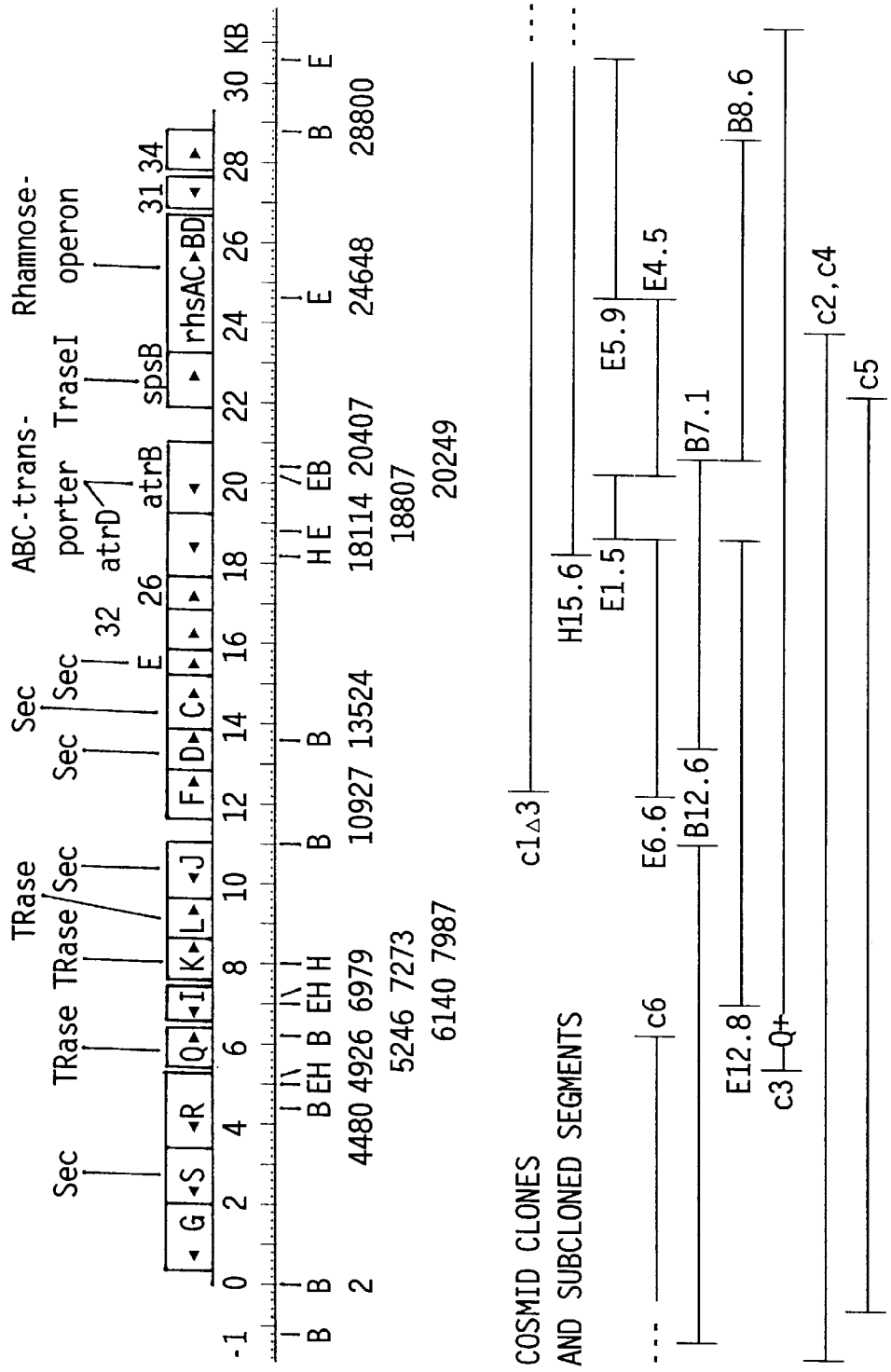
FIG. 8 is a diagrammatic representation of the restriction enzyme cleavage sites of a 34 kilobase nucleotide unit DNA segment isolated from chromosomal DNA of Sphingomonas strain S88 (ATCC accession number 31554). Restriction sites for several enzymes are also shown in FIG. 1 (as well as FIG. 2 and 3): B (BamHI), Bg (BglII), E (EcoRI), H (HindIII) and S (SalI). The spsB region, set forth in FIG. 8 (also FIG. 1), corresponds to the DNA sequence which codes for the protein SpsB. Other "sps" genes which are involved in sphingan biosynthesis are indicated by capital letters: G, S, R, Q, I, K, L, J, F, D, C and E. The genes designated as rhsACBD indicate the map position of the genes which are involved in the synthesis of a precursor to sphingans: dTDP-(L)rhamnose. Genes 32, 26, 31 and 34 are unidentified open translational reading frames, and the atrDB genes code for a transport function which is unrelated to sphingan synthesis. "Sec" indicates a gene needed for secretion of sphingans and "Trase" indicates a gene that codes for an enzyme that transfers sugar from a nucleotide-sugar precursor to sphingan during assembly of the sphingan repeat subunit.

In the case of Sphingomonas strain S88, the isolated segment of chromosomal DNA is approximately 34 kbase units in size and contains between 23 and 25 genes. As shown by the map of clones for S88 in FIG. 1, the 34 kbp region is the combined extents of two clones: c3 and c2. A number of DNA sequences from this 34 kbase DNA sequence labelled C1Δ3, c2, c3, c4, c5, c6, H15.6, B7.1, B8.6, E5.9, E1.5, E2.4, E4.5, E6.6, E12.8, etc. are also presented in FIG. 1. FIGS. 8 and 11 describe isolated S88 chromosomal DNA in further detail.

In the case of Sphingomonas strain S60, a number of DNA sequences from the chromosomal DNA were isolated including c1, c2 and c3 (see FIG. 2). Sequence c2 was cloned, placed into a pRK311 vector and inserted into Sphingomonas bacteria strains S88, S60 and NW11 to assess sphingan-producing activity (see example 9, described in further detail herein).

Figure 9:
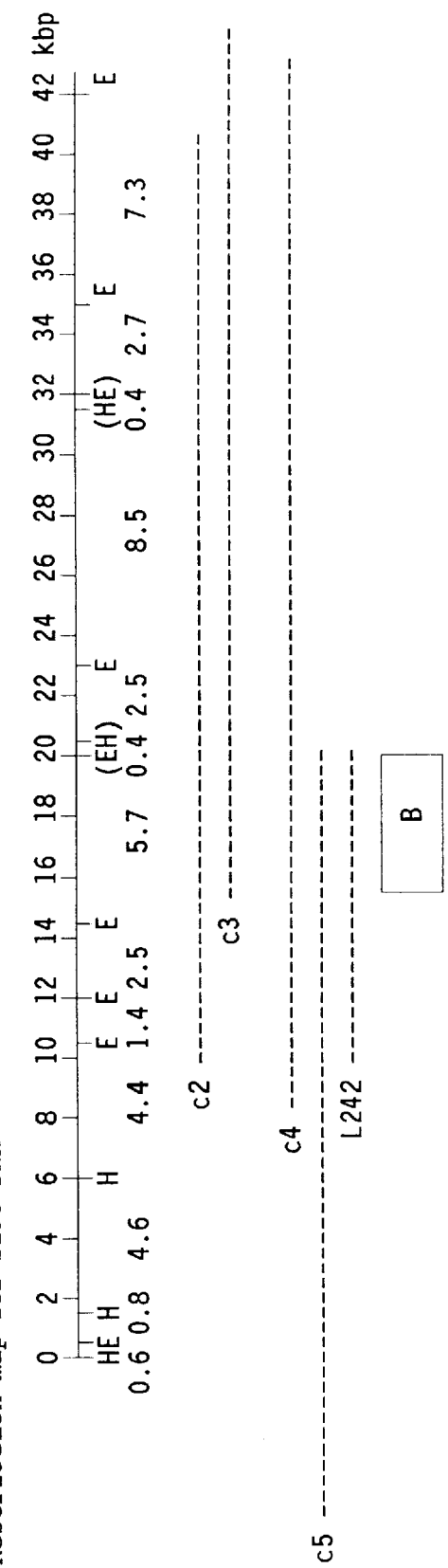
FIG. 9 is a diagrammatic representation of restriction enzyme cleavage sites of a DNA segment (approximately 42 kbase units) isolated from chromosomal DNA of Sphingomonas strain S198 (ATCC accession number 31853). Restriction sites for this DNA sequence are shown in FIG. 9 as H (HindIII) and E (EcoRI). The order of closely spaced sites enclosed within parentheses are unknown. The lateral extents of cosmid clones c2, c3, c4, c5 and subclone L242 are shown as dashed lines. The boxed "B" region corresponds to the DNA sequence which codes for the protein which complements mutants in the S88 gene spsB.
Figure 10:
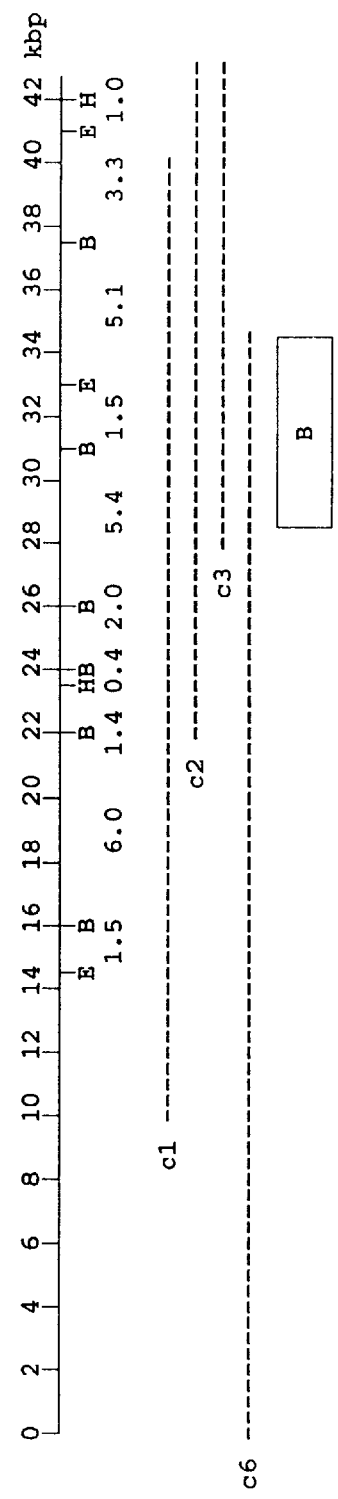
FIG. 10 is a diagrammatic representation of restriction enzyme cleavage sites of a DNA segment (approximately 42 kbase units) isolated from chromosomal DNA of Sphingomonas strain S7 (ATCC accession number 21423). Restriction sites for this DNA sequence are shown in FIG. 10 as H (HindIII)), E (EcoRI) and B (BamHI). The lateral extents of cosmid clones c1, c2, c3 and c6 are shown as dashed lines. Clones c2 and c3 extend beyond the region depicted on the right of FIG. 10. Similarly, clone c6 extends to the left. The boxed "B" region corresponds to the DNA sequence which codes for the protein which complements mutants in the S88 gene spsB.
Figure 11A:
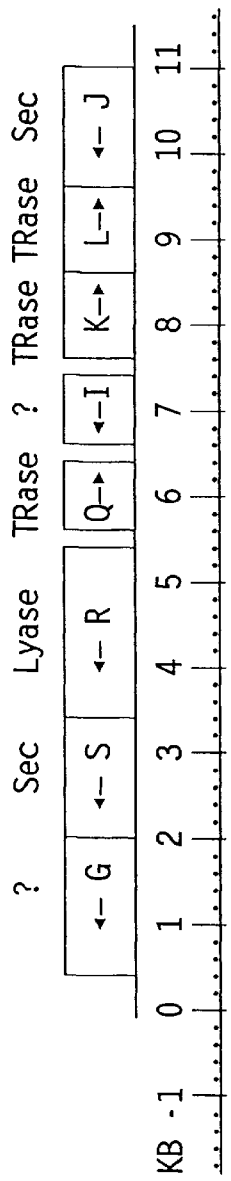
FIG. 11 is a diagrammatic representation of the gene cluster for sphingan S-88 synthesis. At the center of map are the gene names, boundaries, proposed functions, and nucleotide positions of restriction enzyme cleavage sites (B, BamHI; E, EcoRI; and H, HindIII). Cloned fragments (c1Δ3, c2, c3, c4, c5, and c6), subcloned segments (named according to restriction enzyme used and approximate length in kbp), and deletions created in the S88 chromosome (each line represents DNA presence) are indicated below the genetic map. Toward the top are the names and positions of spontaneous Sps⁻ mutations, Sps + or − complementation results, and the Sps phenotypes caused by specific insertion mutations in plasmids and the S88 chromosome. The mini-Tn10kan insertions pZ167, pZ168, pZ180, pZ202 and pZ206 were in the c2 segment cloned in plasmid pRK311 and introduced into either of two deletion strains: ΔTn493 or ΔTn495. Similarly, all of the other plasmid insertions were in the c3 segment and introduced into the deletion strains ΔTn358 and 365. The positional accuracy for the mini-Tn10kan insertions is ±50 bp relative to the sequenced restriction sites, while the graphic accuracy is ±100 bp.
Figure 11C:
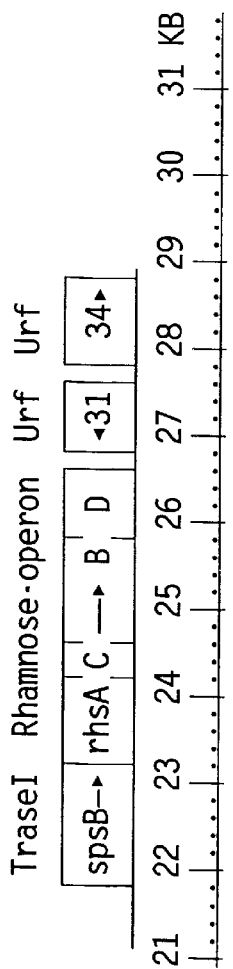
Figure 11D:
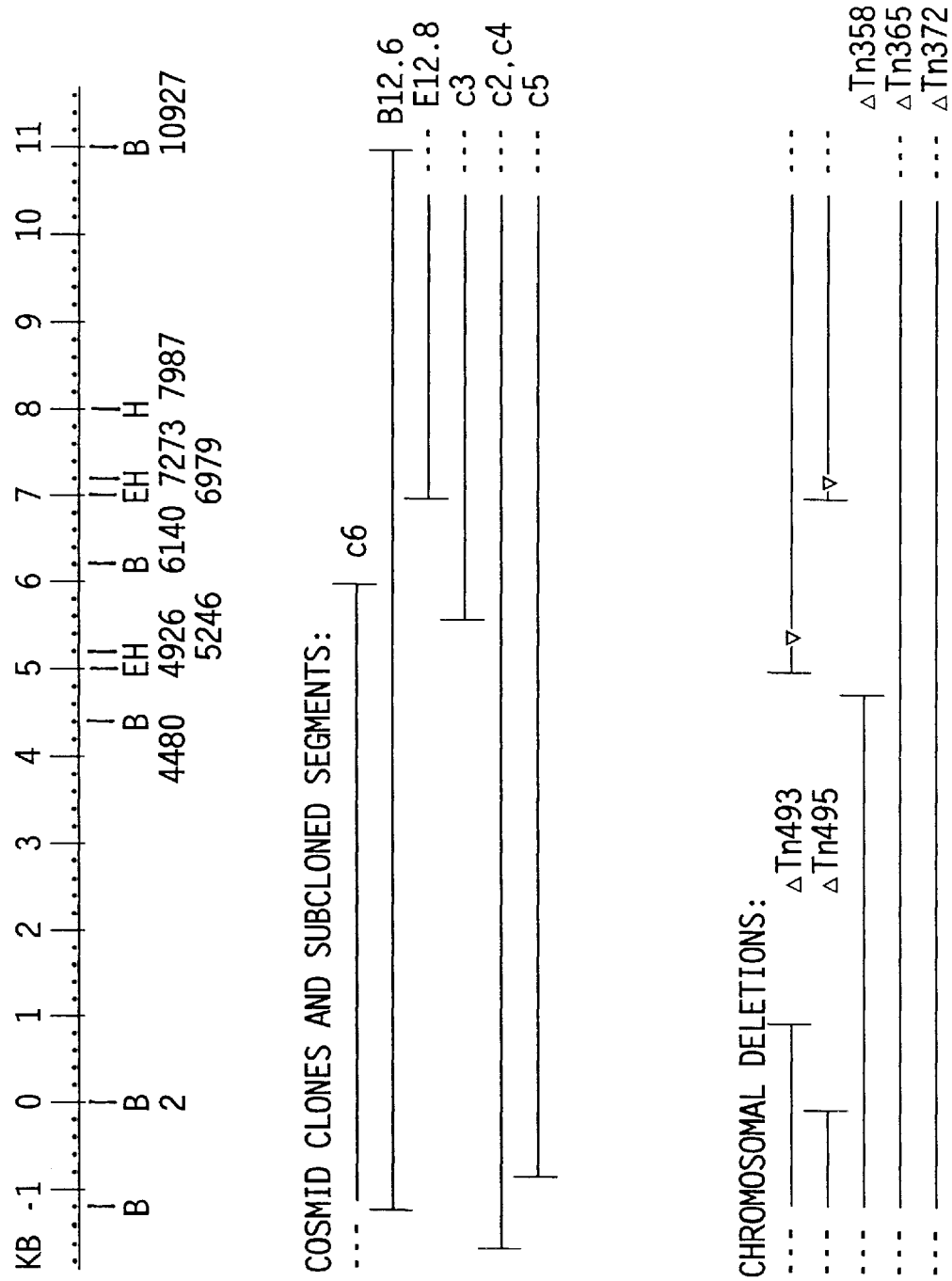
Figure 11E:
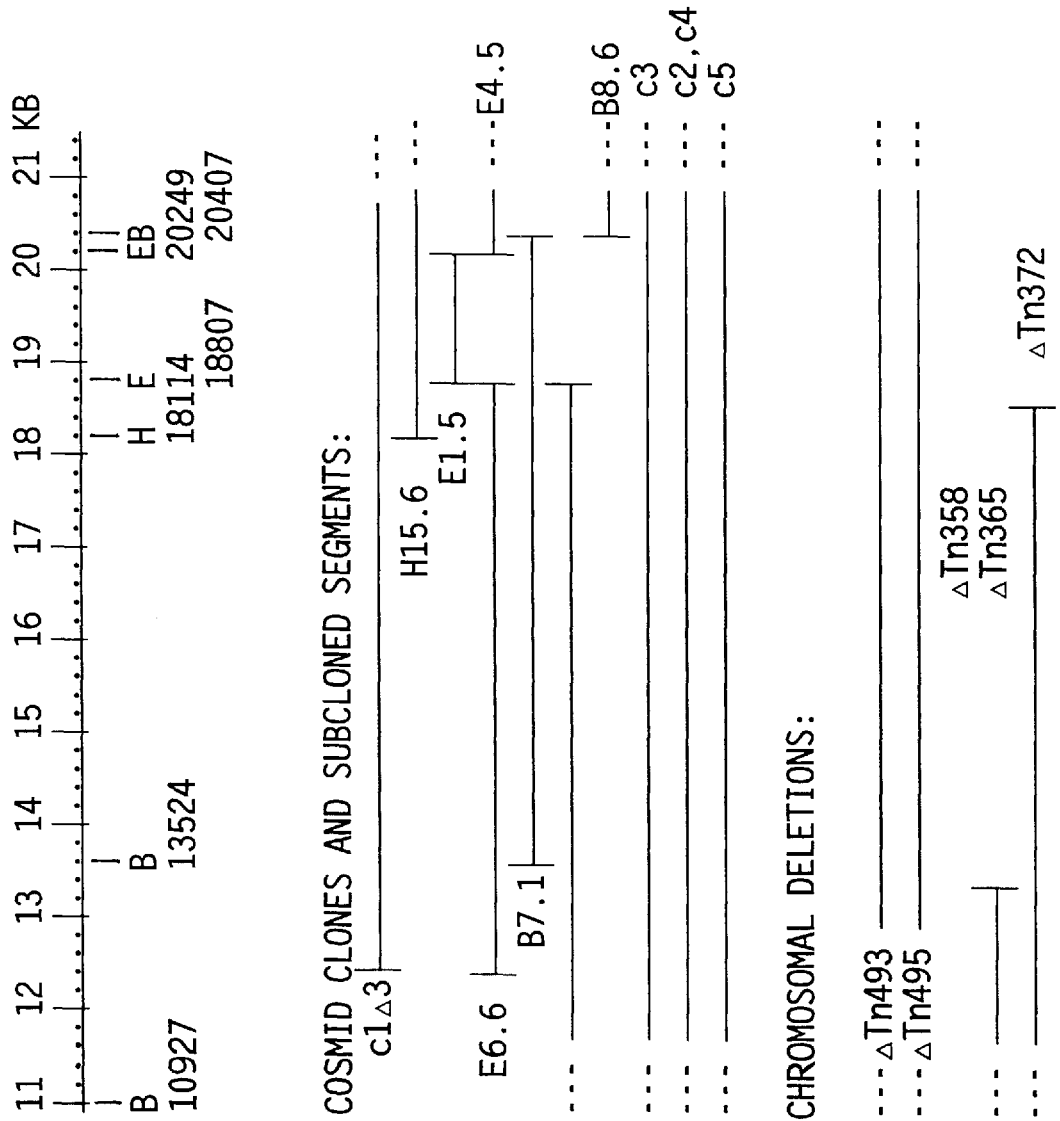

In the case of Sphingomonas strain S198, S7 and S194, DNA segments were isolated from these strains as well (See FIGS. 9 and 10). A number of additional DNA segments may also be isolated from these strains following the general methodology outlined in greater detail in this application and utilized to produce increase sphingan production in bacteria according to the present invention.

Figure 3:
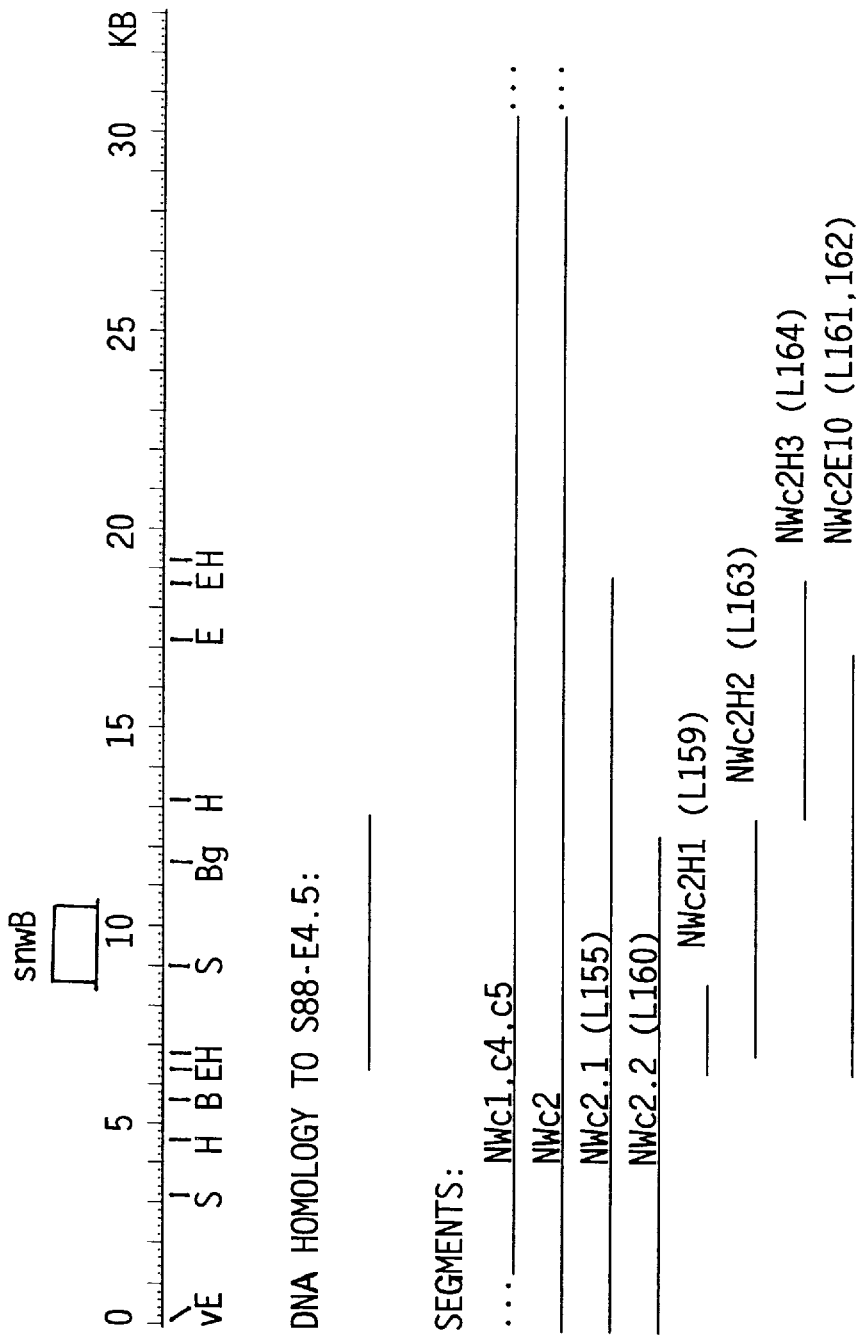
FIG. 3 is a diagrammatic representation of restriction enzyme sites of a DNA segment (approximately 33 kbase units) isolated from chromosomal DNA of Sphingomonas strain NW11 (ATCC accession number 53272). Restriction sites for this DNA sequence are shown in FIG. 3 as E, H, B, Bg and S sites. The snwB region corresponds to the DNA sequence which codes for the protein SnwB.

In the case of Sphingomonas strain NW11, DNA fragments c1, c2, c2. 1, c2.2, c2Hd, c2H1, c2H2, c2H3, c2E10 were isolated (see FIG. 3). Sequence c2.2 was cloned, placed into a pRK311 vector and inserted into Sphingomonas bacteria strains S88, S60 and NW11 to assess sphingan-producing activity (see example 9, described in further detail herein).

The following DNA segments were prepared using a procedure as generally described above from S88, S60 and NW11 strains of Sphingomonas. Each of these DNA segments (as indicated as full length DNA segments in plasmid vectors), when inserted into one or more strains of Sphingomonas (wild type sphingan producer or nonmucoid mutant derived from wild type producer), changes the bacteria into hyperproducers of sphingan polysaccharide. Each of the DNA segments or fragments is derived from the DNA segment or fragment isolated from Sphingomonas strains, inserted into plasmid vectors as indicated. The DNA segments or fragments are defined by maps of restriction enzyme cleavage sites (see FIGS. 1, 2 and 3).

Strain S88
pRK311-S88c1Δ3
pRK311-S88c2
pRK311-S88c3
pRK311-S88c4
pRK311-S88c5
pSEB24-S88H15.6
pSEB24-S88B8.6
PSEB24-S88E4.5
pSEB24-S88E6.6
Strain S60
pRK311-S60c2
Strain NW11
pRK311-NW11c2.2

The cloned DNA can be introduced into wild-type sphingan-producing Sphingomonas or non-sphingan-producing mutants to realize the hyperproduction effect. For example, the cloned DNA in multiple copies may be introduced into either sphingan-producing wild-type strains or nonmucoid mutants derived from sphingan-producing strains, respectively. The resulting engineered bacteria are hyperproducers of sphingan in comparison to sphingan-producing wild-type bacteria or mutant non-producing bacteria of the same strain.

The introduction of multiple copies of the relevant screened DNA into these strains of Sphingomonas bacteria quite unexpectedly and generally increased the sphingan produced by the recombinant bacteria compared to the level of sphingan produced by the wild-type bacteria. The phenomenon was general and the increase in sphingan exhibited interstrain complementation.

In the present invention, after introduction of the cloned DNA into the bacterium in multiple copies, the recombinant bacteria now have sphingan polysaccharide synthesis activity at levels which are elevated relative to the wild type. The DNA segments useful in the present invention carry genes which are beneficial or essential for synthesis of sphingan by Sphingomonas strains, including a DNA fragment which codes for a protein that is required to attach an initial glucose residue onto a carrier isoprenyl-phosphate, which is an early step in assembling or biosynthesizing sphingan in these strains.

The DNA sequence of the spsB gene (FIG. 4) and the deduced amino acid sequence of the SpsB protein (FIG. 5) are also disclosed. All DNA fragments which contain DNA coding for the SpsB protein (or an analogous protein such as SgeB, SnwB, SneB, SssB and SrhB, among others, depending on Sphingomonas strain) may be incorporated into Sphingomonas strains as multiple copies to enhance the production of sphingan by the resultant engineered bacteria.

Likewise, the same is true for DNA segments or fragments containing the sgeB gene (encoding the SpsB-analogous SgeB protein) isolated from S60 Sphingomonas and the snwB gene isolated from NW11 Sphingomonas. The sgeB gene (FIG. 2) is analogous to the spsB gene of the S88 chromosomal DNA (and the corresponding sneB, sssB and srhB genes from, respectively, the S198, S7 and S194 strains of Sphingomonas which encode for the SneB, SssB and SrhB proteins), in that it is believed (based upon DNA hybridization with fragments corresponding to the spsB gene of S88) to encode a protein which is analogous to the protein encoded by the spsB gene. The snwB region, set forth in FIG. 3, corresponds to the DNA sequence which encodes for the protein SnwB. The snwB gene is analogous to the spsB gene of the S88 chromosomal DNA and the sgeB gene of the S60 chromosomal DNA. These DNA fragments may be inserted into plasmids as generally described hereinabove to produce multiple copies for enhancing sphingan production in Sphingomonas.

The spsB gene is believed to code for glucosyl-IP transferase in Sphingomonas S88. There is considerable homology evidenced between the deduced amino acid sequences of SpsB protein and putative glycosyl-IP transferases from other genera of bacteria. The strongest evidence that the spsB gene codes for a glucosyl-IP transferase is the similarity of its deduced amino acid sequence to the sequences of other genes generally believed to code for glycosyl-IP transferases. Indeed there is considerable homology for the carboxyl halves of glucosyl and galactosyl-IP transferases. Although the amino terminal regions lack this extensive homology, the SpsB protein is similar to the RfbP protein of *S. enterica* (1991, Jiang, et al., Mol. Microbiol., 5, 695) in that it has multiple hydrophobic stretches which suggest membrane-spanning domains. The hydrophobic domains of SpsB include amino acids 35–59 (+2.2 average hydropathy), 68–86 (+1.7), 105–123 (+2.3) and 282–303 (+2.9). The position of the latter hydrophobic region is common to these related gene products. It is located adjacent to the region of greatest homology.

In preferred embodiments according to the present invention, DNA segments or fragments containing DNA sequences encoding for glycosyl-IP transferases of various strains of Sphingomonas bacteria, including S88, S60, NW11, S130, S194, S198, S657 and S7, among numerous others, are advantageously employed in multiple copies in recipient Sphingomonas bacteria to enhance sphingan production in the recipient bacteria. In addition to the incorporation of genes encoding for glycosyl-transferase enzymes, genes or DNA fragments encoding for sugar synthons or sugar precursors (i.e., sugar components which comprise constituent parts of the sphingan polysaccharides and are used to biosynthesize sphingans, e.g., glucose, galactose, rhamnose, mannose, other sugar synthons and precursors) or encoding for enzymes or proteins which aid in the polymerization or secretion of the polysaccharide from the intact cell structure may be advantageously employed in the present invention.

The following examples are provided to illustrate the present invention. The description of the examples should not be misconstrued to limit the scope of the present invention in any way.

EXAMPLES 1–21

In the following examples 1–21, bacterial strains, plasmids and bacteriophage are listed in the following Table 1. Luria-Bertani and YM media were standard (Pollock, et al.,1994., *J. Bacteriol.* 176:6229–6237). Amounts of antibiotics used (Sigma): bacitracin (Bac) 73 units/mg and 0.01–8 mg/ml as specified; rifampicin (Rif) 50 μg/ml; streptomycin (Stm) 50 μg/ml; kanamycin (Kan) 25 μg/ml; chloramphenicol (Cam) 15 μg/ml; and tetracycline (Tet) 4–12 μg/ml.

TABLE 1

| Name | Genotype/phenotype (polysaccharide) | Source (reference)[a] |
|---|---|---|
| Bacterial strains, plasmids and bacteriophage | | |
| Sphingomonas | | |
| S88 | Stm$^r$ Bac$^s$ Sps$^+$(sphingan S-88) | ATCC31554 |
| S88m260 | Stm$^r$ Bac$^r$ Sps- | Pollock, et al., 1994., J. Bacteriol. 176:6229–6237 |
| S60 | Stm$^r$ Bac$^s$ Sps$^+$ (sphingan S-60 or gellan) | ATCC31461 |
| X. campestris | | |
| X59 | Rif$^r$ Bac$^s$ Gum$^+$ (xanthan) | Thorne, et al., 1987, J. Bacteriol. 169:3593–3600 |
| X59m31 | Rif$^r$ Bac$^r$ Gum$^-$ | Thorne, et al., 1987, J. Bacteriol. 169:3593–3600 |
| E. coli K-12 | | |
| HMS174 | F$^-$ hsdR19(rK$^-$mK$^+$) recA1 rpoB331(Rif$^r$) ln(rmD-rmE)1 | W. Studier |
| DH5α™ | F$^-$ φ80d/acZΔM15 recA1 endA1 gyrA96 thi-1 relA1 supE44 hsdR17(rK$^-$mK$^+$) Δ(argF-lac)U169 | Bethesda Res. Lab. |
| Plasmids | | |
| pRK2013 | ori(colE1) Kan$^r$ oriT(RK2) Tra$^+$ | Figurski, et al., 1979, Proc. Nat. Acad. Sci. USA 76:1648–1652. |
| pRK311 | oriV(RK2) Tet$^r$ oriT λcos lacZ(α) | Ditta, et al. 1985. Plasmid 13:149–153.(7) |
| pMMB66EH | oriV(RSF1010) oriT Amp$^r$ lacI tacP Mcs1 | Fürste, et al., 1986, Gene, 48:119–131 |
| pUC12,13 | ori(colE1) Amp$^r$ | Vieira and Messing, 1982, Gene 19:259–268 |
| pC194 | ori(gram-positive bacteria) Cam$^r$ | Horinouchi and Weisblum, 1982, J. Bacteriol. 150:815–825 |
| pSEB23 | ori(colE1) Amp$^r$ Cam$^r$ Mcs2 | Present Invention |
| pSEB24 | oriV(RSF1010) oriT Amp$^r$ Cam$^r$ Mcs2 | Present Invention |
| pNH-Kan/oriT | ori(colE1) Amp$^r$ Kan$^r$ oriT | Hengen and Iyer, 1992, BioTechniques 13:57–62 |
| pSEB26 | ori(colE1) Amp$^r$ Cam$^r$ Kan$^r$ oriT Mcs2 | Present Invention |
| Bacteriophage | | |
| λ NK1316 | b522(ΔattP) c/857 Pam80 nin5 mini-Tn10 kan/Ptac-ATS transposase | Kleckner, et al., 1991, "Uses of transposons with emphasis on Tn10", p. 139–180. In J. H. Miller (ed.), Methods in Enzymology. Academic Press, San Diego |

[a]ATCC: American Type Culture Collection, Rockville, MD.

Example 1

Construction of a library of DNA segments from Sphingomonas

DNA fragments essential for synthesis of sphingans were cloned from strains of Sphingomonas. A complete library of DNA segments was prepared as follows. A bacterial strain (S88 in this example) was shaken overnight in 25 ml of liquid YM medium at 30° C. to give a viscous broth containing rafts of cells. YM medium contained 3 g Bacto yeast extract, 3 g Bacto malt extract, 5 g Bacto peptone (Difco) and 10 g D-glucose (Difco) per liter of water. Sodium azide was added to 0.01 % and sphinganase enzyme (1994, Mikolajczak, et al., *Appl. Environ. Mirobiol.*, 60, 402) was added for 8 hr at 37° C. to digest sphingan exopolysaccharides to partially reduce the viscosity and rafting of cells. The cells were centrifuged and resuspended for DNA extraction by the method of Birnboim and Doly, *Nucl. Acids Res.*, 7, 1513 (1979). Proteins were removed from the cleared lysate with an equal volume of phenol:CHCl3:isoamylalcohol (24:24:1) by gentle rocking for 16 hr at 25° C. and then with one volume of CHCl3:isoamyl alcohol (24:1) for 3 hr at 25° C. One-tenth volume of 3M sodium acetate (pH 5.2) was added and the high molecular weight DNA was precipitated with two volumes of ethanol, and then dried and resuspended in 0.5 ml TE (10 mM Tris-HCl pH 8, 1 mM EDTA).

According to the cosmid cloning strategy of Loftus, Foster and Ross (*BioTechniques*, 12, 172, 1992), S88 DNA was partially digested with SalI enzyme, electrophoresed through 1% low melting point agarose in Tris-acetate-EDTA buffer, and fragments larger than 20 kbp were purified by phenol extraction and ethanol precipitation. The SalI-digested S88 DNA was treated with Klenow DNA polymerase to add dCMP and dTMP to the cohesive ends, heated for 20 min at 70° C. and then precipitated with ethanol. The vector plasmid pRK311 (1985, Ditta, et al., Plasmid, 13, 149–153) was digested to completion with BamHI enzyme and then heated for 15 min at 65° C. and purified by phenol extraction and ethanol precipitation. The BamHI-digested pRK311 DNA was treated with Klenow DNA polymerase to add dGMP and dAMP and then purified as above. The ligation reaction with T4 DNA ligase contained equal molar amounts of vector and insert fragments. All restriction enzymes, Klenow DNA polymerase and T4 DNA ligase were from Stratagene and the manufacturer's reaction conditions were used. After packaging into bacteriophage (Gigapack™ IIXL of Stratagene) the ligated molecules were transferred into *E. coli* DH5α™ by transfection and cells were spread onto LB plates containing tetracycline at a concentration of from 4 to 12 μg/ml. One library of 1700 and one of 3400 Tet$^r$ colonies were separately pooled and frozen. The Tetr colonies (10 of 10 tested) contained inserts of 25 to 30 kbp with internal SalI restriction sites.

Similarly, libraries of chromosomal DNA segments were also prepared from other strains of Sphingomonas, including NW11, S60, S198, S194 and S7. In these cases, the cells which were the source for the cloned DNA were grown in medium with glucose less than 0.5% w/v, and the sphinganase treatment was omitted.

Example 2

Isolation of Biosynthetic DNA Fragments for Sphingan S-88

Fragments of DNA cloned in plasmids were screened for the presence of genes essential for sphingan S-88 synthesis by observing restoration of sphingan synthesis in sphingan-negative mutants. Previously, we found that most of the spontaneous bacitracin-resistant mutants of Sphingomonas strain S88 capable of growing on YM plates containing bacitracin at 500–800 μg/ml failed to produce sphingan polysaccharides (Pollock, et al., 1994, J. Bacteriol., 176, pp. 6229–6237). This formed the basis for a simple screening procedure for this special class of mutants.

Mutant S88m260 is a representative member of this Sps$^-$ Bac$^r$ group. The failure to make exopolysaccharides by S88m260 and the other Bac$^r$ Sps$^-$ mutants resulted in a colony appearance that was more flat, rough-surfaced and translucent compared to the wild type colonies, and the Bac$^r$ Sps$^-$ colonies were also surrounded by a narrow light-refracting halo when held up to light and viewed from below. These phenotypic differences were not as obvious as the copious mucoidy of wild type *X. campestris* and flat appearance of corresponding Gum$^-$ mutants. The colonial phenotypes were verified by growing cultures in liquid YM medium and weighing the dried exopolysaccharides after precipitation with isopropyl alcohol. Several Sps$^-$ mutants were sensitive to bacitracin and subsequently were found to define genes that were essential for sphingan synthesis but that were distinct from the gene associated with the bacitracin-resistant phenotype.

Plasmid DNA from the gene library was transferred from *E. coli* to Xanthomonas or Sphingomonas by tri-parental mating (Ditta et al. *Proc. Natl. Acad. Sci.* USA, 77, 7347, 1980). Mixtures of donor cells containing Mob$^+$ Tra$^-$ recombinant plasmids (pRK311 with S88 insert), helper cells containing Mob$^+$ Tra$^+$ pRK2013 plasmid, and exopolysaccharide-negative recipient cells in the ratio of 5:2:10 were spotted onto nonselective YM plates lacking glucose and incubated for 6–16 h at 30° C. Exconjugants of Xanthomonas were isolated by spreading a loopful of the mating mixture onto plates containing rifampicin (50 μg/ml) to select against the helper and donor cells, and tetracycline (4–12 μg/ml) for pRK311 or chloramphenicol (20 μg/ml) for pSEB24 to select for the recombinant plasmid. Sphingomonas is naturally resistant to streptomycin, which is used to select against the donor and helper cells when Sphinogomonas is the recipient.

To assess complementation, the exconjugants of strain S88 were judged by eye as either Sps$^+$ (upright round opaque colonies, surrounded by a bright ring when held up to a light and viewed from below) or Sps$^-$ (flat rough translucent colonies with no ring). Similarly, Gum$^+$ colonies grown from Xanthomonas excojugants were mucoid in appearance compared to the matte or non-shiny colonies of the Gum$^-$ recipient.

Attempts to identify the S88 clones in the library directly in nonmucoid mutants of S88 were unsuccessful (none clearly evidenced mucoidy phenotype). We then switched our approach to try to find the clones after transferring the library into nonmucoid mutants of the gumD gene of *X. campestris*. This allowed us to find the initial clone "S88c1" as described in more detail below.

The S88 gene library was mated from *E. coli* into *X. campestris* strain X59m31 which has a Bac$^r$ Gum$^-$ defect in the gumD gene (Pollock, et al. *J. Bacteriol.*, 176, pp. 6229–6237, 1994; Thorne et al., *J. Bacteriol.*, 169, 3593, 1987). From this intergeneric mating we found some Gum$^+$ Tet$^r$ colonies on YM plates and they appeared at a frequency of about $10^{-3}$ to $10^{-4}$. Individual plasmids were purified from the complemented mutants and transferred back into *E. coli* for restriction analysis. The purified plasmids were mated into Sphingomonas S88m260 and about 10% of the transconjugants became Sps$^+$. One plasmid (pRK311-S88c1) was recovered and used for subsequent work. Plasmid pRK311-S88c1 also complemented several additional independently isolated Bac$^r$ Sps$^-$ mutations in Sphingomonas strain S88 and Bac$^r$ Gum$^-$ mutants of *X. campestris*. We isolated the exopolysaccharides that were secreted into the culture medium by the exconjugants for each intergeneric mating and verified by thin layer chromatography that acid hydrolysates contained the sugar residues expected for the polysaccharide of the recipient cell. Plasmid pRK311-S88c1 restored sphingan synthesis to Sphingomonas and xanthan gum synthesis to *X. campestris*. These results indicated that plasmid pRK311-S88c1 coded for exopolysaccharide biosynthetic functions missing in the Bac$^r$ polysaccharide-negative mutants, and that genes from one genus could replace the missing function in a second genus. The segment S88c1 is similar to segment S88c1Δ3 shown in FIG. 1, except that S88c1 also includes an additional 7.5 kbp HindIII fragment at the rightmost end of S88c1Δ3. The 7.5 kbp segment was specifically deleted from S88c1 to produce the derivative S88c1Δ3.

The above-described method for determining DNA fragments useful for restoring gum production (sphingan gum in Sphingomonas sp. or xanthan gum in *X. campestris*) is reproducible, and additional clones were isolated in indirect trials. Direct screening of the clone library for segments that complemented Sps$^-$ Bac$^s$ mutations 76 and 78 of Sphingomonas S88 yielded three additional clones that partially overlapped with S88c1. The three cloned segments were each about 23–27 kb in length. Two of the three segments complemented mutant S88m260. A map of restriction enzyme cleavage sites is given in FIGS. 1 and 8.

The above-described method is utilized for determining DNA fragments isolated from Sphingomonas strains S60, NW11, S198, S7 and S194 and other sphingan-producing Sphingomonas strains which are useful for increasing sphingan production in each of these strains.

Example 3

DNA Sequence of the spsB Gene and Deduced Amino Acid Sequence of the SpsB Protein The double-stranded nucleotide sequence for 1950 bp of the spsB region was obtained from a fragment of 3300 bp subcloned from plasmid pSEB24-S88E4.5::Tn#72. The sequence of the coding strand is given in FIG. 4. There was one long open reading frame (ORF) which we named spsB. The coding region began with ATG at nucleotide 361 and continued until the TGA stop codon at 1771. This ORF coded for 470 amino acids and was preceded by a putative ribosome binding site. The deduced amino acid sequence using standard single-letter abbreviations is given in FIG. 5.

Example 4

DNA-DNA Hybridization of the Cloned S88 Segment and the Chromosomal DNA of either S88 or S60

To show that the cloned DNA in plasmid pRK311-S88c1Δ3 derived from contiguous sequences of S88 DNA we labeled plasmid S88c1Δ3 DNA and hybridized it separated restriction fragments of DNA from Sphingomonas strains S88, mutant S88m260, and 860, the wild type producer of gellan. The presence of hybridization to EcoRI fragments of about 1.5, 2.4, 4.5, 5.9, and 12 kbp is consistent with continuity for the cloned DNA in both the wild type and mutant S88 DNA. The leftmost 6.6 kbp fragment shown for S88c1Δ3 is actually 12.8 kbp when the overlapping clones S88c2, S88c3, and S88c4 are digested with EcoRI, because one of the EcoRI sites is from the multiple cloning site of the vector. The hybridization between S88 DNA and S60 DNA, which produces gellan, indicated that similar gene sequences are present but that the gene organization may be different. Because of the structural similarity between the exopolysaccharides secreted by these two Sphingomonas strains we suspect that they have similar transferase genes. The region of S88-S60 homology is given in FIG. 2. In independent tests for DNA homology we localized the homologous region between strain NW11 and S88 as shown in FIG. 3.

Example 5

Cloning of the Sphingan Biosynthetic Gene Cluster From Strains S60, NW11. S198. S7 and S194

DNA fragments were isolated from Sphingomonas S60, NW11, S198, S7 and S194. The method was the same as described in the above examples for strain S88. The maps of restriction sites of the DNA fragments from strains S60, NW11, S198, S7 and S194 are provided in FIGS. 2, 3, 9 and 10, respectively. The sizes of restriction fragments generated by digestion of DNA with single or multiple restriction enzymes are listed here for two independently isolated clones, pRK311-S194c1 and pRK311-S194c2. The sizes were determined by comparing the electrophoretic migration of the fragments through agarose gels to fragments of known size: fragments of bacteriophage lambda DNA after digestion with HindIII and the "Kb DNA Ladder" of Stratagene. The fragment sizes identify the DNA sequences included in these two cloned segments.

The following provides data for the fragment sizes for the plasmid pRK311-S194c1, which contained a c1 fragment isolated from Sphingomonas S194. The fragment sizes in kilobase pairs for pRK311-S194c1 are: (EcoRI) >25, 8.3, 5.4 and 1.5; (EcoRI+HindIII) 13.0, 9.7, 8.3, 5.4, 2.8, and 1.5; (HindIII) >25 and 2.8; (BamHI+HindIII) >25, 5.8, 3.9, 2.0, and 0.8; (BamHI) >25, 5.8 and 4.7; (BamHI+EcoRI+HindIII) 13.0, 8.3, 5.8, 5.4, 3.9, 2.0, 1.5 and 0.8; (BamHI+EcoRI) 15.0, 8.3, 5.8, 5.4, 4.7 and 1.5. The fragment sizes in kilobase pairs for pRK311-S194c2 are: (EcoRI) 14.5, 10.0, 8.3, 6.1, 2.6, and 1.35; (EcoRI+HindIII) 13, 8.3, 5.7, 4.6, 4.0, 2.6, 1.8, 1.35, 0.75, 0.35 and 0.25; (HindIII) >20, 12.8, 4.6, 2.1, 0.75 and 0.25; (BamHI+HindIII) >20, 3.8, 3.1, 2.8, 2.3, 1.65, 1.6, 1.3, 1.2, 0.95, 0.9, 0.8 and 0.25; (BamHI) >20, 5.8, 3.1, 2.8, 2.6, 2.3, 2.0, 1.6 and 0.25; (BamHI+EcoRI+HindIII) 13, 8.3, 3.8, 3.1, 2.4, 2.3, 1.6, 1.35, 1.3, 0.95, 0.9, 0.85, 0.8, 0.45, 0.35 and 0.3; (BamHI+EcoRI) 14.5, 8.3, 4.9, 3.1, 2.4, 2.3, 2.0, 1.6, 1.35, 1.3, 0.85, 0.45 and 0.2.

Example 6

Construction of Plasmids pSEB24 and pSEB 26

Plasmids pSEB24 and pSEB26 (FIG. 7) were assembled to contain specific replication and conjugal mating functions, drug-resistance genes that were suitable to Sphingomonas and compatible with mini-Tn10kan, and with multiple cloning sites. Plasmid pSEB24 has a broad host range, while pSEB26 replicates in *E. coli* but not in either Sphingomonas or Xanthomonas. First the Cam$^r$ gene on an HpaII-Sau3A fragment of 1031 bp taken from plasmid pC194 of *Staphylococcus aureus* (1982, Horinouchi and Weisblum, *J. Bacteriol.* 150, 815) was made blunt-ended and then ligated to the blunt-ended XbaI site of plasmid pUC13 (1982, Vieira and Messing, *Gene,* 259). The Cam$^r$ cassette was removed from this plasmid on a BamHI-SalI fragment, blunt-ended, and inserted into pUC12 between the unique SspI site and the nearest of the two PvuII sites (also blunt-ended) to give plasmid pSEB23 which is Amp$^r$ and Cam$^4$ and makes blue colonies with added X-Gal and IPTG. To construct pSEB24, we ligated the ScaI-PvuII fragment of about 2130 bp from pSEB23 to the ScaI-PvuII portion of pMMB66EH (1986, Furste, et al., *Gene,* 48, 119) to retain oriV (broad host range origin of replication from RSF110) and to regenerate the Amp$^r$ gene. The 2700 bp HindIII-BamHI fragment containing the oriT sequence of plasmid pNH-Kan/oriT (Hengen and Iyer, 1992, *BioTechniques* 13:57–62. ) was blunt-end ligated to the 3200 bp PvuII-linearized pSEB23 plasmid to give pSEB26. The BamHI site regenerated by the BamHII-PvuII ligation was removed by restriction followed by filling in of the cohesive ends and religation.

Example 7

Increased Production of Polysaccharide S-88 after Introduction of Copies of S88 DNA Fragments into strain S88

Specific restriction fragments of the DNA segment shown in FIG. 1 isolated from strain S88 were inserted by DNA ligation into multicopy plasmid vectors and transferred into wild type strain S88 and progeny nonmucoid mutants of S88 by the triparental conjugation system described in Example 2, above. The polysaccharide synthesis is restored by the cloned DNA when it is transferred into the mutants. The amounts of sphingan exopolysaccharides accumulated by the recombinant plasmid-containing strains and strains lacking the additional plasmid genes were measured after culturing the bacteria in liquid medium. After 24 hour growth at 30° C. with shaking in baffled flasks, two volumes of isopropyl alcohol were added to precipitate the exopolysaccharides. Two to three independent cultures were tested for each strain. The precipitates were collected on filters, dried at 80° C. and weighed. The average weight of precipitate and the standard deviation are given for each strain below in Table 2. The recombinant strains carrying additional copies of the cloned genes produced more sphingan S-88 than wild type strains carrying only the normal set of biosynthetic genes.

TABLE 2

| Host | Plasmid | Isopropyl alcohol precipitate Dry weight (mg) and standard deviation | Relative weight |
|---|---|---|---|
| S88 | None | 105 ± 9 | 1.0 |
| S88m265 | pRK311-S88c1Δ3 | 148 ± 16 | 1.4 |
| S88m265 | pRK311-S88c2 | 175 ± 16 | 1.7 |
| S88m265 | pRK311-S88c3 | 160 ± 7 | 1.5 |
| S88m265 | pRK311-S88c4 | 123 ± 14 | 1.2 |
| S88m265 | pSEB24-S88H15.6 | 162 ± 5 | 1.5 |
| S88m265 | pSEB24-S88B8.6 | 194 ± 7 | 1.8 |
| S88m265 | pSEB24-S88E4.5 | 154 ± 36 | 1.5 |
| S88 | None | 114 ± 12 | 1.0 |
| S88#78 | pRK311-S88c1Δ3 | 171 ± 2 | 1.5 |
| S88#78 | pRK311-S88c2 | 179 ± 7 | 1.6 |
| S88#78 | pRK311-S88c3 | 200 ± 9 | 1.8 |
| S88#78 | pRK311-S88c4 | 189 ± 10 | 1.7 |
| S88#78 | pRK311-S88c5 | 151 ± 4 | 1.3 |
| S88#78 | pSEB24-S88E6.6 | 171 ± 35 | 1.5 |
| S88#78 | pSEB24-S88E12.8 | 114 ± 10 | 1.0 |

It will be obvious to the skilled practitioner that the restriction map and nucleotide sequence of the spsB gene and surrounding DNA provide sufficient information for the construction by standard recombinant DNA methods of numerous additional sub-fragments of the approximately 32 kb region (FIG. 8). These additional fragments can be tested by the methods described here to identify segments that also cause a similar increase in production of sphingan polysaccharides. From Table 2, one can see that a small fraction of the sub-segments (for example pSEB24-S88E12.8) show no significant stimulation of production. Nevertheless, virtually all of the sub-segments cause the increased polysaccharide accumulation. From our testing to date we believe that pSEB24-S88B8.6 and pRK311-S88c3 provide the greatest stimulus to sphingan production.

The increased production does not require the presence of antibiotics in the culture to maintain a selection for the recombinant plasmids.

The increased production can result from the insertion into the chromosome or endogenous native plasmids of one or more DNA fragments, preferably encoding a gene or set of genes from this chromosomal segment. One of ordinary skill may readily introduce additional DNA fragments into a sphingan-producing bacterium by inserting DNA fragments containing relevant sphingan-producing genes into the resident bacterial chromosome, into endogenous native plasmids or into exogenous plasmid vectors. It is noteworthy that the results which have been evidenced in this application indicate that increased sphingan production is not dependent on the use of any particular plasmid vector.

Also within the scope of the present invention is the fusion of any of the above-described DNA fragments encoding gene segments or group of genes to DNA sequences known to control gene expression, for example and without limitation, the lac promoter of *Escherichia coli*.

Example 8

Identification of Exopolysaccharide Produced By Recombinant S88 Strains as Sphingan S-88

To verify that the exopolysaccharide produced by the engineered strains was the same as the recipient type, we identified the monosaccharides in acid hydrolysates by thin layer chromatography.

Extracellular xanthan from *X. campestris* and sphingan S-88 from Sphingomonas were separated from liquid culture media by precipitation with 2–3 volumes of isopropyl alcohol, dried at 80° C. and weighed. The polysaccharides were resuspended in high performance liquid chromotography (HPLC) water at 5 mg/ml. Anhydrous trifluoroacetic acid (88 μl; from Sigma Chemical Co.) was mixed with 75 μl HPLC water (Baker) and 225 μl polysaccharide (5 mg/ml) in a 0.6 ml microcentrifuge tube and incubated at 95° C. for 16 h. The hydrolysates were dried under vacuum, resuspended in 200 μl HPLC water, placed in a new microcentrifuge tube, dried again and resuspended in 45 μl HPLC water. The samples (25 μg/ml) could be stored frozen. Sugar standards (D-glucose, D-glucuronic acid, D-mannose, L-mannose, L-rhamnose, and L-fucose) were resuspended in HPLC water at 4 mg/ml. Precoated, channelled, silica gel chromatography plates (Kieselgel 60 CF 254, 10 20 cm, E. Merck) were soaked overnight in 0.3M NaH$_2$PO$_4$, dried 30 min at room temperature and then 10 min at 95° C. Samples of 1–2 μl were spotted and the chromatogram was exposed to a rising solvent mixture of 40 ml acetone, 5 ml butanol and 5 ml deionized water for 2.5 to 3 h at room temperature. The plate was dried at 65° C. for 3 min and then stained by dipping in a solution of 25 ml acetone, 0.5 ml aniline, 0.5 g diphenylamine and 3.75 ml phosphoric acid, followed by drying for 30 min at 95° C.. When *X. campestris* was the recipient of the S88 DNA fragments, glucose, mannose and glucuronic acid were present. When Sphingomonas strain S88 was the recipient for the gumD gene of *X. campestris* then rhamnose, glucose, mannose and glucuronic acid were present in amounts similar to S-88 exopolysaccharide.

Example 9

Stimulation of Production of Sphingans S-88, S-60 and NW-11, by DNA Fragments Obtained from Strains S88, S60 and NW11

The DNA fragments obtained from strains S88, S60 and NW11 following the general procedure set forth in examples 5,6 and 7, above, were used to increase production of the sphingans S-88, gellan (S-60) and NW-11 in Sphingomonas strains. The results are given in the following Table 3.

TABLE 3

| Host | Plasmid | Isopropyl alcohol precipitate Dry weight (mg) and standard deviation | Relative weight |
|---|---|---|---|
| S88 | pRK311 | 98 ± 5 | 1.0 |
| S88 | pRK311-S88c2 | 155 ± 24 | 1.6 |
| S88 | pRK311-S60c2 | 133 ± 11 | 1.4 |
| S88 | pRK311-NWc2.2 | 165 ± 15 | 1.7 |
| S60 | pRK311 | 49 ± 11 | 1.0 |
| S60 | pRK311-S88c2 | 73 ± 2 | 1.5 |
| S60 | pRK311-S60c2 | 74 ± 2 | 1.5 |
| S60 | pRK311-NWc2.2 | 55 ± 6 | 1.1 |
| NW11 | pRK311 | 98 ± 5 | 1.0 |
| NW11 | pRK311-S88c2 | 105 ± 6 | 1.2 |
| NW11 | pRK311-S60c2 | 124 ± 5 | 1.4 |
| NW11 | pRK311-NWc2.2 | 100 ± 1 | 1.2 |

In the general approach, DNA fragments isolated from a particular strain of Sphingomonas may be used to increase production of a sphingan (not produced by that strain) in a different strain of Sphingomonas by inserting the isolated DNA fragments in multiple copies following the techniques and methods set forth in the above examples and in particular, example 7.

In the general approach supported by the instant experiment, a DNA fragment containing genetic material essential for the production of sphingan in any Sphingomonas strain may be inserted into an appropriate plasmid vector or otherwise and introduced in multiple copies into a sphingan-producing or nonmucoid mutant of the same or a different Sphingomonas strain from which the DNA is isolated, which is a sphingan producer or is a non-producing mutant of the sphingan-producing strain. The resulting engineered Sphingomonas microorganism produces sphingan in amounts which generally exceed that produced by the non-engineered, non-mutant sphingan producer under identical fermentation conditions.

The following experiments are presented to show that the incorporation of multiple copies of DNA fragments into strains of Sphinogmonas, as well as other bacteria is routine.

Example 10

Insertion of Lactose-Utilization Genes Into the Chromosome of *X. Campestris*

Using standard cloning methods involving restriction enzymes and DNA ligation, we inserted the lactose-utilization genes from a transposon, Tn951, adjacent to a previously cloned segment of *X. campestris* DNA carried on a plasmid that could not replicate in *X. campestris*. Thorne, et al., *J. Indust. Microbiol.*, 3, 321 (1988). The recombinant plasmid was then transferred into *X. campestris* by conjugation. In the recipient bacterium, the homologous DNA from *X. campestris* located adjacent to lactose-utilization genes recombined with the cellular DNA by normal homologous recombination causing the lactose-utilization genes to become attached to and contiguous with the bacterial chromosome. The result was the stable insertion of the cloned segment into the bacterial chromosome. This is explained more fully in FIG. 2 of Thorne, et al. The same approach to inserting genes into bacteria has been used by others on numerous occasions.

It is noteworthy that it is not necessary to use a plasmid as the vector to introduce exogenous DNA into a bacterium in advance of the DNA recombination described above. DNA segments carried by bacteriophage or by transposons are also well known to insert themselves into the bacterial chromosome by site-specific DNA recombination. Usually, bacteriophage insert specifically at one or a few locations, whereas transposons usually insert at numerous essentially random locations. Furthermore, it is not necessary for the DNA to be carried into the cell attached to a cloning vector, such as a plasmid. It is well known that DNA fragments can enter bacterial cells by transformation and retain the ability to recombine with the cellular DNA.

Example 11

Figure 7:
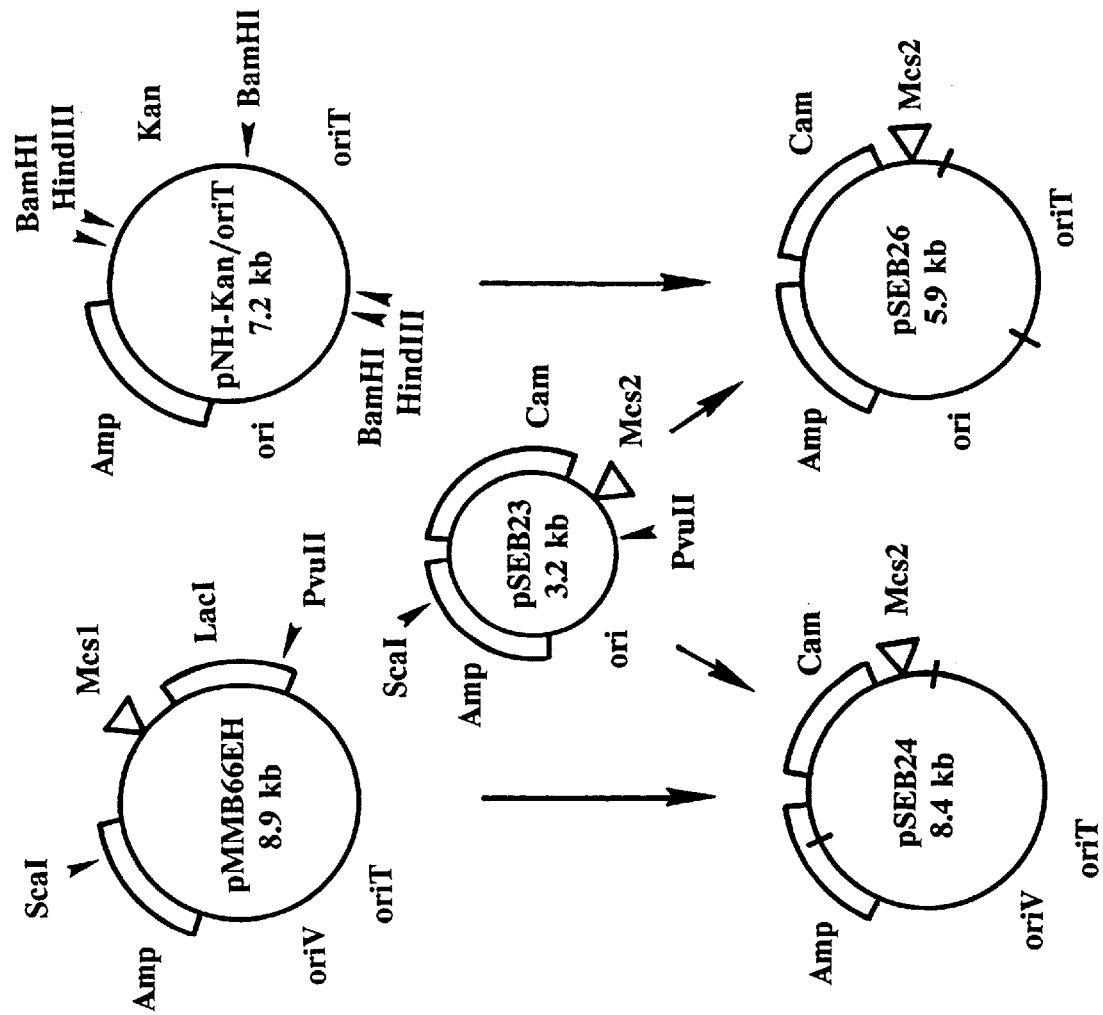
FIG. 7 is a map of the construction of plasmids pSEB24 and pSEB26 as detailed in Examples 6 and 12 of the present application. Mcs1 is a multiple cloning site that includes the following restriction sites (clockwise, from top): EcoRI, SmaI, BamHI, SalI, PstI, and HindIII. Likewise, Mcs2 includes (clockwise, from top): HindIII, PstI, SalI, XbaI, BamHI, SmaI, SstI and EcoRI. OriT is the origin of conjugal transfer, OriV is a broad-host-range replication origin, and ori is the replication origin from pUC12 and 13.

Site-Specific Insertion of a Gene Coding for Resistance to Kanamycin Into Sphingomonas S88 Bacterial DNA at Several Different Randomly Selected Locations This example demonstrates that it is routine to insert segments of cloned DNA into the cellular DNA of Sphingomonas. First, the S88E12.8 fragment (see FIG. 1) was ligated into the EcoRI site within the multiple-cloning site of the plasmid vector SEB26 (FIG. 7). Plasmid pSEB26 has the ampicillin-resistance gene, chloramphenical-resistance gene, multiple-cloning site, Lac segment, and oriT as in plasmid pSEB24 (also shown in FIG. 7). However, it differs by having a narrow-host-range origin of replication from plasmid pBR322 instead of the broad-host-range oriV sequence of plasmid pSEB24. The pBR322 origin allows the plasmid to replicate in *Escherichia coli*, but not in Sphingomonas. Therefore the only way DNA sequences cloned into plasmid pSEB26 can persist in Sphingomonas is if they become integrated into the bacterial DNA, such as the chromosome or endogenous plasmids, before the plasmid is lost from the cell or culture. Second, by routine methods, the pSEB26-S88E12.8 plasmid was exposed to mutagenesis with transposon mini-Tn10kan (1991, Kleckner, et al., 204, pp. 139–180). Mutagenesis by transposition in non-suppressing host HMS174 was with Tn10 derivative 103 (mini-Tn10kan/Ptac-ATS transposase) carried by lambda bacteriophage NK1316. The result was the insertion of a kanamycin-resistance gene into the plasmid. We isolated several independent insertions of the kanamycin-resistance gene each at a different location within the S88E12.8 segment. Third, using the triparental mating scheme we separately transferred each of the recombinant plasmids into Sphingomonas S88 and selected for kanamycin-resistant progeny. In virtually every case, the S88 DNA sequences located on either side of the kanamycin-resistance gene recombined with the recipient cell's chromosome such that the kanamycin-resistance gene became integrated into the bacterial chromosome. By integrating into the bacterial chromosome the gene was able to survive the inability of the vector plasmid to replicate in Sphingomonas.

This example shows that exogenous DNA segments (in this case the kanamycin-resistance gene) can be introduced into a recipient bacterium so that the incoming gene becomes integrated into the bacterial chromosome. The location of integration is determined by the DNA sequences that are adjacent to the gene. In this example the exogenous gene integrated into different sites within the E12.8 segment of strain S88. Integration by homologous recombination is a routinely practiced method of gene manipulation.

Example 12

Further DNA Sequencing, and Analysis

Both strands of DNA were sequenced between the BamHI sites at 1 and 28,804 bp as shown in FIG. 8. The dideoxynucleotide chain-terminating method of Sanger (Sanger, et al., 1977, *Proc. Nat. Acad. Sci.*, 74:5463–5467) was used to sequence nested deletions created in pBluescriptIIKS(+) with exonuclease III and S1 nuclease. Internal sequencing primers were also used. The sequences were analyzed with the SuperClone and SuperSee programs of Coral Software (San Diego) and by the method of Kyte and Doolittle (Kyte and Doolittle, *J. Mol. Biol.* 157:105–132. ) for membrane-spanning protein domains. Homologous protein segments in the comprehensive data library at NCBI were identified with the "blastp" program (Altschul, et al., 1990. *J. Mol. Biol.* 215:403–410). DNA hybridization was by standard methods using nylon membranes and the Genius™ 1 kit (Boehringer Mannheim).

Example 13

Cloning of Genes Involved in Sphingan S-88 Biosynthesis

This example follows some of the teachings of Example 2. Previously, we found that most sphingan polysaccharide-negative (Sps$^-$) mutants of Sphingomonas strain S88 could grow on YM plates containing bacitracin (Pollock, et al., 1994., *J. Bacteriol.* 176:6229–6237). Mapping experiments (described later) placed all of these mutations in a gene we named spsB. The representative SpsB$^-$ mutations listed in FIG. 11 (260, 265, and 102w) were also bacitracin-resistant (Bac$^r$). Conversely, the bac8 strain was typical of mutants that were initially selected as Bac$^r$ and then shown to also be Sps$^-$. As set forth in example 2, hereof, the failure to make sphingan S-88 by the Sps$^-$ Bac$^r$ mutants resulted in a colony appearance that was more flat, rough-surfaced and translucent compared to wild type colonies, which were also surrounded by a narrow light-refracting halo when held up to light and viewed from below. The Sps$^-$ mutants also failed to secrete sphingans into liquid YM medium as judged by the absence of alcohol-precipitable exopolysaccharides. A small fraction of the Sps$^-$ Bac$^r$ mutants carried second mutations. For example, colonies of mutant 102w were white rather than yellow. Mutant 134 had a mutation in the rhsD gene in addition to spsB. And mutants 54 and 302 had defects in spsK as well as spsB. The Sps$^-$ mutations shown immediately above the genetic map in FIG. 11 were either spontaneous or obtained following exposure to ultraviolet light or ethylmethane sulfonate. All of the other mutations studied here (shown in FIG. 11 with either a "Y" or "B" prefix) resulted from random insertions of transposon mini-Tn10kan.

We constructed a library of genes from Sphingomonas strain S88 in the road host range cosmid pRK311 and transferred the pooled clones from *E. coli* to S88m260 by conjugal mating. However, repeatedly no Sps$^+$ colonies appeared among the $10^3$ to $10^4$ Tet$^r$ exconjugants screened. We then transferred the library to previously isolated Bac$^r$ Gum$^-$ (gumD) mutants of *X. campestris* (Pollock, et al., 1994, *J. Bacteriol.* 176:6229–6237; and Thorne, et al., 1987, *J. Bacteriol.* 169:3593–3600). The gumD gene is required to transfer glucose-6-phosphate from UDP-glucose to isoprenyl-phosphate as the first step in the assembly of xanthan gum (Capage, et al., October 1987, International patent W087/05938 and Ielpi, et al., 1993, *J. Bacteriol.* 175:2490–2500). We thought that assembly of sphingan S-88 probably also began with glucose and that it might be possible for the enzyme from Sphingomonas to complement the Bac$^r$ Gum$^-$ mutants in *X. campestris* since DNA segments containing the gumD gene of *X. campestris* could restore sphingan S-88 synthesis in Bac$^r$ Sps$^-$ mutants of Sphingomonas (Pollock, et al., 1994, *J. Bacteriol.* 176:6229–6237). From the intergeneric matings we found Gum colonies of *X. campestris* on YM plates at a frequency of about 1 per $10^3$ to $10^4$ Tet$^r$ exconjugants.

Plasmids were purified from the complemented *X. campestris* mutants by transformation of *E. coli* and then mated into Sphingomonas S88 mutant 260. About 5–25% of the exconjugants became Sps$^+$. The frequency of transfer for the vector alone (pRK311) was 100 to 1000 times higher than for the larger recombinant plasmids. Although most of the recombinant plasmids suffered extensive deletions when mated into Sphingomonas, one was recovered intact and used for subsequent work: pRK31 1-S88c1. The leftmost 21 kbp of S88c1 is shown in FIG. 1, 8 and 11 as subclone c1Δ3. Plasmid RK311-S88c1 also restored polysaccharide synthesis to several other independently isolated Bac$^r$ Sps$^-$ mutants of strain S88 and Bac$^r$ Gum$^-$ mutants of *X. campestris*. We isolated the polysaccharides that were secreted into the culture medium by the exconjugants for each intergeneric mating and verified by thin layer chromatography that acid hydrolysates contained the neutral sugars expected for the polysaccharide of the recipient cell. Exopolysaccharide from Sphingomonas mutant 260 bearing plasmid pRK31 -S88c1 contained glucose, mannose and rhamnose, while *X. campestris* m31 with pRK311-S88c1 contained only glucose and mannose. Each polysaccharide also contained glucuronic acid although the recovery of the acidic sugar was systematically low due to the hydrolysis conditions.

We extended the cloned region toward the left in FIG. 11 by screening the library for segments that complemented the Sps$^-$ Bac$^s$ mutants 76 and 78. We screened $10^4$ to $10^6$ exconjugants and obtained four more clones (S88c2, c3, c4 and c5) that partially overlapped the S88c1 segment. Similarly, clone c6 was isolated by complementing Sps$^-$ mutants 43, 71 and 104. The five cloned segments were each about 22–28 kb in length and at least one end of each segment is shown in FIG. 11. We identified a set of about 15 Sps$^-$ mutations that were not complemented by either clone c2 or subclone c1Δ3. None of these mutations were complemented by the full-length c1 clone which extends further to the right than c1Δ3 by about 8 kbp, and none were complemented by c6 which extends to the left of c2 in FIG. 3 by about 18 kbp. The set of "unlinked" mutations suggests additional genes that are essential for sphingan synthesis but which are not immediately adjacent to the cluster of genes shown in FIG. 11.

Example 14

Mapping of the sps Genes by Functional Complementation

The boundaries of the spsG, spsK, spsF, spsD, spsC, spsE, spsB and rhsD genes were determined by complementation tests using the Sps$^+$ point mutants as recipients in conjugation. The results are summarized in FIG. 11 above the map. Recombinant plasmids bearing small subcloned DNA segments or larger segments were exposed to insertional mutagenesis with mini-Tn10kan in *E. coli* and then transferred by mating into Sps$^-$ mutants of strain S88. Two matable broad-host-range plasmid vectors were used: pRK311 and pSEB24 (FIG. 7). The exconjugants that received the drug-resistance marker of the entering plasmid were then scored as Sps$^+$ or Sps$^-$ based on colonial appearance. The Bac$^r$ Sps$^-$ S88 mutants were mapped initially to the E4.5 subclone and then the E4.5 segment was exposed to random insertional mutagenesis with mini-Tn10kan. Insertions into positions B231 and B230 (FIG. 11) did not affect the restoration of sphingan synthesis for mutant 260, however insertions B233, B239 and B238 blocked complementation. Mutant 134 was complemented by segment B8.6, but not by either E4.5 or E5.9. Mutant 134 has a defect in the spsB gene and also in the nearby rhsD gene. The more precise location of the rhsD mutation was determined by exposing the B8.6 segment to mini-Tn10kan mutagenesis and analyzing the complementation pattern for the B441, B440, B438, B437 and B435 insertions. Mutants 54 and 302 also appeared to be double mutants with defects in the spsK and spsB genes. The spsF mutants (62, 68 and 94 of FIG. 11) were localized and separated from the nearby spsDCE cluster due to the lack of complementation by segments B12.6 and c1Δ3 and by restoration of sphingan S-88 synthesis by clones c3 and c5. Complementation results for the contiguous spsD, spsC and spsE genes following insertional mutagenesis of he E6.6 fragment are also shown in FIG. 11. The complementation results suggested two groups: the first including mutations 76 and 78; and the second comprising mutations 69, 2, b104, 3, 9 and 41. Later analysis of the DNA sequences resolved the latter group into two distinct contiguous genes: spsC and spsE. The spsG mutations (11, 43, 71, 81 and 104 of FIG. 11) were complemented by the c6 clone and the B4.5 subfragment of fragment B12.6 (See FIG. 11). Insertional mutagenesis of the B12.6 segment yielded plasmids Y652, Y635, Y636, Y653, Y640 and Y641. Of these only Y652 and Y641 were able to complement the spsG mutants.

Example 15

Phenotypes of mini-Tn10kan Chromosomal and Plasmid Insertions

Segments of cloned S88 DNA were ligated to the matable narrow-host-range Cam$^r$ plasmid pSEB26 (FIG. 11), exposed to mutagenesis by mini-Tn10kan in *E. coli*, and then conjugally transferred into wild type (Sps$^+$) Sphingomonas strain S88. The plasmids were not able to replicate in Sphingomonas so that maintenance of the Kan$^r$ gene required recombination with the bacterial chromosome. We selected only those recombinants that were Kan$^r$ and Cam$^s$, expecting that this group did not retain plasmid sequences. Although we did not verify the physical structures of these DNA substitutions, we have routinely used the same plasmids, strains and selection schemes to create site-specific chromosomal deletions (bottom of FIG. 11), and confirmed those double recombination events by restriction mapping and DNA hybridization. Colonies of the Kan$^r$ Cam$^s$ chromosomal recombinants were judged as Sps$^+$ or Sps$^-$ (shown at the top of FIG. 11 for insertions labeled with a prefix "c"). For the mutants showing an Sps$^-$ phenotype (cY776, cY757, cY771, cY770, cY676, cB589, cB583, cB580, cB579, cB300, cY726, cY725, cY676, cY673, cY721, and cY602) it was reasonable to believe that double recombination occurred. However, for the Sps$^+$ recombinants, it was possible that the entire plasmid integrated into the chromosome at one of the homologous regions resulting in one defective and one normal gene in the chromosome.

To avoid the double-recombination uncertainty we created large site-specific deletions in the chromosome and then introduced replicating plasmids that carried either the S88c2 or S88c3 DNA segments with single mini-Tn10kan insertions to inactivate certain genes. The positions and Sps$^+$ or Sps$^-$ phenotypes of the insertions are shown near the top of FIG. 11 with the prefix "p". The results from the chromosomal and plasmid mutation strategies conform to one another, and both essential (−) and nonessential (+) regions were observed.

Example 16

DNA Sequence: G+C Content, Use of Rare Codons and Translational Start Sequences The DNA sequence of 28,804 bp was determined for both strands (see FIG. 14). An average profile (and standard deviation) for a typical Sphingomonas gene in this cluster was determined based on the skewed G+C contents, rare codon frequencies and "Shine-Delgarno" or translation initiation sequences (Table 4). A high frequency of G or C in the third codon position was typical for each of the genes. A set of rarely used codons for Sphingomonas was identified early in the work by analyzing 2500 codons from the rhsACBD operon and the spsB, D, C, and E genes. Each rare codon in the set was present at less than 0.2% of the total and included: AGA, AGG, CGA, TGT, GGA, ATA, CTA, TTA, TTG, AAA, TTT, CCA, CCT, AGT, TCA, TCT, ACA and ACT. Translation usually initiates in *E. coli* adjacent and downstream from a sequence that is complementary to the 3' terminus of 16S rRNA (Shine and Dalgarno, 1974, *Proc. Natl.. Acad. Sci. USA*, 71: 1342). The analogous "Shine-Delgarno" sequence complementary to 16S rRNA in *S. paucimobilis* DSM1098 is TAAGGAGGTG (Moore, et al., 1993, *Lett. Appl. Microbiol.* 17:115–118.).

If a gene in this cluster matched the average gene profile and could be mutated to give an Sps phenotype then it was given an "sps" designation. However, our search for protein similarities provided no significant hint as to the possible functions of the spsG, I and F genes. In addition there were four other open reading frames that satisfied the typical gene profile and failed to show any significant similarity to protein sequences in computer databanks. However, since mutations in these putative genes did not visibly alter polysaccharide synthesis they were labeled "Urf" for unidentified reading frame. There were four Urf sequences (32, 26, 31 and 34) which were named according to the size of the deduced protein in kilodaltons.

TABLE 4

Profiles of sps genes

| Gene | (G + C)% by condon position | | | | Condons | | Putative translational start sequences |
|------|-----|-----|-----|-----|-------|--------|----------------------------|
|      | Tot | 1st | 2nd | 3rd | Total | % rare |                            |
| spsB | 66  | 65  | 43  | 90  | 470   | 2      | TTGAGGGAGCCCGACGAGGCAATGAAC |
| C    | 68  | 70  | 48  | 87  | 447   | 1      | GACAGCGGACGAGGCCCACCAGTGAAT |
| D    | 68  | 71  | 50  | 83  | 301   | 4      | TGACAAGGGCCGTATTCATGCATGCAT |
| E    | 68  | 65  | 47  | 91  | 235   | 0      | GCACGGAGCTTCAGTAAACTGATGGAC |

TABLE 4-continued

Profiles of sps genes

| Gene | (G + C)% by condon position | | | | Condons | | Putative translational start sequences |
| | Tot | 1st | 2nd | 3rd | Total | % rare | |
|---|---|---|---|---|---|---|---|
| F | 64 | 61 | 51 | 79 | 432 | 6 | TTGTACTGGAGGCCATTGATAATGAAG |
| G | 65 | 61 | 45 | 89 | 539 | 4 | CGATTATCTAAGGGGTTGGTCATGGCG |
| I | 67 | 69 | 45 | 88 | 300 | 3 | CGTGCCGGCTGGGAGGCTTCATGAAG |
| J | 68 | 73 | 44 | 85 | 462 | 3 | CCGAAATTAAGAGGTGTTCGAGTGGCT |
| K | 68 | 72 | 46 | 85 | 352 | 3 | GGCGGGAGGCAGGCGGGATCAATGGCA |
| L | 68 | 72 | 52 | 81 | 288 | 5 | GGCACAGTGGAGTGCCAAGCGATGAGC |
| Q | 68 | 70 | 51 | 84 | 315 | 3 | CAGCACGGGTAAGAACGAGGCATGGAA |
| R | 61 | 54 | 46 | 85 | 670 | 3 | CGCGTAACGAGGGTAGAGTACATGCCG |
| S | 65 | 65 | 47 | 84 | 452 | 5 | GCAGGACTTCTATCACGTCTGATGACG |
| rhsA | 65 | 64 | 45 | 87 | 292 | 0.3 | CCCGCGCCATGGGGATTTTGAATGAAG |
| C | 65 | 65 | 43 | 88 | 188 | 2 | GCGCAAGCTGGTAGCCGCGGCATGACC |
| B | 65 | 63 | 42 | 89 | 353 | 0.6 | TTCTTCTATCAGGGCTGATCCATGCAG |
| D | 69 | 66 | 49 | 91 | 288 | 0.3 | GCGGTTGGGGCAGACCGCCTGATGCGC |
| atrB | 69 | 70 | 44 | 91 | 728 | 1 | CCATGGAGGCAGAGTACCGGAATGACA |
| atrD | 70 | 73 | 49 | 88 | 464 | 2 | CGGATATGGGGAGATTGCCGCATGAAC |
| Avg. | 67 | 67 | 47 | 87 | — | 2.5 | 5'... TAAGGAGGTG ... mRNA |
| Std. dev. | 2 | 5 | 3 | 3 | — | 1.8 | 3' ATTCCTCCAC ... rRNA |
| urf32 | 66 | 65 | 46 | 89 | 293 | 3 | ACGGCTATTGAATTGGATTCCATGACC |
| urf26 | 67 | 69 | 44 | 89 | 232 | 3 | TCACACGGCGCCGGAGGCCCCATGTTC |
| urf31 | 65 | 61 | 41 | 91 | 270 | 2 | AGACCGGGGCTGATCGAACCGATGCTT |
| urf34 | 68 | 64 | 50 | 91 | 318 | 3 | GCGCAATGACACGCGGCCGGAATGACA |

Example 17

Identification of Glucosyl-IP Transferase as spsB Gene

Most of the Sps⁻ mutations that were isolated following ultraviolet or chemical mutagenesis were in the spsB gene. The SpsB protein is believed to catalyze the first step in assembly of sphingan S-88 because of the striking similarity of the deduced amino acid sequence of SpsB to other gene products believed to code for glycosyl-IP transferases. FIG. 12 shows an alignment of amino acid sequences of suspected glucosyl- and galactosyl-IP transferases. There is considerable homology for the C-terminal halves of these proteins. Although the N-terminal regions lack this extensive homology, the SpsB protein is similar to the RfbP protein of *S. enterica* (Jiang, et al., 1991, *Molecular Microbiology*, 5, 695–713) by having several hydrophobic regions which suggest membrane-spanning domains (underlined in FIG. 12). The hydrophobic domains of SpsB include amino acids 35–59 (+2.2 average hydropathy), 68–86 (+1.7), 105–123 (+2.3) and 282–303 (+2.9). The position of the latter hydrophobic segment was common to these related gene products and was located in mid-protein adjacent to the region of greatest homology.

The spsB coding domain deduced from the DNA sequence was confirmed by complementation studies. We observed whether or not different insertions of mini-Tn10Kan in the E4.5 segment interfered with complementation of Bac⁻ Sps⁻ mutants. The sites of insertion of mini-Tn10kan and "+" or "−" complementation results are shown above the spsB gene in FIG. 11. Three mini-Tn10kan insertions failed to restore sphingan synthesis to the Sps⁻ mutant S88m260 (B233, B239, and B238) while several flanking insertions including B231 and B230 retained their ability to supply the missing function.

Example 18

Rhamnose Biosynthetic Operon of Sphinogomonas S88

The deduced amino acid sequences of the proteins coded by the rhsACBD genes were very similar to enzymes from *S. enterica* group B and *X. campestris* which synthesize dTDP-L-rhamnose in four steps from dTTP and glucose-1-phosphate (FIG. 13). We adopted the pre-existing nomenclature with glucose-1-phosphate thymidylyltransferase coded by the rhsA gene, and the successive catalytic steps coded by the rhsB, C and D genes. However, the Sphingomonas operon was unique in four respects. First, the order of genes, ACBD→, was different from either *S. enterica* (EDAC→) or *X. campestris* (BACD→). Second, intercistronic regions were almost nonexistent. Start and stop codons overlapped or were closely spaced: rhsA-ATGA-rhsC-TGATCCATG-rhsB-TGATG-rhsD. Third, the average G+C content for the rhsACBD operon (66%) was relatively high, especially in the third codon position (89%), and was uniform across the operon. And fourth, the high G+C content matched the surrounding genes in the cluster and unrelated genes from other Sphingomonas species.

Initially only one mutation (#134) was isolated within the rhs cluster, and it appeared simultaneously with a second mutation in the spsB gene. We considered the possibility that Rhs⁻ mutations might be lethal. Therefore, we tested whether or not single mutations specifically engineered within the rhs cluster would block the sphingan synthesis. First, we constructed an S88 mutant with a large chromosomal deletion (ΔTn365 in FIG. 11) spanning the spsD through rhs genes and then introduced plasmids carrying the missing DNA but with mini-Tn10kan insertions in specific sites. When the insertions in the plasmids were located within the spsD, C, E, B or rhs operon the cells remained Sps⁻. However, insertions within either Urf32, 26, 31, 34, atrD, or atrB did not interfere with the complementation of the deletion mutation and the cells became Sps⁺.

Example 19

Glycosyl Transferases of Sphinopmonas S88

Three genes are likely to code for glycosyl transferases: spsQ, spsK, and spsL. However, the sugar specificities for these transferases could not be determined by sequence analysis alone, since the proteins showed only limited local homologies to other glucosyl and rhamnosyl transferases. As noted by others the glycosyl transferases are quite divergent even for enzymes from a single bacterium that attach the same sugars in an identical linkage (Glucksman, et al., 1993, *J. Bacteriol.* 175:7045–7055). The deduced spsQ gene product was similar to orf11 adjacent to gnd in *E. coli* K-12 which is believed to code for a rhamnosyl transferase (Stevenson, et al., 1994, *J. Bacteriol.* 176:4144–4156) and was also similar to the ExoO and ExoU glucosyl transferases of *R. meliloti* (Reuber and Walker, 1993, *Cell,* 74:269–280). The spsQ gene was essential for sphingan S-88 synthesis. Mini-Tn10kan was inserted into the spsQ gene (Z206 in FIG. 11) on a plasmid bearing the S88c2 segment and the mutated plasmid was then introduced into S88 cells carrying a chromosomal deletion of the spsGSRQI genes. The recipient cells were viable but polysaccharide synthesis was blocked. The deduced spsL gene product was similar to spsQ product when compared by a dot matrix analysis, and showed some local similarity to a rhamnosyl transferase (RfbN) of *S. enterica* and a putative abequosyl transferase from *Yersinia pseudotuberculosis* (Liu, et al., 1995, *J. Bacteriol.,* 177:4084–4088). Searches for proteins similar to spsK produced only marginal similarities of which the predominant members were glycosyl transferases containing a common putative binding site for UDP. The possible involvement of UDP suggests a glucosyl or glucuronosyl transferase. A mutant with a specific insertion in the spsK gene (pY882 in FIG. 14a–14k, as well as non-insertion mutants 54 and 302 were viable but failed to make polysaccharide.

Example 20

Secretion of Polysaccharide from Bacteria

Common strategies for secretion of polysaccharides from different bacteria are suggested by sequence similarities for essential gene products. Such comparisons (Table 5) indicated that as many as five of the sps genes may be involved in secretion of sphingans: spsD, C, E, J, and S. The sequence relationships summarized in Table 5 are for proteins for which considerable information has been accumulated like the "Exo" proteins of *R. meliloti.* However, the families of functionally related proteins are larger than implied by the table. Three different segments of the SpsD protein of 51, 29 and 22 amino acids showed respectively 29, 31 and 36 percent identity to ExoF. The adjacent spsC and spsE genes with overlapping start and stop codons (TGATG) code for proteins similar to two different domains within ExoP. The similar SpsC-ExoP sequences included a motif ($PX_2PX_4SPKX_{11}GXMXG$) that was recently implicated in chain-length determination for bacterial 0-antigens (Becker, et al., 1995, *Mol. Microbiol.,* 16: 191–203). Three segments of SpsC of 92, 30 and 19 amino acids respectively were 22, 30 and 42 percent identical to similarly ordered sequences from the N-terminal half of ExoP, and two segments of SpsE of 75 and 98 amino acids were 32 and 29 percent identical to the C-terminal half of ExoP. Three segments of SpsS of 37, 20 and 44 amino acids were 38, 55 and 23 percent identical to ExoT. The deduced SpsJ protein showed some similarity to KpsT, BexA, and ABC transporters by sharing a putative nucleotide-binding domain. Although the spsR gene was not required for sphingan synthesis, its gene product was remotely similar to bacterial and fungal polysaccharide lyases. Therefore it may be important for release of the glucuronic acid-containing sphingans from either cellular or substrate surfaces, or for reuse of the polymer as a carbon source.

As shown in FIG. 11, spontaneous point mutations and mini-Tn10Kan insertions in the spsD, spsC, spsE, and spsS genes were viable but did not accumulate sphingan S-88 in culture supernatants. By contrast, mutations in analogous genes of *R. meliloti* (Harding, et al., 1993, *J. Gen. Microbiol.,* 139:447–457) and *X. campestris* were lethal. Mini-Tn10kan chromosomal insertions in the spsJ gene were also Sps$^-$. However, mini-Tn10kan insertions in spsJ maintained on a multicopy plasmid in a mutant strain with a large chromosomal deletion were either Sps$^+$ or Sps$^-$.

TABLE 5

Similarities among secretion proteins.

| Bacterium | Polysaccharide | Corresponding gene products[a] | | | | |
|---|---|---|---|---|---|---|
| Sphingomonas S88 | sphingan S-88 | SpsD | SpsC | SpsE | SpsJ | SpsS |
| R. meliloti | succinoglycan | ExoF | ExoP | ExoP | | ExoT |
| X. campestris | xanthan gum | GumB | GumC | | | GumJ |
| E. coli | polysialic acid | KpsD | | | KpsT | |
| H. influenzae | group II capsule | BexD | BexC | | BexA | |

[a]References for secretion roles of each protein:
ExoF, ExoP, ExoT (Becker et al., 1995, Mol. Microbiol., 16:191; Horinouchi and Weisblum, 1982, J. Bacteriol., 150, 815; and Reuber and Walker, 1993, Cell, 74:269)
GumB, GumC, GumJ, (Glucksmann, et al., 1993, J. Bacteriol., 175:7033; Becker et al., 1995, Mol. Microbiol., 16:191; and Glucksmann, et al., 1993, J. Bacteriol., 175:7045)
KpsD and KpsT (Wunder, et al., 1994, J. Bacteriol., 176:4025; and Smith, et al., 1990, Mol. Microbiol., 4:1863)
BexD, BexC, and BexA (Kroll, et al., 1990, Mol. Microbiol., 4:1853)

Example 21

ABC Transporter for Lytic or Toxic Protein

Located within the sps cluster were two adjacent genes, atrB and atrD, that appeared to code for an ABC transporter of a lytic or toxin-like protein and accessory protein for transport. A hemolysin gene (hlyA) has already been identified in *Pseudomonas paucimobilis,* now reclassified as a Sphingomonas. We avoided the "hly" designation at this time since with our strains we failed to detect unequivocal hemolysis on agar plates containing sheep red blood cells. About 48% of the amino acids deduced from the DNA sequence of the atrB gene were identical to those of the cyclolysin ABC transporter of *Bordatella pertussis.* The atrB gene product was also strikingly similar to the entire HlyB protein of *E. coli* and the LktB protein of *Pasteurella haemolytica* which transport hemolysin and leukotoxin respectively. In addition the C-terminal half of atrB was similar to many other ABC transporters including the C-terminal half of the NdvA protein of *R. meliloti* and the two repeated ATP-binding domains within the human multidrug resistance protein Mdr1. The atrD gene product was similar in sequence to the HlyD protein of *E. coli* and the LktD protein of *P. haemolytica.* Unlike the related transport genes from other genera there was no analogous lytic or toxic gene adjacent to the Sphingomonas atrB and atrD genes or within the sps cluster.

CONCLUSIONS

Reciprocal genetic complementation of polysaccharide-negative mutations in one genus of bacteria by DNA taken from a second genus was first demonstrated for Xanthomonas and Rhizobium (Borthakur, et al., 1988, *Mol. Gen. Genet.,* 213:155). In this early case, restoration of mucoidy was observed on agar plates. It was later reported that reciprocal intergeneric complementation occurred for the gumD gene of *X. campestris* and the spsB gene of Sphingomonas strain S88 (Pollock, et al., 1994, *J. Bacteriol.,* 176:6229), and we showed that the complementing gene from the donor restored synthesis of the exopolysaccharide of the recipient by compositional analyses.

In the present application, the experiments evidence that the spsB gene encoding glucosyl IP-transferase is an important step in the biosynthesis of sphingans. Consequently, DNA fragments which are to be incorporated into recipient bacteria according to the present invention preferably include a gene encoding for glycosyl IP-transferase enzyme (whether glucosyl-, galactosyl- or related IP transferases). It is believed that the initial step in assembling sphingan S-88, for example, is most likely transfer of a glucose-P to the carrier IP. Consequently, the inclusion of a gene which encodes for an enzyme which facilitates this biosynthetic reaction would be advantageously included in DNA fragments according to the present invention.

Our studies have shown that within the large sps gene cluster in Sphingomonas S88 there is a smaller operon coding for the biosynthesis of dTDP-L-rhamnose (rhsACBD). The sequence similarity between the rhs operon and other rhamnose operons implicates the same four enzymatic steps for L-rhamnose synthesis in Sphingomonas and evidences the desirability of incorporating an rhs operon into the DNA fragment.

The different sphingan exopolysaccharides can be thought of as defensive in nature, similar to the protective capsules of many invasive pathogenic bacteria. They may also play a role in cellular attachment to a substrate. The other sphingan-producing strains of Sphingomonas also have clusters of genes that are organized similarly to the S88 cluster described here in detail, thus making the results obtained in the examples presented here instructive in allowing one of ordinary skill to obtain workable DNA fragments from all Sphingomonas sp.

The present disclosure has shown that the production of a sphingan gum hyperproducer from a sphingan non-producer or normal producer (recipient bacterium) may be readily obtained by inserting into the recipient bacterium DNA isolated from a sphingan-producing donor Sphingomonas sp. bacterium which encodes the beneficial or essential genetic information for the biosynthesis of sphingan. Hyperproducers are readily attainable and the method is generally applicable to virtually any sphingan-producing strain of Sphinogmonas sp.

In certain preferred embodiments according to the present invention, the DNA fragment(s) obtained from the donor bacterium which contains genes or other DNA fragments, such as spsB of S88, which encode for glucosyl-IP transferase (the first step in assembly of sphingan carbohydrates) is advantageously employed in the present invention. In other embodiments according to the present invention, in particular, those embodiments in which rhamnose is an important sugar synthon or building block of the polysaccharide formed (for example, in the case of Sphingan, S-88; Gellan, S-60; and Welan, S-130), the inclusion of a rhamnose operon or gene (such as the rhsABCD genes of S-88) may be preferably employed in order to maximize production of certain sphingan polysaccharides by the hyperproducers of the present invention. In addition, genes or other DNA fragments encoding for glycosyl transferases, for example, spsQ, spsK and spsL of Sphingomonas strain S88, or for the secretion of the fmal polysaccharide formed (for example, spsD, C, E, J and S of Sphingomonas S88) may be advantageously employed where the inclusion of these enzymes will aid production of the final polysaccharide produced. Other DNA fragments or genes encoding for all of the above-described enzymes or functions may also be advantageously employed, depending upon the desired polysaccharide.

It is noted that one of ordinary skill in the art, by following the teachings of the present specification, may readily obtain DNA fragments and incorporate these fragments into recipient bacteria in order to produce sphingan hyperproducers. These hyperproducers may be readily produced using simple genetic engineering methods well known in the art.

DEPOSITS

The first six microorganisms listed below have been deposited with the American Type Culture Collection located at 12301 Parklawn Drive, Rockville, Md. 20852 pursuant to the Budapest Treaty for the International Recognition of the Deposit of Microorganisms for the Purposed of Patent Procedure. All restrictions on the availability of the materials deposited will be irrevocably removed upon the issuance of a patent thereon. The last three microorganisms are publicly available from the American Type Culture Collection in Rockville, Md.

| Microorganism | ATCC Designation |
| --- | --- |
| *Xanthomonas campestris*, X59m31 | 55653 |
| *Escherichia coli* DH5α, pRK311-S88c1 | 69732 |
| *E. coli* DH5α, pRK311-NWc1 | 69733 |
| *E. coli* DH5α, pRK311-S88c2 | 69734 |
| Sphingomonas sp. S88#78, pRK311-S88c3 | 69735 |
| Sphingomonas sp. S60 pRK311-S60c2 | 69744 |
| Sphingomonas sp. S198 | 31853 |
| Sphingomonas sp. S7 | 21423 |
| Sphingomonas sp. S194 | 31961 |

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 28804 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v ) FRAGMENT TYPE: N-terminal ( x i ) SEQUENCE DESCRIPTION: SEQ ID NO:1:

```
GGATCCACTG  GCCGGGAATT  GCCGAGAATC  CTCCGATGAA  GCGCTCGTCG  GGTACCAGCG     60
TGCCCCGGGG  CGCATCGCTT  TGCGCCGGCG  CATCGCCGCC  GCTGCCGGGC  CGGCCATTCC    120
AGCGGGGTCC  GGGCTGCAAA  ATCCCCGGGC  CTGCCTTTAC  GCCATGCCCG  GCAGCCGAGC    180
TGCCGGGCGC  CGAGCATGCG  AGCGGCGTAA  CCGATAGGGC  GAGGCCCCCG  CCCAGAAGGG    240
TGCGACGTGT  GGTATCGATC  ATGCGGCGCG  CTCCAAACCG  TGCGCGCCGT  GACTACAACC    300
AAAAATGCTG  CGCTGCGAGC  GGGATCAGGC  GCCCCGTGCC  TGCTTCGAGC  GGTACAGCAG    360
CGCGAACGTC  AGCCCCACCA  GCATGAAGAA  GACTTGGTCG  TTGTCGGTCT  GCGACAGCAC    420
GAGCCTGGTA  TTGAGCAGCA  CGACCATCGT  CGTCGCGACC  GCCAGATGCA  GCGGATAGCC    480
TTGGGAGGGG  TCCGTCAACC  CGGCGCGGAT  CAACAGCCCG  GCACCCAGCA  CCATCGTACC    540
GTAGAATGCG  ATGAAGCCGA  GCACCCCGTA  ATCGACGGCC  GTCGAAAGGA  AGCCGGAGTC    600
GATCGACAGG  AACCCGCTCT  GGGAACGCCA  TCCGACGACC  TCCGCGGACT  GGAACGGCCC    660
GTAGCCGAAT  ACCGGGCGCA  TCGCGAGCTT  GGGCAAGCCC  ATGCGGATCT  GCTCGTGGCG    720
CCCGTCGTTG  CTCGCCTGGG  TCGCGCCGCC  GCCAAGAACG  CGATTGTGTA  CCGCAGGCAC    780
TACCATGATC  ATCACCGCGA  GAACCACGGC  GAAGGCCGGA  TACATCATCG  TCGTGGAAAT    840
CCCGACGAGC  CCGCCACGCT  CCTTGATCCA  GCGCCGCAGG  CCCCAGAGCA  ACAGATAGGT    900
GGCATGCGCC  ACGACCATGC  CGACCATGCT  CAGGCGCGCG  CCGCTCCAAT  AGGCGGACAA    960
TACCATGGCG  AGATCGAACA  GGATCGTGAG  TGCCAGCGCC  GACACCGACC  GGCTGTTCAC   1020
CATCAGGTGG  ATCGCGAAGG  GAATCGTCAT  CGCCACGAGT  CGCCCCACA   CCAGCGGGTT   1080
CCCGAACACG  TTCATCACGC  GATACGTGCC  GCGCACCTGC  GAGGTGAGAT  GCAGGATGAC   1140
GCTCGGATCG  TTGATCTGCA  GCCAGCTGGG  AATGTGGCCG  ACCCACAGAA  CGTGCTCGGC   1200
CCGGAACTCG  AAGAAGCCGA  TCACCATCAG  CACGGACACG  CAGCCCAGCA  TGTTCCGCAC   1260
CCACCATTCG  GGTGTGCGCG  TGTTCGATCC  CAGGCACCAC  AGCGTCGCGA  AGAAGAACGG   1320
CGTGACCGTC  AGCGAGATAT  TCACCAGGCG  CCCGATCGAA  ACGGATGGCT  GGCTGGAAAT   1380
GAGCGACGCG  ATGATCTGGA  TGATCAGGAA  GCCCAGCATG  AAGCGGGCAA  GCCAGGGCGA   1440
CGCCGACAGC  GTCACCGCCA  TGTCGCGCCG  AAACTTCGGC  GAAATCGAAT  AGCACACCAG   1500
CAGAAGAAGC  GTCGTCAGCA  CGCCGAACAG  GCGGCGGAAG  GAGATCCAGG  GCAGGCCCGC   1560
CACCGACAGC  GACAGATAGT  TCGGCCACAC  GATCGCGAGG  ATCATGAACA  GGACGTAGCA   1620
GCGCAGCAGC  AACTTGGTGG  GCGCCTTGTC  GGCCTCCGGG  AGCGCCCAGA  TGACGAACAG   1680
CGCGAGGATC  GCCAGCGGCG  CGGCGGCCCC  GAGGAGCATG  CTGGGCGGCA  GGATCGCCGA   1740
AAGCAGCCCG  TAGACCATCG  ACACGAACAC  GATCACGGCG  AGCCCGATGA  AGCGCCGCCC   1800
GAGCGTGACG  AGACCAGAGC  GTTGCGGGTG  ATAGAGCGGG  AGCACCGCTC  TGGCGGGGAA   1860
GAACACGATG  TCGCGCGCCC  GGCGCAGGGG  CTGCACCACC  CGCGCCAAGC  CGCCGCTCCC   1920
CCGAACTCGC  GCCGATGTCG  CCATGACCAA  CCCCTTAGAT  AATCGGTATG  CCGATCAGCC   1980
```

```
GCACCGCGAC  CATCGACACG  AAGCGCAGGA  AGACCGACGG  CACCGCGATC  GCAATCGCCG   2040
CGCCTAGTGC  ACCATAGGGC  GGAATCAGGA  CCAGCGCGAG  TATTGCGGCA  AGGATAACCG   2100
ACGACATGGT  CAGCACCACG  GCCAGACGCT  CGCGATTGGC  CATGACGAGG  ACGCCGCCGC   2160
TCGACGCGAA  GACCATCCCG  AACACCTGCC  CAAGCACCAG  CACCTGCATC  GCGGCGGCGC   2220
CCGCGGTGAA  CTGTTTGCCG  AACAGGCCCA  TGATCCAATG  CGGAGCGACC  AGCACCGCCA   2280
GGGCGATGGG  CGAGGCGGCG  ACCAGCAGCG  CGAGAATGGT  GATCCGGATG  ATGCGGGCGA   2340
TCCGCTTGAC  GTCGCCCTGT  TCGTAGGAGG  CGGCAAAGAC  CGGATGCAGG  ATCGTCTCGG   2400
AGGTGGCCGA  CAGCAACTTG  AGCGAGGATG  CGATCTGATA  GCCCACCCGG  AACAGACCGG   2460
CTTCGGCGGG  GCCGTGCGTC  GCGGCAAGGA  TCACGGTGGC  AAACCAGTCG  ACGAAGAAGT   2520
TGTTGACGTT  GGTGATCAGC  ACCATGAAGC  CGGGGCGAAG  CATCGGCCGG  TCCAACGGCT   2580
CGGCCGGCGC  CCAATCACGC  GTCATGCGGC  GGACGATGAT  CGTCGCGGCA  ACATCGTCA    2640
CCAGCCAGCC  GACCAGGTAC  AGCACCGACG  GCAGCAGCGG  ATTATGGGCA  ACGCCGATCA   2700
GCAGCGCGCC  GGCCAGCATC  GCCCCACCCA  GGAAGGTGCC  GAGCGGCCCA  TCGACCATCT   2760
GCGACTTGCC  GATATCCCCC  ATGCCGCGCA  GCGTCGTCGA  AGCGAGACGG  CAATAGGCGC   2820
TGACCGGAAT  GAGAAACCCC  ATGATCAGAA  GGTCCGGCGC  CATGGCGGGG  CTGCCCAGCA   2880
GGTTGGTGGC  AATCTGTTGG  TGAAACAGCA  GGATCATCAC  CATCAGGACC  AGGCCACCAC   2940
CCACCGCGAC  CCGCGTGGCA  TGCCGCACTG  CGGTACGCGC  CACACCCGTC  CGATTTTGCG   3000
ACACGCAGAC  GGCCACGGTG  CGCACCAGGA  TGGTATCGAG  GCCGATCAGC  GACAGAATGA   3060
CCAGCATCTG  CGCAGTCGTG  AGCGCCGTAC  CGAAGGCACC  GACGCCGGCG  GGGCCAAAGG   3120
CGCGGGCGAC  CAGCCAGGTG  AAAGCGAAAC  TGGTGACGGC  GCCGAAGCCC  TTGACGCCGA   3180
AGCCGACCAC  CATCTGCCCC  CGCAGCCCCC  GCAGGTGCAA  CTTGCTACGT  GTCACGTTGA   3240
ATGCTTGCCC  CACAGGAGAT  CCCGTCTGTG  CCTTATGGCA  GGGCCCTCCC  GGGGGCAAGC   3300
CTGAGGACGT  CATCAGACGT  GATAGAAGTC  CTGCACCAAC  TTCTTGGTGG  CGAACAGGCT   3360
ATTCGCCACG  GACAGGCTGC  CCGTCGCCGA  GACGGCCGCA  GTGCCGGCCG  CATTCATGGC   3420
GATCGCCTGG  GCGAGCGACA  CTTGCGCGAC  GGACGCCGTC  GATGCCGATC  CCCCAGCGT    3480
CAGCGTGCCG  GTGGTCGCCG  CCGGCAGCGC  CGTCGACGTG  ACCGGGGTGC  CGAGAATGGT   3540
TACGGCGCTG  GCGGCCAAGC  TGCTGGTGAG  GCTGGGCTTC  ACGGTGGTGG  TCGGCTGGCT   3600
GGCGGCGGTC  GCCGCGGCAT  TCAGCGCAAG  GATCTGGGAC  GCACTGAGGG  CAGCGTCGCG   3660
CATCTCGATC  TCGCCCACGC  TGCCGCTGAA  GACAGCGTTG  AACGGGCTGC  CGATGTACAG   3720
TCCGGCATAT  TCGACCGCCC  GCGTGCTGCC  GACGATCGTT  CCCGATCCCT  TCACCACGCC   3780
ATCGACATAG  ATGATCGCCT  TGCCCTTCGC  GCTGTCATAG  GTCAGCGCGA  TCTTGTGGGT   3840
GGCCGTGTCG  GTCATCTTGG  CGCCGCTCGT  CGCGACGGTA  TAGCTCTGCC  CGGCGGCATT   3900
CTTGACGGTG  AAGACCAGTT  CGCCGTCCGC  CCGGAGCGAG  ATTCCCCAGC  TCTGGTTGAC   3960
GCCCATGATC  TGGCCGACCG  CGCCCGTCGC  GGTGGCACGC  TTCATGTCGA  AGTTGAGCGT   4020
GAAGGCGGGC  AGCGCGAAGA  GTTGACGTGA  ATTGTCCCGC  GTAAGCTCGA  AGCCGGTGCC   4080
GGTCTTCACC  TGGAACATGC  CGTTGCTGAT  GGCGGTGAGA  TCCAGCGCCT  TCGTGGTCTC   4140
GTCCGTGCTC  CAGCGCGTCT  GGTCCACGAT  TCCGGTCGCA  GTGAACTGCA  GATCCAGCAG   4200
CAGGTTGGCG  CCGGTCGAGG  TCTGTGCTGC  CGCCTGCTCC  TTGGCGACCT  GCGCGGCAAA   4260
CGCGCTGCCT  GCAGGCGGCT  GATACCCGAC  ACCACTGACG  ATCAGGTTCG  CCAGTTGCGC   4320
CTTCGATCCG  GCCATGAGAT  CGCCGATCTT  GCGAAGAGTG  ACCGCGTCCG  TTGCAAGCAC   4380
```

```
GGCGTTGTTC  GATTGAGTAA  TGCCGCTCGA  CGTTGCGGTG  ATGACAACCT  GGTCCACGAC   4440
ATTGTTGGTG  ACCTTGCCGC  CGGTCACGCC  GTCCAGGCGG  ATCCAATCGG  CGATCGCATC   4500
CATCTTCGAG  ATGATGGTAT  TGGAGTCCAC  GGTGACGTTC  TTGCCCAGAA  CGACATTGAT   4560
GCCGTGCGTG  AAACCATTCT  GGTACACGAG  ATTGTTTTTG  ATCGTGATGT  TTTCGTAGGG   4620
AATGCTGGAT  TCATTGCCCA  TGAATACGCC  CTGGAAGGCC  AGGCCGTCCC  CCTGCATCAT   4680
CACGTTATTG  GTGATCGTGA  TGTTCGTGTT  GCCCTTGGTC  TTGCCGTTCG  TCATGAACTG   4740
GATGGCGTCG  GGATGCTCAC  CATTCACCGG  ATAGAGGTTG  GTGAACATGT  TGTTGTCGAT   4800
GACGACGTTC  GACGCTTCGG  CGAAATTGGT  GTGATCGCGG  CGATTGTCGT  GGAAGTTGTT   4860
GCCCTGCAGG  GTGACACCGT  CGACGGTGAG  GACGTTCATC  CCCAGGGCGA  AATGATCGAC   4920
CGAGGAATTC  TTGATCGTCA  CCCCCTTGCT  TTCTCGCAGC  AGAAGCCCCC  AGCCCATCGA   4980
CTTCGTCACA  TCGCCCGTAC  CCCCGCTCAG  GGTCACGCCG  TCGATCACGA  CATTGCTGGA   5040
GCCGATGATC  CGGTTCGCGT  AATTATAGTC  CTGTGCCGGC  TGGAAGTTTT  GTGCGGCCGT   5100
GACGTTCTTC  ACCACCAGGT  TGCTGCTGTT  GATGATCTGC  AGGGTCGTCA  CATTCACCGG   5160
CTTGCTCGCA  TCGAGCGAGG  TGATCGTGAC  GGGCGTGGTG  AAGGTCGTGG  TGTGCACGGT   5220
GATGGACGTA  TAGGTCCCCG  CCGCAAGCTT  GATCGTCTCG  CCCCCTTTCG  CAGCCTTGAT   5280
GGCGGCGTCC  AGTTCGCTCT  GATTCCTCAC  GATGATGTCC  GGCATGTACT  CTACCCTCGT   5340
TACGCGTCGA  CCCCAATCGA  CCTGCGATCC  CTCGGACCGT  CTTGTACCTG  CCAAGCCCTG   5400
AAACGGTGGC  TAAGAGGCAG  GGTTAATGCC  CTGTTTTTCA  AGCCGATAAC  TGGCAGCCCT   5460
CAAGGCACTG  CCAGCGTGCG  GGCAACACTC  TCGACGCCGC  AGTGCAGCAC  GGGTAAGAAC   5520
GAGGCATGGA  AGCCTCGCCC  ACACCCGACG  TCAGCATCCT  GGTGGTTGCC  TACCACTCGG   5580
CTCCGTTCAT  CGGACAATGC  ATCCGGGGCA  TCGCCGCGGC  GGCACAAGGC  ACAGCCCACG   5640
AAATCCTGCT  GATCGACAAT  GGCGGCGGCG  ACACCGAGGC  GGTGGTTCGT  GCCGAGTTCC   5700
CGCACGTGCG  GATCGTGCCG  AGCGAGGGCA  ATATCGGCTT  CGGGGCGGGG  AATAACCGGT   5760
GTGCGGCCCA  TGCCCGCGCG  CCGCGGCTGC  TGCTCGTCAA  CCCCGACGCC  ATTCCCCGCC   5820
CCGGCGCGAT  CGACCTGCTG  GTCGCCTTCG  CCAAGGCGCA  CCCGGACGCG  GCAGCCTGGG   5880
GCGGGCGTTC  CTATTTTCCG  AACGGCCAGC  TGGACCATGC  CAACTTCCTC  CCGCTGCCCA   5940
CGGTGCGCGA  TTTCGTCGTG  TCGATCTTCA  GCAGCAGCCC  GATGCGGCGC  GGCGGCCTTC   6000
CTGCCGACGC  CACCGCGCCC  GGGCCGGTCG  AGGTGCTCAA  CGGCGGCTTC  ATGATGGTCG   6060
ATGCCCGCGT  GTGGCGGGAG  ATCGACGGCT  TCGACGAAGG  CTTCTTCCTC  TATTCGGAGG   6120
AAATCGATCT  GTTCCAGCGG  ATCCGCGCGC  GGGGCTATTC  CGTGCTGGTC  GATCCGGCTG   6180
TGGGCGTGGT  GCACGACACC  GGTGGCGGGC  ATTCGCTCTC  GCCCACTCGC  GTGCTGTTTC   6240
TCACCACCGG  CCGCATGCAT  TATGCCCGCA  AGCATTTCGG  CCACGTCGGT  GCCGTCGTGA   6300
CGGGCTGGGC  ACTGTGGGCC  AATGCCGCCA  AATATGTCGT  TATCGGCGGC  CTGCTCGGGC   6360
GCCTCTCACC  CCGCCGCGCG  GCGCGCTGGA  ACGCGCTGCG  CGATGCCTGG  AGCATCGTGT   6420
TCGGCCAGCC  GCGGCGCTGG  TGGCACGGCT  GGCGCGACCA  CGTTCGTACT  TGAGGATAGC   6480
GCCGCGCCAG  ACGGCCCGAA  ATGGCAACCC  GACGCAAGGC  GGAAGGCTTG  CCGACGGCAA   6540
GCCCCCCGAC  TTGTCGCTCA  CTGCGCGGCG  TTGGGCGCCG  GAGCAGGGGC  CGCAGCAGGC   6600
GCGGCGGCAG  CGCCGCCCTG  CAGTTGCGGC  GGCGGGCTGT  AGCCCGGCTG  ATATTTCACC   6660
GACTCGCGCG  CCTTCTTCAG  ACGATCGTTC  AGCTGCGCGT  CCGCCGCCTT  GCTGAACCGC   6720
TCGGTGCGCA  GCGTATTGAG  CGCGAGTTCG  CGCGCCTGAT  CGCCCGCCAG  CGGCTGGATC   6780
```

```
GTCGTGCCGG TGATGACATT GGCGGTGACG CCCTGCTGCG TCGGCAGGAT GAACAGCTCC    6840
TGCGCCGGCA GCGCCGCAAT CTTGGCGGCG ATCTCCGGCG GCAACGCGGC GGTGTCCAGC    6900
TGGGTCGGCG CGCGGCGGAA CTGCACGCCG TCGGCGGTCA GCTTGGCGGC AAGCTGGTCC    6960
AACGTCTTGA GCGGCGCGAA TTCCTTGAAC TTCGCCGCCG AGCCGGGCGG CGGGAAGACG    7020
ATCTGTTCGA TGCTGTAGAT CTTGCGCTGC GCGAAGCGAT CGGGATGCGC CGCTTCATAT    7080
TGCGCGATCT CGGCATCGGT CGGCTGGGCG ATGCCGCCGG CAATCTTGTC GCGCAGCAGC    7140
GTGGTGAGGA TCAACTCGTC GGCGCGGCGC TGCTGGATCA GGAAGACGGG GGTCTTGTCC    7200
AGCTTCTGCT CGCGGGCGTA CTTCGCGAGA ATCTTGCGCT CGATGATGCG CTGCAGCGCC    7260
ATCTGCTCGG CAAGCTTGCG GTCGGTCCCC TGCGGCACCT GCGTGGCCTG CACTTCGGCA    7320
TTCAGTTCGA AGATGGTGAT CTCGTCGCCG TCCACGCTGG CGACGACCTG CCCCTTATCG    7380
AGCTTGCCTT CCTTGCTGCC ACATCCGGAG ACGGCCAGCG CGGCCGCAGC CACCGCCGTT    7440
ACCAGGTACA ATTTCTTCAT GAAGACCTCC CAGCCGGCAC GGAATTGCGC ACGGCACAAA    7500
CTTCTACTTG AACCTATTCG GGCGGGCGGG CATCCGCAAT AGCGTTGGCA GTGCAGCATG    7560
CCTCCCGGCG GGAGGCAGGC GGGATCAATG GGGACGGCA TGGCAGAAGC GACGGTGACC     7620
GAAGCGAAGG CGGGCAAACC GCTGAAAATG TGTCTCGCAG CTTCCGGCGG CGGCCATCTG    7680
CGGCAGATCC TCGATCTGGA ATCGGTCTGG AAGGAACATG ACTATTTCTT CGTGACCGAA    7740
GACACCGCGC TGGGCCGCAG CCTTGCCGAA AAACACTCGG TCGCGCTTGT CGATCACTAT    7800
GCCCTCGGCC AGGCCAAGCT CGGCCACCCG CTGCGCATGC TGGGAGGCGC CTGGCGGAAC    7860
CTGCGGCAGA GCCTGTCGAT CATCCGCAAG CACAAGCCCG ATGTGGTGAT CTCCACCGGT    7920
GCGGGCGCGG TCTATTTCAC GGCGCTGCTC GCCAAGCTCT CGGGCGCAAA GTTCGTCCAC    7980
ATCGAAAGCT TCGCCCGGTT CGATCATCCT TCCGCCTTCG GCAAGATGGT CAAGGGCATC    8040
GCGACCGTGA CCATCGTCCA GTCCGCCGCG CTCAAGCAGA CCTGGCCGGA TGCGGAGCTG    8100
TTCGATCCCT TCCGCCTGCT CGACACCCCC CGCCCTCCCA AGCAGGCACT CACCTTCGCC    8160
ACCGTCGGTG CCACCCTGCC CTTTCGCGG CTCGTGCAGG CCGTGCTCGA TCTCAAGCGG     8220
GCCGGCGGGC TGCCGGGCAA GCTGGTGCTG CAATATGGCG ACCAGGACCT GGCCGACCCC    8280
GGCATCCCCG ACGTGGAGAT CCGCCGGACC ATTCCCTTCG ACGACCTCCA GCTGCTGCTG    8340
CGCGACGCGG ACATGGTGAT CTGCCACGGC GGCACCGGAT CGCTGGTCAC CGCGCTGCGC    8400
GCCGGCTGCC GCGTCGTCGC CTTCCCGCGC CGCCACGATC TGGGCGAGCA TTATGACGAT    8460
CACCAGGAAG AGATCGCGCA GACCTTCGCC GATCGCGGCC TGCTCCACGC CGTGCGCGAC    8520
GAGCGCGAAC TGGGCGCGGC AGTGGAGGCC GCCAAGGCGA CCGAGCCGCA GCTCGCCACC    8580
ACCGATCACA CGGCGCTCGC CGGCCGCCTG CGCGAGTTGC TGGCACAGTG GAGTGCCAAG    8640
CGATGAGCGC GCCGCGGATC AGCGTCGTCA TCCCGCACTA CAATGATCCG GACTCGCTGC    8700
GACAATGTCT CGATGCACTG CAGCATCAGA CGATCGGGCG AGAGGCCTTC GAGATCATCG    8760
TCGGAGACAA CAACTCCCCC TGCGGCCTGG CGGCAGTGGA AGCCGCCGTA GCCGGGCGCG    8820
CGCGGATCGT CACGATCCTG GAGAAGGGCG CCGGACCGGC GCGGAACGGC GCCGCGGCGG    8880
AAGCGCAGGG CGAGATTCTC GCCTTCACCG ACAGCGACTG CGTCGTCGAG CCCGGCTGGC    8940
TGGCCGGGGG CGTCGCCCAT GTCGCCCCGG GCCGCTTCGT CGGCGGCCAC ATGTATGTGC    9000
TCAAGCCGGA AGGGCGACTG ACCGGCGCGG AAGCACTCGA GATGGCGCTG GCCTTCGACA    9060
ATGAAGGCTA TGTTCGCCGT GCGAAGTTCA CCGTCACTGC CAATCTGTTC GTCATGCGGG    9120
CCGATTTCGA GCGCGTCGGC GGATTTCGTA CCGGAGTCTC GGAAGATCTG GAATGGTGCC    9180
```

```
ACCGCGCCAT CGCCACGGGT CTCGCGATCG ACTACGCCCC CGAGGCCTCG GTAGGCCACC    9240
CGCCCCGGCC GGACTGGGCA ACGCTACTGG TCAAGACGCG GCGCATCCAG CGCGAGCTGT    9300
TCCTGTTCAA TATCGAGCGC CCGCGCGGCC GGCTGCGCTG GCTTGCGCGC TCGACGCTGC    9360
AGCCTGCGCT GATTCCGGCG GATACCGCCA AGATCCTGCG CACGCCCGGC ACCCGCGGGT    9420
CCCGTATAGC TGCCGTCGGC ACGCTTGTCC GCCTGCGCTT CTGGCGCGCT GGCGCCGGCC    9480
TCCTGCAACT GCTCGGCAGA CCAATCTGAT GAAGGCGGGG CGGCCATGGT GCGGCGCCCC    9540
GTCTCCTGTC CTCACACCGC CGCGAGCGCC TCTTCCAGCG TCCCGCTGTC GATCCGCAGG    9600
CGTCCCACCA TCAGCCAGAG ATAGACGGGC AGCGAATCGT CGTTGAAGCG GAAGCGGCGC    9660
TCCCCGTCCT GCGCATCGCT CTCCAGGCCG AGCTGGCGGC TCAGCGCGTC GAGTTCCTGC    9720
TCGACCTGCG CCGCAGTGAT CGTGCTCCCC GGCAGCAGCT CGACGACTGC CTGGCCGGTG    9780
AACCAACCAT CGGTCGAACG CGACGCCTCG CCCAGCGCGG CGACCAGCGG ATCGTAGCGA    9840
CCGCCGACGA ACTTGCGCAT CTCCAGCACG GCGCGCGGCG ACATCCGGCC TTCTATTTCC    9900
AGGATGGCCT GGTCGAGCGC GCGGCGCAGA TGGCCCAGAT CGACGGTCAG CCGCCCCTGG    9960
TCGAGCGCCT CGAGCGCCGC ATGGTGGCAC AGCAGCCGCG CGAAATAGGG CGACCCCAGC   10020
GCCAGCAGGT GGATGATCCG GGTGAGGTTC GGATCGAAGC GCAGGCCCGA GGCGGTCTCG   10080
CCGAGCGCGA TCATCTCCTG TACCTCGGTT TCCTCGAGCC GCGGCATCGG CAGGCCGATG   10140
ATGTTGCGGC GGATCGAGGG TACGTAGCCG ACGAGTTCCT GCAGGTTCGA CGAGACGCCG   10200
GCGATCACCA GCTGTACGCG CGCGGAGCGG TCCGAGAGGT TCTTGATCAG TTCGGCGACC   10260
TGCTGGCGGA ACCGGGTATC CGTCACGCGG TCATATTCGT CGAGGATGAT CAGAACGCGG   10320
GTGCCGGTGA TGTCGGCGCA CAGATCGGCG AGTTCGCCCG AATCGAACGA TCCGGTCGGC   10380
AGGCGATCGG CGAGGCTTCC GCCCGATTCC GCCTCGCCCG CATTGGGCGA GACGCCGCGA   10440
TGGAACAGCA GCGGCACATC CTCTAGCACC GCGCGGAACA GGTCGGCGAA GTTGGCATTG   10500
GCGCCGCAGG TCGCGTAGCT GACGATGTAG CTGGATTCAC GCGCCACGTC GGTCAGCACA   10560
TGGAGCAGCG AGGTCTTGCC GATGCCGCGC TCGCCATAGA GCACGACATG GCTGCGCTGG   10620
CTCTCGATCG CCGAGATCAG CCGCGCCAGC ACCTCGAGGC GACCGGCAAA GCTCGAGCGG   10680
TCCGCCACCG GCTGGGTGGG CGTGAAGAAG GTGGCGAGCG CAAACCGCGC GCGGGTGATC   10740
TCGCGACGCT CTTCCCGGCG CCGGTCGAGC GGGCGATCGA GCGCGGAAGC GCGAAAGGTC   10800
GGAAAGTCGG GTCGCCCGCG GCCCGCATGC GCGTCGCGAT GGGGAACGAC GGTGGCGGCC   10860
AGCGGGAAAT ATCCGTCCTC CTCCGGTACG TCCCGACGCC CAAAGGGCCA CAAGAACTTC   10920
AGCGCGGATC CTACAGCCAC TCGAACACCT CTTAATTTCG GACGCCGCCA CGCTCGGCAG   10980
CGAACCCCTG GTTCGCGCCT TCTGGCGCCT CCCCCAAACG ATCCGGCCCC GCCTGTATCA   11040
GCGGCGCTTG AAAAACTCGT ACGGTTTGAT CACGAACGCA ATGTACGCCA GCACCAATAC   11100
AATCGTGAGG ATTGCGAAAA CATGATAGTT TTCGTTCCCG AGATAATTGG CGACGGCACA   11160
TCCGACCGCG GGAGGCAAAT AGCTGATCAT CGTGTCGCGC ACTACCGAAT CCGCCTGGGA   11220
TCGTTGCAAG AAGATCACGA TCAGGCCGGC GAATATCGCG ATGGTCACCC AATCATAGGG   11280
CGTCTGCATG CATGTCCTTT CTTTTCGGCG CCGGAATCGA AGGACTTCCG ACGTCGCCCG   11340
AACCGCACTA GCAGCGGACG GTGCAACTCG CTAGATACCG CGGTGCAGGA TAAAAGCTCG   11400
TTAAAACGCG ACCCTAGGAA TAGCGCGGTA GCGCCGGCAT GCGAGAGGTC GGGCATGCGG   11460
AAGGCCGAAG CGGCCGGGAC AGCACCGGAT GGGAGGATAT TCCCGTAGTG GGAGTGGCGA   11520
GGCCATGGCA TCCTCAGATC CGGTTGCTTG TACTGGAGGC CATTGATAAT GAAGCCAGGA   11580
```

```
CCCGGGGGAA  CATTCGTGCC  AGTAAAAGAC  GTTCAGCAAG  CGGTAGAAGT  GCGCCTCGGC   11640
GATCGTGTCT  CGCGATCGTG  CCGCGTGCTC  GCGCTGCTTG  CGACGGCAAC  GGCGATCCAG   11700
CCCGCGCTCG  CGCAGCGACA  GGCGTTCACG  CCACGCCCGA  GCGGCAGCGA  GCGCCAGATC   11760
AGCGTGCATG  CAACGGGACA  GCTCGAGTAC  AACGACAATG  TCGTGCTCAA  CGACCCGCGC   11820
ATCACCAGCG  GCGCGCGCGG  CGACGTGATC  GCCTCCCCCT  CCCTCGATCT  GAGCATTGTC   11880
CTGCCGCGCG  CGACCGGACA  GCTCTATCTC  GCGGGCACGG  TGGGCTATCG  CTTCTATCGT   11940
CGCTACACGA  ACTTCAATCG  CGAGAATATC  TCGCTCACCG  GCGGCGGCGA  CCAGCGGATC   12000
GCGTCCTGCG  TGGTGCATGG  CGAAGTCGGC  TATCAGCGCC  ACCTGACGGA  CCTGTCCAGC   12060
GTCCTCGTCC  AGGATACTGC  GCCCGCGCTC  AACAACACGG  AAGAAGCGCG  CGCCTATTCC   12120
GCGGACATCG  GCTGCGGGTC  CGCCTACGGC  CTGCGCCCTG  CACTTGCCTA  TTCGCGCAAC   12180
GAGGTTCGCA  ACAGCCTCGC  CCAGCGCAAG  TTCGCCGATT  CCGACACCAA  CACGGTCACT   12240
GCCCAGTTGG  GCCTGACGTC  GCCGGCGCTG  GCACCGTGT   CGGTGTTTGG  ACGCATGTCC   12300
GACAGCAGCT  ACATCCATCG  CACGGTACCG  GGGGTCAGTG  GCCGCGACGG  CATGAAGAGC   12360
TATGCGGCCG  GCGTCCAGCT  CGAGCGGGCG  GTCTCCAGCC  GGCTGAATTT  CCGCGGCTCC   12420
GTCAATTATT  CGGAGGTCGA  CCCCAAGCTC  GCCTCGACGC  CGGGCTTCAG  CGGGATCGGA   12480
TTCGATCTGT  CGGCGGTATA  TTCGGGCGAT  CAATATGGCG  TGCAGCTCCT  TGCGTCGCGC   12540
AACCCGCAGC  CCTCCACGCT  GCTGTTCGTA  GGCTATGAAA  TTGTGACGAC  CGTGTCGGCA   12600
ACGGCAACCC  GTAAGCTGAG  CGATCGGACC  CAACTCTCGC  TACAGGCCAC  CAAGACCTGG   12660
CGCGAGCTTG  CCTCTTCGCG  GTTGTTCACT  CTTGCGCCGA  CGACGGGCAA  CGACAACACG   12720
CTGACGCTGT  TCGGCACCGT  GAACTTCCGA  CCCAATCCTC  GGCTGAACTT  CTCGCTGGGT   12780
GCGGGCTATA  ACAAGCGCAC  CAGCAATATT  GGGCTGTATC  AATACCGCTC  CAAACGTATC   12840
AATCTCACGA  CGTCGCTGTC  GCTCTGACAA  GGGCCGTATT  CATGCATGAC  AAACACCGTT   12900
TCGTGATCCT  TTCGGCGCTC  ACCGGAATTG  CCGTACTCGC  CGCGCCCGCG  GCAGCGCAGA   12960
TTCCCACCCG  GTCCGTTCCG  ACGCCGGCGC  GGGCGCGCCC  GGCGACCCCG  CCAGCGGCCC   13020
CGCAGCAGCA  GACGACGGCA  GTGCCGACAA  CGGCAGCCAC  CGCCACCCCG  CCGGCTGCGG   13080
GTGCGGCGCC  GGCCGGCTAC  AAGATCGGCG  TCGACGACGT  GATCGAGGCG  GACGTTCTGG   13140
GCCAGTCGGA  CTTCAAGACC  CGCGCGCGCG  TGCAAGCGGA  CGGTACCGTC  ACCCTTCCCT   13200
ATCTCGGCGC  CGTGCAGGTA  CGGGGCGAGA  CCGCCGTCAC  GCTGGCCGAG  AAGCTCGCCG   13260
GCCTGCTGCG  CGCGGGTGGC  TATTACGCGA  AGCCGATCGT  CAGCGTCGAA  GTCGTCAGCT   13320
TCGTCAGCAA  CTATGTGACG  GTGCTGGGCC  AGGTGACCAC  GGCCGGCCTG  CAGCCGGTGG   13380
ATCGCGGCTA  TCACGTCTCG  GAGATCATCG  CGCGCGCCGG  CGGCCTTCGC  GCCGATGCGG   13440
CCGATTTCGT  GGTGCTCACC  CGCGCCGACG  GCACCAGTGC  CAAGCTGAAC  TACAAGCAGC   13500
TGGCCCAGGG  CGGCCCGGAG  CAGGATCCGG  TGGTCACGCC  TGGCGACAAG  CTGTTCGTGC   13560
CGGAAGTCGA  GCACTTCTAC  ATTTATGGCC  AAGTTAACGC  GCCTGGGGTA  TACGCGATTC   13620
GAACGGACAT  GACGCTCCGT  CGCGCGCTGG  CACAAGGCGG  CGGCCTTACC  CCCGCCGGCT   13680
CGTCGAAGCG  AGTGAAGGTC  TCGCGCGACG  GCCAGGAAAT  CAAGTTGAAG  ATGGACGATC   13740
CGATCAAGCC  TGGCGACACG  ATCGTCATCG  GCGAGCGGTT  GTTCTGATCT  AGGCAATGTT   13800
GACAGCGGAC  GAGGCCCACC  AGTGAATATC  ATTCAGTTCT  TCCGCATTCT  CTGGGTGCGC   13860
CGGTGGATCA  TCCTCCCGGC  GTTTCTCGTC  TGCGTCACCA  CCGCGGCGCT  GGTGGTCCAG   13920
TTCCTGCCCG  AACGCTACCG  CGCGACCACG  CGGCTGGTGC  TCGACACCTT  CAAGCCCGAT   13980
```

```
CCCGTCACCG GCCAGGTGAT GAACTCGCAG TTCATGCGCG CCTATGTCCA GACGCAGACC    14040
GAGCTGATCG AGGACTATGC GACCTCCGGC CGCGTGGTCG ACGAACTGGG CTGGGCCAAC    14100
GATCCTGCCA ACATCGCTGC CTTCAACGCC TCGTCCTCGG CGGCGACCGG CGACATTCGC    14160
CGCTGGCTCG CAAAGCAGAT CTCGGACAAC ACCAAGGCGG ATGTGATCGA GGGCAGCAAC    14220
ATCCTCGAAA TCTCCTACTC GGACAGCTCG CCCGAGCGTG CCGAGCGTAT CGCCAACCTG    14280
ATCCGCACCG CATTCCTCGC CCAGTCGCTC GCCGCCAAGC GCCAGGCGGC GGCGAAGTCG    14340
GCCGACTGGT ACACCCAGCA AGCGGAAGCG GCACGCCAGT CGCTGCTCGC GGCGGTGCAG    14400
GCGCGCACCG ACTTCGTGAA GAAGTCCGGC ATCGTGCTGA CCGAGACCGG TTCGGATCTC    14460
GATACGCAGA AGCTCGCACA GCTCCAGGGC GCGAGCGCGA TACCGTCGGC ACCGGTCGTC    14520
GCGGCCGCCA GCGGCATGGG CCCGGCGCAG CTCCAGCTTG CCCAGATCGA CCAGCAGATC    14580
CAGCAGGCGG CCACCAATCT CGGCCCGAAC CACCCGGCCT TCCAGGCCCT GCAGCGCCAG    14640
CGCGAGGTGC TCGCCCGCGC AGCGGCGGCG GAACGCAGCC AGGCAAGCGC CAGCGGCCCC    14700
GGCCGCGGCG CGCTGGAAAG CGAAGCCAAT GCCCAGCGCG CCCGCGTGCT CGGCAACCGC    14760
CAGGATGTCG ACAAGGTCAT GCAGCTCCAG CGGGACGTCA CGCTGAAGCA GGACCAGTAT    14820
ATGAAGGCGG CCCAGCGCGT CGCCGATCTG CGCCTGGAAG CAAGCAGCAA CGACACGGGC    14880
ATGAGCACGC TGAGCGAAGC CAGCGCGCCG GAAACGCCCT ATTACCCCAA GGTGCCGATG    14940
ATCATCGGCG GCGCGGCCGG CTTCGGCCTC GGCCTCGGCG TGCTGGTCGC GCTGCTCGTC    15000
GAACTGCTCG GTCGCCGCGT GCGCAGCGCC GAGGATCTCG AAGTGGCGGT CGATGCGCCG    15060
GTGCTGGGCG TGATCCAGAG CCGTGCCTCG CTCGCCGCAC GCCTGCGCCG CGCCCAAGAA    15120
ACCCTCGGCG ACCGCGCCGA AACGCACGGA GCTTCAGTAA ACTGATGGAC GCGATGACCA    15180
GCGAACCGCT GCCCGAAGGC GAGCGCCCGA GCGCCGTTCC GACGACGCCC GACACCACCG    15240
GCGTCCTGGA ATATCAGCTC GTCCTGTCCG ACCCGAACGG CATCGAAGCG GAAGCCATTC    15300
GCGCGCTGCG CACCCGCATC ATGGCGCAGC ACCTGCGCGA GGGCCGCCGC GCCCTGGCGA    15360
TCTGCGGCGC CTCGGCCGGC GTCGGCTGCA GCTTCACCGC CGCCAACCTC GCGACGGCGC    15420
TGGCGCAGAT CGGCATCAAG ACCGCGCTGG TCGATGCCAA TCTGCGCGAC CCGAGCATCG    15480
GCAGCGCCTT CAACATCGCC GCCGACAAGC CGGGCCTCGC CGACTATCTC GCCTCGGGCG    15540
ATATCGACCT CGCCTCGATC ATCCACCCGA CCAAGCTGGA CCAGCTGTCG GTGATCCATG    15600
CCGGGCATGT CGAGCACAGC CCGCAGGAAC TGCTGTCCTC CGAGCAGTTC CACGACCTCG    15660
TGACGCAGCT GCTGCGCGAG TTCGACATCA CGATCTTCGA CACCACGGCC GCGAACACCT    15720
GCGCCGATGC GCAGCGCGTC GCACATGTCG CCGGCTATGC GATCATCGTG GGGCGGAAGG    15780
ATTCGAGCTA CATCCGCGAC GTCAACACGC TCACCCGCAC GCTGCGGTCG GACCGCACCA    15840
ACGTCATCGG CTGCGTCCTG AACGGCTATT GAATTGGATT CCATGACCGC GACTGCGCTG    15900
GAGCGGCAGC AAGGACGGCG ACAGGGGGGC TATTGGCTCG CGGTCGCCGG CCTTGCGGCA    15960
CTCGCCATTC CCACTTTCGT CACGCTCGGC CGCGAAACCT GGAGCGCCGA AGGTGGCGTG    16020
CAGGGGCCGA TCGTGCTGGC GACCGGCGCC TGGATGCTGG CGCGGCAACG CGACAGCCTC    16080
GTGGCGCTCC GGCGCCCCGG CAATCTGGCG CTGGGCGCAT TGTGCCTGTT GCTGGCGCTG    16140
GGCATCTACA CCGTCGGTCG CGTGTTCGAC TTCATCAGCA TCGAGACGTT CGGGCTGGTC    16200
GCGACCTTCG TGGCGGCTGC GTTCCTCTAT TTCGGCGGCC GGGCGCTGCG CGCTGCGTGG    16260
TTCCCGACCT TGTGGCTGTT CTTCCTCGTG CCGCCGCCGG GCTGGATCGT CGATCGCGTC    16320
ACCGCGCCGC TCAAGGAGTT CGTCTCCTAT GCCGCCACCG GCTTCCTGTC CTGGCTGGAC    16380
```

```
TATCCGATCC  TGCGCCAGGG  CGTGACGCTG  TTCGTCGGCC  CCTATCAGCT  GCTGGTCGAG   16440
GATGCCTGTT  CGGGGCTGCG  CTCGCTCTCC  AGCCTCGTCG  TCGTCACGCT  GCTGTACATC   16500
TACATCAAGA  ACAAGCCGTC  CTGGCGCTAC  GCGCTGTTCA  TCGCCGCGCT  GGTGATCCCG   16560
GTCGCGGTGA  TCACCAACAT  CCTGCGCATC  GTCATCCTCG  TGCTGATCAC  CTATCATATG   16620
GGCGACGAGG  CCGCGCAGAG  CTTCCTCCAC  GTCTCCACCG  GCATGGTGAT  GTTCGTGGTC   16680
GCGCTGCTCT  GCATCTTCGC  CATCGACTGG  GTGGTCGAAC  AGCTCTTCAC  ACGGCGCCGG   16740
AGGCCCCATG  TTAACCGGC   GTGACCTGCT  GATCGGCGCG  GGCTGCTTCG  CCGCCGCCGG   16800
CGCCTCGCTC  GGCCTCAAGC  CGCACCGTCG  CATGGACCTG  CTCGGTGCGA  CCAAGCTCGA   16860
TGCGCTGATG  CCCAAGGCAT  TTGGCGGCTG  GAAGGCCGAG  GATACCGGTG  CGCTGATCGC   16920
CCCCGCGCGC  GAAGGCAGCC  TGGAAGACAA  GCTGTACAAC  CAGGTGGTCG  CCCGTGCCTT   16980
TTCGCGCGCC  GACGGCACCC  AGGTGATGCT  GCTGATCGCC  TATGGCAACG  CCCAGACGGA   17040
TCTGCTGCAG  CTCCACCGAC  CGGAAGTCTG  CTACCCGTTC  TTCGGCTTCA  CCGTGGTCGA   17100
GAGCCACGAG  CAGATCATCC  CGGTGACGCC  GCAGGTGACG  ATTCCCGGAC  GGGCGCTGAC   17160
CGCGACCAAC  TTCAACCGCA  CCGAGCAGAT  CCTCTACTGG  ACCCGCGTGG  GCGAATATCT   17220
GCCGCAGAAC  GGCAACGAGC  AGCTGTTCGC  CCGCCTCAAG  AGCCAGCTCC  AGGGCTGGAT   17280
CGTCGACGGG  GTGCTGGTCC  GCATCTCGAC  TGTGACGGCG  GAAGCCAAGG  ACGGCCTCAA   17340
CGCCAATCTC  GATTTCGCGC  GCGAGCTGGT  GAAGACGCTC  GATCCGCGCG  TGCTGCGCCC   17400
GTTGCTCGGC  ACGCAGGTAA  CGCGCGACCT  GGCGCCGCGC  GCCTGAACGA  AAAAGGGGCG   17460
GCGCAGACCG  CCGCCCCTCC  CTCTCCTTCT  CGTCGCGTAC  CCGCGCTCAG  CGCTCGTGCA   17520
GCGCGTCGCT  GCCGGTTTCG  AGCATCGGGC  CGACGAGATA  GCTCAGCAAT  GTCCGCTTGC   17580
CGGTGACGAT  GTCGGCACTG  GCGATCATGC  CCGGCCGCAG  CGGCACGTGC  CCGCCATTGG   17640
CGATGACATA  GCCGCGGTCC  AGTGCGATCC  GCGCCTTGTA  GACCGGCGGC  TGGCCCTCCT   17700
TCACCTGCAC  CGCCTCGGGC  GCGATGCCCA  CCACCGTGCC  GGGGATCATG  CCATAGCGGG   17760
TGTGCGGGAA  CGCCTGCAGC  TTCACCTTTA  CCGGCATGCC  GGTGCGCACG  AAGCCGATAT   17820
CGCTGTTGTC  CACCATCACC  TCGGCCTCGA  GCCGGGCATT  GTCCGGCACC  AGCGACAGCA   17880
GCGGCTTGGC  GCCCTCCACC  ACGCCGCCTT  CGGTGTGGAC  CTGCAGCTGC  GAGACCGTGC   17940
CGCTGACCGG  CGCGCGCAGT  TCGCGGAACG  AACTGCGCAG  ATTCGCCTTG  GCGACTTCCT   18000
CGCTGCGCGC  CCGCACGTCG  TCCTGCGCCT  TCACCAGATC  CTGCAACACC  TGCGCGCGCG   18060
CCTCCTCGCG  CGTCCTGATC  GACATGCTGC  TGGCACTGCG  CGACTGCTGA  CCAAGCTTGG   18120
CCACCGTCGC  CCGCGCCGCG  GTGAGGTCCT  GCCGTTCGGA  AATGAGCTGG  CGGCGCATCT   18180
CGACCACGCG  CAGCTTCGAG  ACATAGCCCT  TGGCGGCCAT  CGCCTCGTTC  GCGGCGATCT   18240
GCTGCTCGAG  CAGCGGCAGC  GATTGTTCCA  GCTTGCGAAC  CTGCGCCTGT  GCCTCGGCCG   18300
AGGCGGAAGC  GGCGGCACCG  CTGTCCGATC  GGCCGCCGGC  AAGCATCGCC  TCGATCTGGC   18360
CGAGCCGCGC  GCGTGCGAGG  CCGCGATGCG  TCTCGACCTC  CGCGGCGCCT  GCGGCGGCGG   18420
GCGCGGCGAA  GCGGAAGCCC  TTTCCGTCCA  GCGCGTCGAT  GATCGCCTGG  TTGCGCGCGG   18480
CATCGAGCTG  GGCGCTGAGC  AGCGCCACGC  GCGCCTGCGC  GGCTTCGGCT  GCCGACATGG   18540
TGGGATCGAG  CGTGATCAGC  ACCTGGCCCT  TCTGAACCTT  CTGCCCCTCG  CCCACCAGAA   18600
TGCGCCGGAC  GATACCGCTT  TCGGGGGACT  GCACGATCTT  GGTCTCGCCG  ATCGGGGCGA   18660
TGCGGCCCTG  CGTCGGCGCC  ACCACTTCCA  CGCGGCCGAT  TGCCAGCCAG  GCGGTGGTGA   18720
TCGCCAGCCC  CGCCACCATC  ACCCGGCCGG  TGAGGCGCGC  GGTGGGCGAC  ACCGGACGTT   18780
```

| | | | | | | |
|---|---|---|---|---|---|---|
| CGATGATCTC | GAGCGCGGCC | GGCAGGAATT | CGGTATCATA | GGCATCGGCG | CGAGCGGGCA | 18840 |
| GCACGGTGCC | GCGCATGCGG | GCGATCGGGC | CGCCGCGGCC | GATCGGAACA | ACGGCGTTCA | 18900 |
| TGCGGCAATC | TCCCCATATC | CGCTTTGGCG | GCGGTGCAGG | TCGGCATAGC | GGCCGCCCAA | 18960 |
| GCGTAGCAGT | TCGTCATGCC | GGCCGCTCTC | GACGATGCGG | CCCTGCTCCA | GCGTGATGAT | 19020 |
| CCGATCGCAG | GCGCGTACCG | CGGACAGGCG | GTGGGCGATG | ATCACCAGCG | TGCGGCCCGC | 19080 |
| CGAGATGGCG | CGCAGATTGT | TCTGGATCAG | CTCCTCGCTC | TCGGCATCCA | GCGCGGAGGT | 19140 |
| CGCCTCGTCG | AACACCAGGA | TGCGCGGATT | GCCGACCAGC | GCGCGGGCGA | TAGCGAGCCG | 19200 |
| CTGGCGCTGG | CCGCCCGACA | GGTTGACGCC | GCGCTCGACG | ATCTCGGTGT | CATAGCCGCG | 19260 |
| CGGCTGACGC | AGGATGAAGT | CATGCGCACC | CGCCAGCGTC | GCCGCCGCCA | CGACATGCTC | 19320 |
| GAACGGCATC | GCCGGGTTGG | ACAGCGCAAT | GTTCTCGCGG | ATCGAGCGGC | TGAACAGCAG | 19380 |
| ATTTTCCTGC | AGCACGACGC | CGATCTGCCG | GCGCAGCCAG | GCGGGATCGA | GCTGGGCCAC | 19440 |
| ATCCACCTCG | TCGACCAGCA | CGCGGCCCAG | ATCGGGGTG | TTGAGGCGCT | GCAGCAGCTT | 19500 |
| GGCCAGCGTC | GACTTGCCCG | ACCCCGAGGA | GCCGACGATG | CCGAGCGACG | TGCCGGCGGG | 19560 |
| GATGTCGAGC | GTGATGTCGC | TCAGCACCGG | CGGCTGGTCC | TCGGCATAGC | GGAAGGTCAC | 19620 |
| GTTTTCGAAG | CGGATCGCGC | CGCGCAGCAC | CGGCAGCGTC | GCGGCGGAGG | CCGGCCGCGG | 19680 |
| CTCCACCGGA | TGGTTGAGCA | CGTCGCCGAG | GCGCTCGATC | GCGATGCGGA | CCTGCTGGAA | 19740 |
| GTCCTGCCAC | AGCTGGGCCA | TGCGGATCAC | GGGGCCGGAA | ACGCGCTGGG | CGAACATGTT | 19800 |
| GAACGCCACG | AGCGCGCCGA | CGCTCATCGC | GCCACCGATC | ACGGCCTTGG | CGCCGAAGAA | 19860 |
| CAGGATCGCC | GCGAAGCTCA | GCTTGGAGAT | CAGCTCGATC | GCCTGGCTGC | CGGTGTTGGC | 19920 |
| GACGTTGATC | AGCCGCTGCG | ACGAGGCGGT | ATAGGCGGCG | AGCTGACGTT | CCCAGCGATT | 19980 |
| CTGCCAGTGC | GGTTCGACTG | CGGTCGCCTT | GATGGTGTGG | ATGCCGGAGA | CGCTCTCGAC | 20040 |
| GAGCAGCGCG | TTGCTGGCGG | AGCTCTTCTC | GAACTTGTCC | TCGACACGCG | TGCGCAGCGG | 20100 |
| GCCCGCGACG | CCGAACGAGA | CCATCGCATA | GGCGACCAGC | GACACGATCA | CGACGCCGAA | 20160 |
| CAGCATCGGC | GAGTAGAACA | GCATCGCGCC | GAGGAACACG | ACCGTGAACA | GCGGATCGAC | 20220 |
| CATCACCGTC | AGCGACGCAT | TGGTGAGGAA | TTCCCGGATG | GTCTCGAGCT | GGCGGACCCG | 20280 |
| GGTGACGGTG | TCGCCCACCC | GCCGCTTTTC | GAAATAGCCG | AGCGGCAGCG | CCAGCAGATG | 20340 |
| GTGGAACAGC | CGCGCGCCCA | GCTCGACGTC | GATCTTCTGC | GTCGTCTCGG | TGAACAGGCG | 20400 |
| CGTGCGGATC | CAGCCCAGCG | CCACCTCCCA | GACCGACACG | GCCAGGAAGG | CGAAGGCGAG | 20460 |
| CACGCTCAGC | GTGCTCATGC | TGTTGTGGAC | CAGCACCTTG | TCGATCACGC | TCTGGAAGAG | 20520 |
| CAGCGGCGCC | GCGAGGCCGA | GCAGGTTGAG | CGCCAGGGTG | ATGCCCAGCA | CCTCGAGAAA | 20580 |
| CAGCCTGCGA | TACCGCTGGA | ACTGTGCGGC | GAACCAGGAG | AAACCGAATC | GCAGCGCCTG | 20640 |
| GCCGGCCACG | GCGCGCGTCG | TCAGCAGCAC | GAGCGTGCCG | GACCACAGCG | CATCCAGCCC | 20700 |
| CTCGCGGTCG | ACCTGTTCGG | GGGCGTGGCC | GGGACGCTGG | ATGATCACGC | CATGCTCGGT | 20760 |
| CAGGCCACCG | ATCACGAACC | AGCCCTCCGG | GCCGTCGGCG | ATGGCCGGCA | GCGGCTGGCG | 20820 |
| GGCCAGACCG | CCGCGCGGCA | CGTCCACCGC | CTTGGCGCGC | ACGCCCTGCT | GGCGCTTGGC | 20880 |
| GAGCAGGATC | AGGTCGTCGA | CGCTGGCACC | CTCGGCATGG | CCCAGCATGT | GCCGCAGCTG | 20940 |
| TTCGGGGGTG | ACGGCGATGT | TGTGGACGCC | GAGCAGCAGC | GACAGCGCCA | CAAGCCCGGA | 21000 |
| TTCGCGCAAT | TCGCCCTCGC | GCTCGGCGG | AGCCTGGGCG | GCGAACGCGC | CCTGGAGCTG | 21060 |
| TGCCTGCATC | TCGTCGCGTG | TCATTCCGGT | ACTCTGCCTC | CATGGCGCTA | CTGATCGCAG | 21120 |
| CCATGATGAA | CGAGCTCGGT | AAAGACTCGC | TTAAGCCAGA | TTTTTCTGTG | GTTTATACCT | 21180 |

```
ATTGCCGGGG ATGCCGGACC GGACCGGATC GGCAGACGGC AGCCTGCGTT AGTCGGGCCT    21240
TAAAGCGTTG CCGCTAGCAC AAGGACAAGA ATTTTATCGG AGAGGGTCGG GAACCATGCC    21300
CACGCATGAA GGTTGCAGCG CAGCAATATC GACGGATCGC CTCGGAGCCC GAATGCTGCA    21360
TCCGCGAAGT GACTTTCGCC AAAGCAGCTA TAGGATGGCC CGGGGCTTGA TTGCCGCCGT    21420
GCGATCAGCA TAAGCGATCC ATGGTCGCCA AAATCTGTCA TCCTTGGTAA CAATCATGCA    21480
GCCGCTAAGG AAGATGTGCA CGTCTGACGA TGCTTTCTTC CGCACCCCAT GCGCCGCTGA    21540
CTCTGGTAGA TTGACCGTGG CCTCCATTGC TCATCGTCTC GAAAAGGAC CCTCTGGTCG     21600
CCGCGCGGAC TTCCGGGAAT CGATTTGTCC CGTTATAGTG CAATGCAACA GGCCGAATCG    21660
GCCGCTGTCA GCGTGCACAA TCCGTTGAGG GAGCCCGACG AGGCAATGAA CGCTTTTGAA    21720
GCACAGCGCG CCTTTGAGGA GCAGCTCCGG GCCCATGCCC GTTCTGCCCC CAGCGCCGCA    21780
CCCATGCTGC GACGTTCCAC GATCCGCATG ATCCTCTACA CCGAATTGCT GTTGCTCGAC    21840
AGCATCGCAA TTCTACTGGG GTTCTACATC GCGGCCTGCT CGCGCGACGG CAACTGGCTG    21900
TCCCTTGCGG GCGTCAATGT CGGCATCTTC CTCCTGCCGA TCACGCTCGG CACCGCGCTC    21960
GCCAGCGGCA CCTATTCGCT GAGCTGCCTG CGCTACCCGG TCAGCGGGGT GAAGAGCATC    22020
TTCTCGGCGT TCTTCTTCTC GGTGTTCATC GTGCTGCTGG GCAGCTACCT GCTCACCGCG    22080
GAGCTGCCGC TGTCGCGCCT GCAGCTCGGC GAGGGCGTGC TCCTGGCGCT CAGCCTGGTG    22140
ACGATCTGCC GCCTTGGCTT CCGCTGGCAC GTTCGTGCGC TGACACGCGG CACGCTGCTC    22200
GACGAGCTGG TGATCGTCGA CGGCGTTGCC CTGGAGGTCG CGAGCGGCGC GGTCGCGCTC    22260
GATGCGCGCA TCATCAACCT CACGCCCAAC CCGCGCGATC CGCAGATGCT GCATCGCCTC    22320
GGCACCACCG TGGTGGGCTT CGACCGGGTC GTCGTCGCCT GCACCGAGGA GCACCGGGCA    22380
GTATGGGCGC TGCTGCTCAA GGGCATGAAC ATCAAGGGCG AGATCCTCGT CCCCCAGTTC    22440
AACGCGCTGG GCGCGATCGG CGTCGACTCC TATGAGGGCA AGGACACGCT GGTCGTGTCC    22500
CAGGGCCCGC TCAACATGCC GAACCGCGCA AGAAGCGGG CGCTCGATCT GCTCATCACC      22560
GTCCCCGCGC TGGTCGCGCT GGCGCCGCTG ATGATCGTGG TCGCGATCCT GATCAAGCTG    22620
GAGAGCCCCG GCCCCGTCTT CTTCGCACAG GACCGCGTCG GCCGCGGCAA CCGACTGTTC    22680
AAGATCCTCA AGTTCCGCTC GATGCGCGTT GCGCTCTGCG ATGCGAACGG CAACGTCTCG    22740
GCCAGCCGCG ATGACGATCG CATCACCAAG GTAGGCCGGA TCATCCGCAA GACCAGCATC    22800
GACGAGCTGC CGCAGCTGCT CAACGTGCTG CGCGGCGACA TGAGCGTCGT CGGCCCGCGC    22860
CCGCACGCAC TCGGGTCGCG CGCCGCCAAC CATCTCTTCT GGGAAATCGA CGAGCGCTAC    22920
TGGCACCGCC ACACGCTCAA GCCGGGCATG ACGGGCCTCG CGCAGATCCG CGGCTTCCGC    22980
GGCGCGACCG ATCGCCGCGT CGATCTCACC AATCGCCTGC AGGCGGACAT GGAGTATATC    23040
GACGGCTGGG ACATCTGGCG GGACGTCACC ATCCTGTTCA AGACGCTGCG CGTGATCGTG    23100
CACTCCAACG CCTTCTGATC GCGGAGGGGA GCAACGCGAG CACCGCTTGG TGCAAGAGCA    23160
TTGACATCCG CCCTGCTTCT GCATTTGTCA TTTTATCATT GTCGTTGCGG GCCCGCCCGC    23220
GCCATGGGGG ATTTTGAATG AAGGGTATCA TCCTTGCGGG GGGCAGCGGC ACGCGCCTCT    23280
ACCCCGCAAC GCTGTCGATC TCGAAGCAGC TGCTTCCCGT CTATGACAAG CCGATGATCT    23340
TCTACCCCCT GTCGGTGCTG ATGCTCACGG GTATCCGGGA CATCCTGATC ATCTCCACCC    23400
CGCGCGACCT GCCGATGTTC CAGGCGCTGC TCGGCGACGG TTCGGCATTC GGCATCAACC    23460
TGAGCTATGC CGAACAGCCT TCGCCCAACG GCCTTGCGGA AGCCTTCATC ATCGGCGCCG    23520
ATTTCGTCGG CAACGATCCC AGCGCGCTGA TCCTCGGCGA CAACATCTAT CACGGTGAAA    23580
```

```
AGATGGGCGA  GCGCTGCCAG  GCAGCTGCGG  CCCAGGCATC  GCAGGGCGGC  GCGAACGTGT   23640
TCGCCTATCA  TGTCGACGAT  CCCGAGCGCT  ACGGCGTGGT  CGCGTTCGAT  CCGGAGACGG   23700
GCGTCGCTAC  CAGCGTCGAG  GAAAAGCCGG  CCAACCCCAA  GTCCAATTGG  GCGATCACCG   23760
GGCTTTATTT  CTACGACAAG  GACGTGGTCG  ACATCGCCAA  GTCGATCCAG  CCCTCGGCGC   23820
GCGGCGAACT  CGAGATCACC  GACGTCAACC  GCATCTACAT  GGAGCGCGGC  GACCTCCACA   23880
TCACCCGGCT  CGGTCGCGGC  TATGCCTGGC  TCGACACCGG  CACGCATGAC  AGCCTGCACG   23940
AGGCCGGCTC  GTTCGTCCGC  ACGCTGGAGC  ACCGCACCGG  CGTGAAGATC  GCCTGCCCGG   24000
AGGAAATCGC  CTTCGAGAGC  GGCTGGCTGG  GCGCCGACGA  TCTGCTCAAG  CGCGCCGCCG   24060
GCCTCGGCAA  GACGGGGTAT  GCCGCCTATC  TGCGCAAGCT  GGTAGCCGCG  GCATGACCCA   24120
GGTGCATCAC  CACGCGCTAT  CGGGCGTCAT  CGAGTTCACC  CCGCCCAAGT  ACGGCGATCA   24180
CCGCGGCTTC  TTCTCCGAGG  TGTTCAAGCA  GTCCACGCTC  GACGCCGAAG  GCGTCGAGGC   24240
GCGGTGGGTG  CAGGACAATC  AGAGCTTCTC  GGCCGCACCG  GCACGATCC  GCGGACTGCA   24300
CCTGCAGGCG  CCGCCCTTCG  CCCAGGCCAA  GCTGGTGCGC  GTGCTGCGCG  GCGCGATCTA   24360
CGACGTCGCG  GTCGACATTC  GCCGCGGCTC  GCCCACATAC  GGCCAGTGGG  TCGGCGTCGA   24420
GCTTTCGGCG  GACAAGTGGA  ACCAGCTGCT  GGTGCCGGCC  GGCTATGCGC  ATGGCTTCAT   24480
GACGCTCGTC  CCGGATTGCG  AGATCCTCTA  CAAGGTCAGC  GCCAAATATT  CGAAGGAATC   24540
GGAGATGGCG  ATCCGCTGGG  ATGATCCCGA  TCTCGCCATC  ACCTGGCCGG  ACATCGGCGT   24600
CGAGCCGGTG  CTCTCCGAAA  AGGACGCGGT  CGCTACCCCG  TTCGCCGAAT  TCAACACCCC   24660
CTTCTTCTAT  CAGGGCTGAT  CCATGCAGCA  GACCTTCCTC  GTTACCGGCG  GCGCCGGCTT   24720
CATCGGCTCG  GCAGTGGTAC  GCCACCTCGT  TCGCCAGGGC  GCGCGCGTCA  TCAATCTCGA   24780
CAAGCTCACC  TATGCGGGCA  ACCCGGCCTC  GCTGACCGCG  ATCGAGAACG  CCCCCAACTA   24840
CCGCTTCGTC  CACGCCGATA  TCGCCGACAC  CGCGACGATC  CTGCCGCTGC  TGCGCGAAGA   24900
GCAGGTCGAC  GTGGTGATGC  ACCTCGCCGC  CGAGAGCCAT  GTCGATCGCT  CGATCGACGG   24960
CCCGGGCGAG  TTCATCGAGA  CCAACGTCGT  CGGCACCTTC  AAGCTGCTCC  AGGCGGCGCT   25020
GCAATATTGG  CGCGAGCTGG  AAGGGGAGAA  GCGCGAGGCT  TTCCGCTTCC  ACCACATTTC   25080
CACCGACGAG  GTGTTCGGCG  ACCTGCCGTT  CGACAGCGGC  ATCTTCACCG  AAGAGACGCC   25140
CTATGATCCC  TCCTCGCCCT  ATTCGGCGTC  GAAGGCGGCC  AGCGACCATC  TGGTCCGCGC   25200
CTGGGGTCAC  ACCTATGGCC  TGCCCGTGGT  GCTGTCGAAC  TGCTCGAACA  ATTACGGGCC   25260
GTTCCACTTC  CCCGAGAAGC  TGATCCCGCT  GACCATCCTC  AACGCGCTGG  AAGGCAAGCC   25320
CCTGCCCGTC  TACGGCAAGG  GCGAGAATAT  CCGCGACTGG  CTGTACGTCG  ACGATCACGC   25380
CAAGGCGCTG  GCGACGATCG  CCACGACCGG  CAAGGTCGGC  CAGAGCTACA  ATGTCGGCGG   25440
CCGCAACGAG  CGCACCAACC  TGCAGGTCGT  CGAGACGATC  TGCGACCTGC  TCGATCAGCG   25500
CATTCCGCTG  AAGGATGGCA  AGAAGCGCCG  CGAGCTGATC  ACCTTCGTCA  CCGATCGCCC   25560
CGGCCATGAC  CGCCGCTACG  CGATCGACGC  GACCAAGCTC  GAGACCGAAC  TGGGCTGGAA   25620
GGCCGAGGAG  AATTTCGACA  CCGGCATCGC  CGCGACGATC  GACTGGTATC  TCGAGAATGA   25680
ATGGTGGTGG  GGTCCGATCC  GCTCCGGCAA  ATATGCCGGC  GAGCGGTTGG  GGCAGACCGC   25740
CTGATGCGCA  TCCTCGTCAC  CGGGCATGAC  GGCCAGGTCG  CCCAGGCGCT  GGGCGAACAG   25800
GCGGAGGGCC  ATGAGCTGAT  CTTCACCAGC  TATCCCGAGT  TCGATCTCTC  CAAGCCGGAG   25860
ACGATCGAGG  CGGCGGTGGC  GAAGATCCAG  CCCGAGCTGA  TCGTGTCGGC  GGCTGCGTAT   25920
ACGGCGGTCG  ACAAGTCCGA  GAGCGAGCCC  GAGCTCGCCA  TGGCGATCAA  CGGCGACGGC   25980
```

```
CCCGGCGTAC TGGCGCGCGC GGGCGCGAAG ATCGGCGCGC CGATCATCCA TCTGTCGACC    26040
GACTATGTGT TCGACGGCAG CCTGGACCGC CCGTGGCGCG AAGACGACCC CACCGGTCCG    26100
CTCGGCGTCT ATGGCGCCAC CAAGCTGGCC GGCGAGCAAG CGGTGCAGGC CTCGGGCGCG    26160
ACCAACGCGG TGATCCGGCT CGCCTGGGTC TACAGCCCGT TCGGCAACAA CTTCGTCAAG    26220
ACGATGCTGC GCCTCGCCGA GACGCGGGAC ACGCTGAACG TGGTCGAGGA CCAGCAGGGC    26280
TGCCCGAGCT CGGCGCTGGA CATCGCCACG GCGATCCTCA AGGTCGTCGG CCACTGGCAG    26340
CAGAACGGCG CCACCAGCGG CCTGTATCAC TTCACCGGAT CGGGCGAGAC CAACTGGGCC    26400
GACTTCGCGC GCGCGATCTT CGCGGAAAGC GCCAAGCACG GCGGTCCGAC CGCCGAGGTG    26460
ACCGGCATTC CGACCTCCGG CTACCCCACC CCGGCGAAGC GCCCGGCCAA TTCGCGGCTC    26520
AATTGCGACA AGTTCGCCGA AACCTTCGGC TATCGTGCAC CCGCCTGGCA GGACTCGGTG    26580
GCGGAAGTGG TAGGCCGCCT CCTGGCATAA AATGCCCGGC CCGACCCTGT GCGCGGCGGG    26640
GTGGCTGCGC ACTCCGGTCG GGTTTCATCG ACATCGCCGG CTGCGGGGAG CATCACCGAT    26700
GCTCCCCGAT CAGCGCCAGG CCGTCACTTC CTGAACGGCG CGACCAGGGG CTTGATCGTC    26760
TTGAACACGG CCTCACGCAG CGTCCGCACG GGCGCGGCGA CGAGGTGATC GAACGCGAGC    26820
GTCATCCCGC TCACCCGCTG GGGTGCGACG TCGCTGCGGA TCTTGAACGA TTCGACCACC    26880
TCGATATCGG AAACCAGCCG CCCCTTGATG CGGTTGATGA CATTCTCGCC ATGCACCACC    26940
TGCAGCCATA CCGGCCGCCC GGCGACCTGG GTGATCTTCC ACTTCTGGCC CAGCTCATGA    27000
TGGGGCTTGG CCCAGATCGT CTCGACGCTG GCGAGATCGC GCTCGACCAG CGAGGTGAAC    27060
GGATTGCTGT GGTCCGCAGC GGTGTAGAGC CGGCCCTGGC GCATCGCGAT GCCCTGGGTG    27120
AAGTTCAGCA CCGTCTGTGC CGGCGCATCC TTCGCCGCGG CCTGCACCCG TGCCACGAAG    27180
TCGTTCGAAA GCGCGTCGTC ATTGTCCAGC CGCGTGGTGA CGATCAGCTG CTCGCCGGGC    27240
GTCGCCAGCG CCTTCACGTC GTCCGCGATC ATCGCCTTGT CGAACATCGC GACGTAGCGC    27300
GGCGTGAAGT TGTAGATCTG CCGATCGCGC TCGATCCGCT CGCGGAACTC GGCGGGGGTG    27360
TCCTTGTCGA AGTAGATGAG CCAGTGGAAG TTGCGCTCGG TCTGGCCCGC GATGCTCGGC    27420
AGGCAGAACT GCTCGAACAG CCCGAAACGG CGGTCGAGCC AACCCGGCGA ATTGCGGATC    27480
GCCACCTCGC GGCCCGGGCT GGCGATGTTG AAGCGCGTCA GGATCACGTG AAGCATCGGT    27540
TCGATCAGCC CCGGTCTAGC AAAACGAAGA AAGCCCGGCC GCTACAACGG CCTTGTTCGA    27600
ACAACGCGCA AGAAACAGGG TACACGCGAA CGGCACGTTC GTCTTCGCCC ACCCGCTGG    27660
TTGCCGCCAT TCCCACGAAC GGTTACGGGA TATTCCGGAA CTGGGCAACC GGGGATTGCT    27720
GCACTGCGCA ATGACACGCG GCCGGAATGA CAAACGGCTT GCCGCCCGCG CCCCCCGCGC    27780
CTAACCCTCC GCCCGTGCCC GACGCCCGTC CCGATCGCAT TGCCACCGGC CTGGCGCTTC    27840
GCCTGTTCGC CATTGCCTGC CTGTCGACCA TGTCGGCGCT CATCAAGATG TCGGAACTGC    27900
GCGGCGCCTC GCTGATCGAG ACGATGTTCC ACCGCCAGCT CTGGGCGGTG CCGCTGGTCA    27960
CCTTGTGGGT GGTGATGGGC CCGGGGCTCA AGTCGCTCAA GACGCAGCGC TTCGGCGCGC    28020
ATGTCTGGCG CACCGCGGTG GGCCTCACCG GCATGATCTT CACCTTCGGC GCGGTGATCC    28080
TGCTGCCCCT GGCCGAGGCG CAGACCTTCC AGTTCACCGT GCCCATCTTC GCCACGCTGC    28140
TCGGCGCGCT GATCCTCGGC GAGCCGACCG GCCGGCATCG CTGGGGCGCA GTGATCGTCG    28200
GCTTCCTCGG CGTGCTGATC GTCGTCCAGC CGGGCCGGGA AGCCATTCCG ATCTTCGGCG    28260
CCTTCGTCGG GCTGATGGCG GCGTTGTTCG TCGCCATCGT CGCGATCACG CTGCGGCAGA    28320
TCACCCGCAC CGAAAGCGCC GGCACCACCG TCTTCTGGTT CTCGCTGCTC TCGGTGCCCG    28380
```

| | | | | | | |
|---|---|---|---|---|---|---|
| TGCTCGGCGC | CATCTACGCG | TTCAACTTCC | GTCCGCACGA | TGCCGAGACC | TGGGCGATCC | 28440 |
| TCATCGCCAC | AGGACTGGTG | GGCGGCGTCG | GCCAGCTGGC | GCTGACCGGT | GCGATGCGCT | 28500 |
| TCGCCCCCGT | CTCGGCGGTG | GTACCGATGG | ACTATTCGGG | GCTGATCTGG | GCGACGCTCT | 28560 |
| ACGGCTGGCT | GCTGTTCGAC | GTGTTCCCGA | CCTTCTCGAC | CTGGCTCGGT | GCGCCGGTGA | 28620 |
| TCATCGCCAG | CGGGCTCTAC | ATCGTCTATC | GCGAGCAGAA | GCTGGCCCGC | GGCCAGGCTA | 28680 |
| GCTACGCCGA | AACGCCACTA | TGAGGTTGTT | GGCGGGCATC | GCCACCCGCC | GATCGAACAC | 28740 |
| CAGGCCTTGC | GCCCCCGCCG | CCGCGATCAC | CTCGTCCAGC | AAGCGCAGCC | CCCAGGCAGG | 28800 |
| ATCC | | | | | | 28804 |

We claim:

1. An isolated DNA sequence isolated from DNA of sphingan-producing bacteria selected from the group consisting of Sphingomonas sp., with the exception of ATCC 31461 ATCC 31554 and ATCC 53272, said DNA sequence when incorporated into a recipient Sphingomonas sp. bacterium in multiple copies produces a hyperproducer of sphingan polysaccharide relative to said recipient bacterium wherein said sphingan polysaccharide has the general formula:

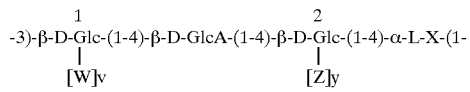

wherein Glc is glucose; GlcA is glucuronic acid; Rha is rhamnose; Man is mannose: X is Rha or Man; Z is attached to Glc residue 2 and is selected from the group consisting of α-L-Rha-(1–6-α-L-Rha, α-L-Man and α-L-Rha; W is at5ached to Glc residue number 1 and is β-D-Glc-(1–6)-α-D-Glc or α-L-Rha; subscripts v and y may be 0, 0.33, 0.5, 0.67 or 1: and wherein the reducing end of the polymer is toward the X residue of the backbone, such that the backbone excludes W and Z when v and y are equal to 0.

2. The DNA sequence according to claim 1 isolated from a strain of Sphingomonas bacteria selected from the group consisting of ATCC31853, ATCC21423, ATCC31555, ATCC31961, and ATCC53159.

3. The DNA sequence according to claim 1 containing a gene which codes for a glycosyl transferase enzyme.

4. The DNA sequence according to claim 3 wherein said glycosyl transferase enzyme is glucosyl IP-transferase.

5. The DNA sequence according to claim 1 which contains an operon or gene which encodes an enzyme in the rhamnose biosynthesis pathway.

6. A method of engineering a bacterium derived from a strain of Sphingomonas sp. to be a hyperproducer of sphingan polysaccharide comprising:

isolating a DNA sequence from DNA of donor sphingan-producing bacteria selected from the group consisting of Sphingomonas sp., with the exception of ATCC 31461, ATCC 31554 and ATCC 53272; and inserting said DNA sequence into a recipient sphingomonas sp. bacterium in multiple copies to produce a bacterium which hyperproduces sphingan polysaccharide relative to said recipient bacterium under identical fermentation conditions wherein said sphingan polysaccbaride has the general formula:

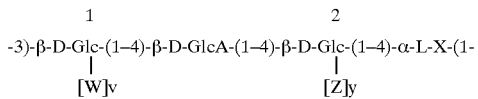

wherein Glc is glucose: GlcA is glucuronic acid: Rha is rhamnose: Man is mannose: X is Rha or Man Z is attached to Glc residue 2 and is selected from the group consisting of α-L-Rha-1–6)-α-L-Rha, α-L-Man and α-L-Rha, W is attached to Glc residue number 1 and is β-D-Glc-(1–6)-α-D-Glc or α-L-Rha: subscripts v and y may be 0, 0.33, 0.5, 0.67 or 1: and wherein the reducing end of the polymer is toward the X residue of the backbone, such that the backbone exclude W and Z when v and y are equal to 0.

7. The method according to claim 6 wherein said bacterium into which said DNA sequence is inserted is a member of a strain of Sphingomonas selected from the group consisting of ATCC31554, ATCC31461, ATCC31853, ATCC21423, ATCC31555, ATCC31961, ATCC53159 and ATCC53272.

8. The method according to claim 6 wherein said bacterium into which said DNA sequence is inserted is a member of a strain of Sphingomonas selected from the group consisting of ATCC31554, ATCC31461 and ATCC53272.

9. The method according to claim 6 wherein said DNA sequence is isolated from a strain of Sphingomonas selected from the group consisting of ATCC31853, ATCC21423, ATCC31555, ATCC31961, and ATCC53159.

10. The method according to claim 6 wherein said DNA sequence contains a gene which codes a glycosyl transferase enzyme.

11. The method according to claim 10 wherein said glycosyl transferase enzyme is glucosyl IP-transferase.

12. The method according to claim 6 wherein said DNA sequence contains an operon or gene which encodes an enzyme in the rhamnose biosynthesis pathway.

13. A bacterium derived from a strain of Sphingonmonas sp., said bacterium containing multiple copies of a DNA sequence isolated from DNA of donor sphingan-producing bacteria selected from the group consisting of Sphingomonas sp. with the exception of ATCC31461, ATCC31554 and ATCC 53272, said DNA sequence, when inserted in multiple copies into a recipient Sphingomonas sp. bacterium, results (resulting) in said recipient bacterium becoming a hyperproducer of sphingan polysaccharide.

14. The bacterium according to claim 13 derived from a strain of Sphingomonas selected from the group consisting ATCC31554, ATCC31461, ATCC31853, ATCC21423, ATCC31555, ATCC31961, ATCC53159 and ATCC53272.

15. The bacterium according to claim 13 derived from a strain of Sphingomonas selected from the group consisting ATCC31554, ATCC31461 and ATCC53272.

16. The bacterium according to claim 13 wherein said DNA sequence is isolated from a strain of Sphingomonas selected from the group consisting ATCC31853, ATCC21423, ATCC31555, ATCC31961, and ATCC53159.

17. The bacterium according to claim 13 wherein said strain is ATCC31554.

18. The bacterium according to claim 13 wherein said strain is ATCC31461.

19. The bacterium according to claim 13 wherein said strain is ATCC53272.

20. The bacterium according to 13 wherein said DNA sequence contains a gene which codes a glycosyl transferase enzyme.

21. The bacterium according to claim 20 wherein said glycosyl transferase enzyme is glucosyl IP-transferase.

22. The bacterium according to claim 13 wherein said DNA sequence contains an operon or gene which encodes an enzyme in the rhamnose biosynthesis pathway.

23. A method of enhancing the production of sphingan in a Sphingomonas bacterium comprising:
  1) incorporating a DNA sequence isolated from a strain of donor sphingan-producing Sphingomonas bacteria selected from the group consisting of Sphingomonas sp., with the exception of ATCC 31461, ATCC 31554 and ATCC 53272, into a recipient Sphingomonas bacterium in multiple copies to produce a bacterium which hyperproduces sphingan polysaccharide relative to said recipient bacterium;
  2) culturing the bacterium from step 1 in a fermentation broth to produce sphingan; and
  3) isolating the sphingan from step 2 wherein said sphingan polysaccharide has the general formula:

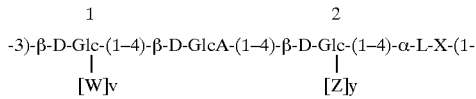

wherein Glc is glucose: GlcA is glucuronic acid; Rha is rhamnose; Man is mannose; X is Rha or Man; Z is attached to Glc residue 2 and is selected from the group consisting of α-L-Rha-(1–6)-α-L-Rha, α-L-Man and α-L-Rha; W is attached to Glc residue number 1 and is β-D-Glc-(1–6)-α-D-Gla or α-L-Rha: subscripts v and y may be 0, 0.33, 0.5, 0.67 or 1: and wherein the reducing end of the polymer is toward the X residue of the backbone such that the backbone excludes W and Z when v and y are equal to 0.

24. The method according to claim 23 wherein said bacterium into which said DNA sequence is incorporated is a member of a strain of Sphingomonas selected from the group consisting of ATCC31554, ATCC31461, ATCC31853, ATCC21423, ATCC31555, ATCC31961, ATCC53159 and ATCC53272.

25. The method according to claim 23 wherein said bacterium into which said DNA sequence is incorporated is a member of a strain of Sphingomonas selected from the group consisting of ATCC31554, ATCC31461 and ATCC53272.

26. The method according to claim 23 wherein said DNA sequence is isolated from a strain of Sphingomonas selected from the group consisting of ATCC31853, ATCC21423, ATCC31555, ATCC31961, and ATCC53159.

27. The method according to claim 23 wherein said DNA sequence contains a gene which codes a glycosyl transferase enzyme.

28. The method according to claim 27 wherein said glycosyl transferase enzyme is glucosyl IP-transferase.

29. The method according to claim 13 wherein said DNA sequence contains an operon or gene which encodes an enzyme in the rhamnose biosynthesis pathway.

30. The method according to claim 23 wherein said method further comprises the step of isolating said DNA sequence prior to said incorporating step (1).

31. A method of producing sphingan comprising culturing a Sphingomonas bacterium in a fermentation broth to produce sphingan and isolating the sphingan from the cultured fermentation broth, said Sphingomonas bacterium being the bacterium of claim 13.

* * * * *

UNITED STATES PATENT AND TRADEMARK OFFICE
CERTIFICATE OF CORRECTION

PATENT NO. : 5,854,034
DATED : December 29, 1998
INVENTOR(S) : Thomas J. POLLOCK, et al It is certified that error appears in the above-identified patent and that said Letters Patent is hereby corrected as shown below:

TITLE PAGE

[73]   Assignees:   Shin-Etsu Bio, Inc., San Diego, Calif.;
Shin-Etsu Chemical Co., Ltd., Tokyo Japan Signed and Sealed this Eighteenth Day of May, 1999

*Attest:*

Q. TODD DICKINSON

*Attesting Officer*    Acting Commissioner of Patents and Trademarks